(12) United States Patent
Nash et al.

(10) Patent No.: US 7,269,519 B2
(45) Date of Patent: Sep. 11, 2007

(54) METHOD FOR PRODUCING AND SCREENING MASS-CODED COMBINATORIAL LIBRARIES FOR DRUG DISCOVERY AND TARGET VALIDATION

(75) Inventors: Huw M. Nash, Cambridge, MA (US); Seth Birnbaum, Boston, MA (US); Edward A. Wintner, Boston, MA (US); Krishna Kalghatgi, Westborough, MA (US); Gerald Shipps, Stoneham, MA (US); Satish Jindal, Milton, MA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/385,558

(22) Filed: Mar. 11, 2003

(65) Prior Publication Data

US 2004/0014137 A1 Jan. 22, 2004

Related U.S. Application Data

(62) Division of application No. 09/373,018, filed on Aug. 11, 1999, now Pat. No. 6,714,875, which is a division of application No. 09/024,592, filed on Feb. 17, 1998, now Pat. No. 6,207,861.

(60) Provisional application No. 60/070,456, filed on Jan. 5, 1998.

(51) Int. Cl.
| | |
|---|---|
| *G01N 24/00* | (2006.01) |
| *G01N 33/53* | (2006.01) |
| *C12Q 1/68* | (2006.01) |
| *C12Q 1/02* | (2006.01) |

(52) U.S. Cl. .............................. 702/23; 435/6; 435/7.1; 435/7.8; 435/29

(58) Field of Classification Search .................. 702/23; 435/7.1

See application file for complete search history.

(56) References Cited

FOREIGN PATENT DOCUMENTS

| WO | WO 9701635 A1 * | 1/1997 |
|---|---|---|
| WO | WO 9701755 A2 * | 1/1997 |

OTHER PUBLICATIONS van Breeman et al. Pulsed ultrafiltration mass spectrometry: A new method for screening combinatorial libraries. Analytical Chemistry. (1997) vol. 69, pp. 2159-2164.*

Carell et al. New promize in combinatorial chemistry: synthesis, characterization and screening of small-molecule libraries in solution. Chemistry and Biology. (1995) vol. 2, No. 3, pp. 171-183.*

Hsieh et al. Multidimensional chromatography coupled with mass spectrometry for target-based screening. Molecualr Diversity (1996) vol. 2, pp. 189-196.*

* cited by examiner

*Primary Examiner*—Marjorie A. Moran
(74) *Attorney, Agent, or Firm*—Palaiyur S. Kalyanaraman

(57) ABSTRACT

The present invention provides a method for identifying a member of a mass-coded combinatorial library which is a ligand for biomolecule and assessing the effect of the binding of the ligand to the biomolecule. The mass-coded molecular library comprises compounds of the general formula $XY_n$, wherein n is an integer from 2 to about 6, X is a scaffold and each Y is, independently, a peripheral moiety. The mass-coded combinatorial library is produced by reacting a scaffold precursor with a sufficient number of distant peripheral moiety precursors such that there exist at least about 250 distinct combinations of n peripheral moieties derived from the peripheral moiety precursors.

23 Claims, 5 Drawing Sheets

METHOD FOR PRODUCING AND SCREENING MASS-CODED COMBINATORIAL LIBRARIES FOR DRUG DISCOVERY AND TARGET VALIDATION

CROSS REFERENCE TO RELATED APPLICATIONS

This Application is a Divisional of U.S. patent application Ser. No. 09/373,018, filed Aug. 11, 1999 now U.S. Pat. No. 6,714,875 which is a divisional of Ser. No. 09/024,592, filed Feb. 17, 1998, now U.S. Pat. No. 6,207,861, issued Mar. 27, 2001, which claims the benefit of U.S. Provisional Application No. 60/070,456, filed Jan. 5, 1998.

BACKGROUND OF THE INVENTION

Genomics is identifying the genes responsible for all human functions and diseases. With 80,000 genes in the human genome, the thousands of genes involved in development, stature, intelligence, and other features of a human being are being defined. Humans suffer from hundreds of inherited and infectious diseases, and the genes involved in such are also being identified. Proteins encoded by all these genes are targets for therapeutic drugs. However, drugs that can be applied to human function and disease will not simply emerge from genomic information. Conventional drug development for a single disease is a lengthy, tedious and extremely expensive process. Technologies that eliminate the major hurdles facing drug development in the post-genomic era would be of substantial value.

SUMMARY OF THE INVENTION

The present invention provides a method for producing a mass-coded set of chemical compounds having the general formula $X(Y)_n$, where X is a scaffold, each Y is, independently, a peripheral moiety, and n is an integer greater than 1, typically from 2 to about 6. The method comprises selecting a peripheral moiety precursor subset from a peripheral moiety precursor set. The subset includes a sufficient number of peripheral moiety precursors that at least about 50, 100, 250 or 500 distinct combinations of n peripheral moieties derived from the peripheral moiety precursors in the subset exist. The subset of peripheral moiety precursors is selected so that at least about 90% of all possible combinations of n peripheral moieties derived from the subset of peripheral moiety precursors have a molecular mass sum which is distinct from the molecular mass sums of all of the other combinations of n peripheral moieties. The method further comprises contacting the peripheral moiety precursor subset with a scaffold precursor which has n reactive groups, each of which is capable of reacting with at least one peripheral moiety precursor to form a covalent bond. The peripheral moiety precursor subset is contacted with the scaffold precursor under conditions sufficient for the reaction of each reactive group with a peripheral moiety precursor, resulting in a mass-coded set of compounds of the general formula $X(Y)_n$.

In another embodiment, the invention provides a method of identifying a member or members of a mass-coded combinatorial library which are ligands for a biomolecule, for example, a protein or a nucleic acid molecule, such as DNA or RNA. The method comprises the steps of (1) contacting the biomolecule with the mass-coded molecular library, whereby members of the mass-coded molecular library which are ligands for the biomolecule bind to the biomolecule to form biomolecule-ligand complexes and members of the mass-coded library which are not ligands for the biomolecule remain unbound; (2) separating the biomolecule-ligand complexes from the unbound members of the mass-coded molecular library; (3) dissociating the biomolecule-ligand complexes; and (4) determining the molecular mass of each ligand to identify the set of n peripheral moieties present in each ligand.

In a further embodiment, the invention provides a method for identifying a member or members of a mass-coded molecular library which are ligands for a biomolecule and bind to the biomolecule at the binding site of a ligand known to bind the biomolecule (a known ligand). The method comprises the steps of: (1) contacting the biomolecule with the mass-coded molecular library, so that members of the mass-coded molecular library which are ligands for the biomolecule bind to the biomolecule to form biomolecule-ligand complexes and members of the mass-coded library which are not ligands for the biomolecule remain unbound; (2) separating the biomolecule-ligand complexes from the unbound members of the mass-coded molecular library; (3) contacting the biomolecule-ligand complexes with a ligand known to bind the biomolecule, to dissociate biomolecule-ligand complexes in which the ligand binds to the biomolecule at the binding site of the known ligand, thereby forming biomolecule-known ligand complexes and dissociated ligands; (4) separating the dissociated ligands and biomolecule-ligand complexes; and (5) determining the molecular mass of each dissociated ligand to identify the set of n peripheral moieties present in each dissociated ligand.

In a yet further embodiment, the invention provides a method for identifying a member or members of a mass-coded combinatorial library which are ligands for a first biomolecule but are not ligands for a second biomolecule. The method comprises the steps of: (1) contacting the first biomolecule with the mass-coded molecular library, whereby members of the mass-coded molecular library which are ligands for the first biomolecule bind to the first biomolecule to form first biomolecule-ligand complexes and members of the mass-coded library which are not ligands for the first biomolecule remain unbound; (2) separating the first biomolecule-ligand complexes from the unbound members of the mass-coded molecular library; (3) dissociating the first biomolecule-ligand complexes; (4) determining the molecular mass of each ligand for the first biomolecule; (5) contacting the second biomolecule with the mass-coded molecular library, whereby members of the mass-coded molecular library which are ligands for the second biomolecule bind to the second biomolecule to form second biomolecule-ligand complexes and members of the mass-coded library which are not ligands for the second biomolecule remain unbound; (6) separating the second biomolecule-ligand complexes from the unbound members of the mass-coded molecular library; (7) dissociating the second biomolecule-ligand complexes; (8) determining the molecular mass of each ligand for the second biomolecule; and (9) determining which molecular masses determined in step (4) are not determined in step (8). This provides the molecular masses of members of the mass-coded combinatorial library which are ligands for the first biomolecule, but are not ligands for the second biomolecule.

In another embodiment, the method for identifying a member or members of a mass-coded combinatorial library which are ligands for a first biomolecule but are not ligands for a second biomolecule comprises the steps of: (1) contacting the second biomolecule with the mass-coded molecular library, so that members of the mass-coded molecular library which are ligands for the second biomolecule bind to the second biomolecule to form second biomolecule-ligand complexes and members of the mass-coded library which are not ligands for the second biomolecule remain unbound; (2) separating the second biomolecule-ligand complexes from the unbound members of the mass-coded molecular library; (3) contacting the first biomolecule with the unbound members of the mass-coded molecular library of step (2), whereby members of the mass-coded molecular library which are ligands for the first biomolecule bind to the first biomolecule to form first biomolecule-ligand complexes and members of the mass-coded library which are not ligands for the first biomolecule remain unbound; (4) dissociating the first biomolecule-ligand complexes; and (5) determining the molecular mass of each ligand for the first biomolecule. Each molecular mass determined corresponds to a set of n peripheral moieties present in a ligand for the first biomolecule which is not a ligand for the second biomolecule.

In yet another embodiment, the present invention relates to a method for identifying a member of a mass-coded combinatorial library which is a ligand for a biomolecule and assessing the the effect of the binding of the ligand to the biomolecule. The method comprises the steps of: contacting the biomolecule with the mass-coded molecular library, whereby members of the mass-coded molecular library which are ligands for the biomolecule bind to the biomolecule to form biomolecule-ligand complexes and members of the mass-coded library which are not ligands for the biomolecule remain unbound; separating the biomolecule-ligand complexes from the unbound members of the mass-coded molecular library; dissociating the biomolecule-ligand complexes; determining the molecular mass of each ligand to identify the set of n peripheral moieties present in each ligand. The molecular mass of each ligand corresponds to a set of n peripheral moieties present in that ligand, thereby identifying a member of the mass-coded combinatorial library which is a ligand for the biomolecule. The method further comprisies assessing in an in vivo or in vitro assay the effect of the binding of the ligand to the biomolecule on the function of the biomolecule.

The method of the invention allows rapid production of mass-coded combinatorial libraries comprising large numbers of compounds. The mass-coding enables the identification of individual combinations of scaffold and peripheral moieties by molecular mass. The libraries prepared by the method of the invention also allow the rapid identification of compounds which are ligands for a given biomolecule.

DETAILED DESCRIPTION OF THE INVENTION

Figure 1A:
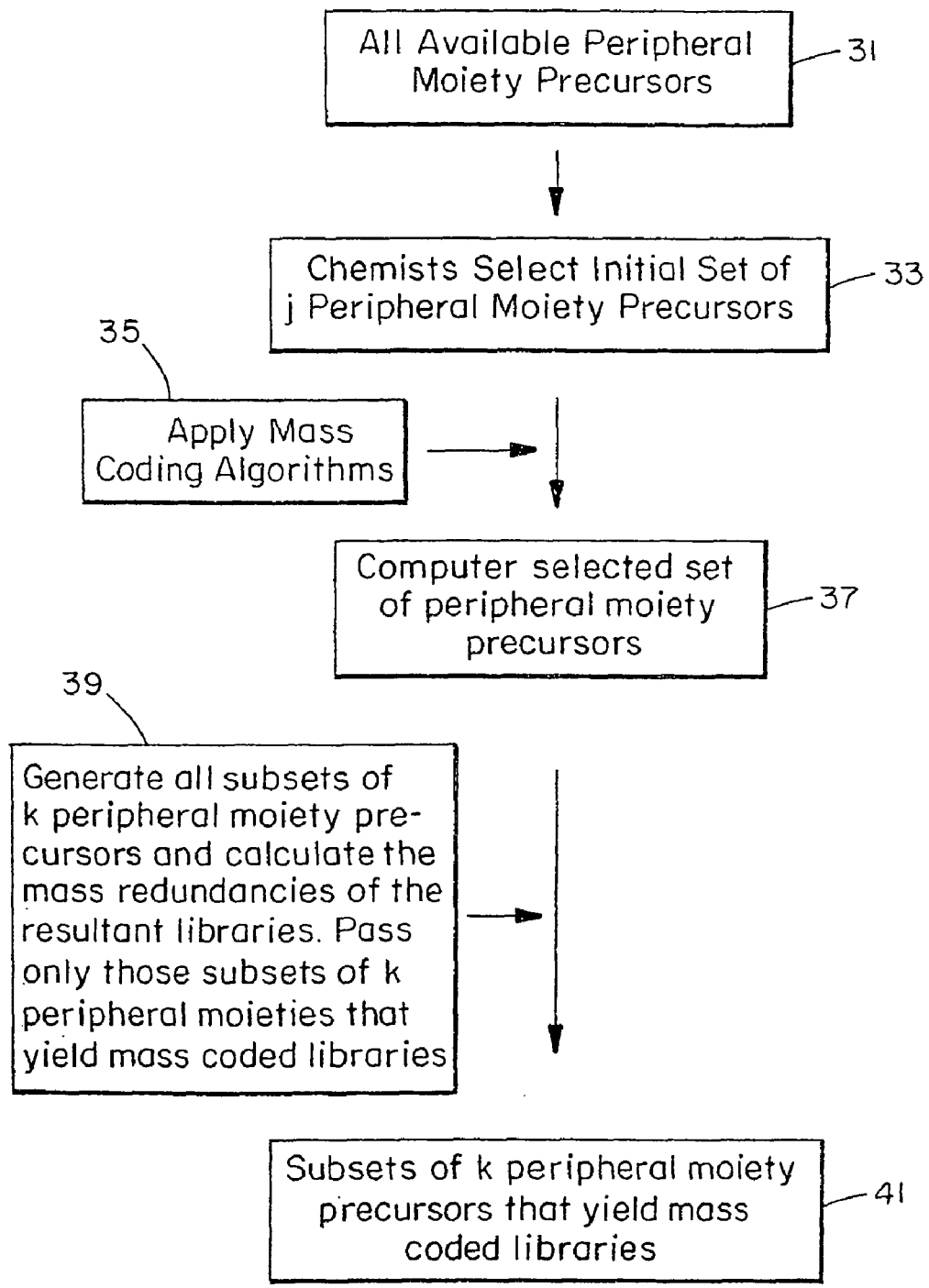
FIGS. 1A and 1B are flow charts illustrating a procedure and alternative procedure, respectively, for selecting a subset of peripheral moiety precursors from among a larger set of peripheral moiety precursors for the production of a mass-coded combinatorial library.

The major hurdles in drug development include a need for: 1) combinatorial chemistry technology that enables rapid production of nearly unlimited numbers of compounds while incorporating the ability to identify efficiently single chemical compounds that bind tightly to a specific biomolecule target, such as a protein or nucleic acid molecule; 2) extremely efficient target-based screening technologies that permit rapid identification of chemical compounds within a large library mixture that become tightly associated with a target biomolecule, even when the function of that biomolecule is not well understood and 3) an information data set that describes how chemical components interact with biomolecules of medical importance.

The present invention provides a method of producing a mass-coded set of compounds, such as a mass-coded combinatorial library. The compounds are of the general formula $X(Y)_n$, wherein X is a scaffold, each Y is a peripheral moiety and n is an integer greater than 1, typically from 2 to about 6. The term "scaffold", as used herein, refers to a molecular fragment to which two or more peripheral moieties are attached via a covalent bond. The scaffold is a molecular fragment which is common to each member of the mass-coded set of compounds. The term "peripheral moiety", as used herein, refers to a molecular fragment which is bonded to a scaffold. Each member of the set of mass-coded compounds will include a combination of n peripheral moieties bonded to the scaffold and this set of compounds forms a mass coded combinatorial library.

The term "combination", as used herein, refers to all permutations of m moieties having n members where m is an integer greater than 2, n is an integer greater than 1 and m is greater than or equal to n, such that:
(1) Permutations having n members in which a given moiety is present from 0 to n times are included.
(2) Permutations having the same n moieties but ordered differently are included once and only once.

The number of combinations of all permutations of m moieties having n members may be calculated from the formula:

$$\text{Combinations} = k!/((k-n)!*n!) \text{ where } k=m+(n-1)$$

For example, the combinations of the four moieties labeled A, B, C, D which have 3 members are: A A A; A A B; A A C; A A D; A B B; A B C; A B D; A C C; A C D; A D D; B B B; B B C; B B D; B C C; B C D; B D D; C C C; C C D; C D D and D D D. B A A and A B A, for example, are not counted as separate combinations; only A A B is counted. In this example, m=4, n=3 and the number of combinations is given by $$6!/((6-3)!*3!)=20.$$

The terms "mass-coded set of compounds" and "mass-coded combinatorial library", as used herein, refer to a set of compounds of the formula $XY_n$, where X is a scaffold, each Y is, independently, a peripheral moiety and n is an integer greater than 1, typically from 2 to about 6. Such a set of compounds is synthesized as a mixture by the combination of a set of peripheral moiety precursors with a scaffold precursor, and is designed to possess minimum mass redundancy, given the requirement that a fixed number (subset) of peripheral moiety precursors must be chosen from a set of available peripheral moiety precursors.

The term "mass" or "molecular mass", as used herein, refers to the exact mass of a molecule or collection of chemical moieties in which each atom is the most abundant naturally occurring isotope for the particular element. Exact masses and their determination by mass spectrometry are discussed by Pretsch et al., *Tables of Spectral Data for Structure Determination of Organic Compounds,* second edition, Springer-Verlag (1989), and Holden et al., *Pure Appl. Chem.* 55:1119-1136 (1983), the contents of each of which are incorporated herein by reference in their entirety.

"Minimum mass redundancy", as the term is used herein, is exhibited by a set of compounds of the formula $X(Y)_n$ formed by reaction of a scaffold precursor having n reactive groups, where n is an integer greater than 1, typically from 2 to about 6, with a subset of peripheral moiety precursors in which at least about 90% of the possible combinations of n peripheral moieties derived from the subset of peripheral moiety precursors have a molecular mass sum which is distinct from the molecular mass sum of any other combination of n peripheral moieties derived from the subset. The molecular mass sum of a combination of peripheral moieties is the sum of the masses of each peripheral moiety within the combination. For the present purposes, two molecular masses are distinct if they can be distinguished by mass spectrometry or high resolution mass spectrometry. For example, molecular masses which differ by at least 0.001 atomic mass units can be distinguished by high resolution mass spectrometry.

It is to be understood that the molecular mass sum of the combination of the n peripheral moieties in a particular compound of the formula $X(Y)_n$ is the collective contribution of the n peripheral moieties to the molecular mass of the compound. As each compound within the set includes a constant scaffold, the difference in the molecular masses of two compounds within the mass-coded set of compounds is the difference in the molecular mass sums of the set of peripheral moieties in each compound.

The method of the invention comprises selecting a peripheral moiety precursor subset from a larger peripheral moiety precursor set. Details of the preferred selection process are discussed later with reference to FIGS. 1A, 1B and 3. The subset includes a sufficient number of peripheral moiety precursors so that, in one embodiment, at least about 50 distinct combinations of n peripheral moieties derived from the peripheral moiety precursors in the subset can be formed. In another embodiment, at least about 100 distinct combinations of n peripheral moieties can be formed. In a further embodiment, at least about 250 distinct combinations of n peripheral moiety precursors can be formed, and, in yet another embodiment, at least about 500 distinct combinations of n peripheral moieties can be formed.

The subset of peripheral moiety precursors is selected so that at least about 90% of all possible combinations of n peripheral moieties derived from the subset have a molecular mass sum which is distinct from the molecular mass sums of all of the other combinations of n peripheral moieties. The method further comprises contacting the peripheral moiety precursor subset with a scaffold precursor which has n reactive groups, each of which is capable of reacting with at least one peripheral moiety precursor to form a covalent bond. The peripheral moiety precursor subset is contacted with the scaffold precursor under conditions sufficient for the reaction of each reactive group with a peripheral moiety precursor, resulting in a mass-coded set of compounds.

In one embodiment, at least about 95% of all possible combinations of n peripheral moieties derived from the peripheral moiety precursor subset have a molecular mass sum which is distinct from the molecular mass sums of all of the other combinations of n peripheral moieties. In another embodiment, each of the possible combinations of n peripheral moieties derived from the subset has a molecular mass sum which is distinct from the molecular mass sums of all of the other combinations of n peripheral moieties.

The scaffold precursor can be any molecule comprising two or more reactive groups which are capable of reacting with a peripheral moiety precursor reactive group to form a covalent bond. For example, suitable scaffold precursors can have a wide range of sizes, shapes, degrees of flexibility and charges. The reactive groups should be incapable of intramolecular reaction under the conditions employed. Further, a scaffold precursor molecule should not react with another scaffold precursor molecule under the conditions employed. The scaffold precursor can also include any additional functional groups which are masked or protected or which do not interfere with the reaction of the reactive groups with the peripheral moiety precursors.

Preferably, the scaffold precursor comprises one or more saturated, partially unsaturated or aromatic cyclic groups, such as a cyclic hydrocarbon or heterocyclic group. In scaffold precursors comprising two or more cyclic groups, the cyclic groups can be fused, connected via a direct bond or connected via an intervening group, such as an oxygen atom, an NH group or a $C_{1-6}$-alkylene group. At least one cyclic group is substituted by one or more reactive groups. The reactive groups can be attached to the cyclic group directly or via an intervening group, such as a $C_{1-6}$-alkylene group, preferably a methylene group.

Examples of suitable scaffold precursors include reactive group-substituted benzene, biphenyl, cyclohexane, bipyridyl, N-phenylpyrrole, diphenyl ether, naphthalene and benzophenone. Other suitable classes of scaffold precursors are shown below.

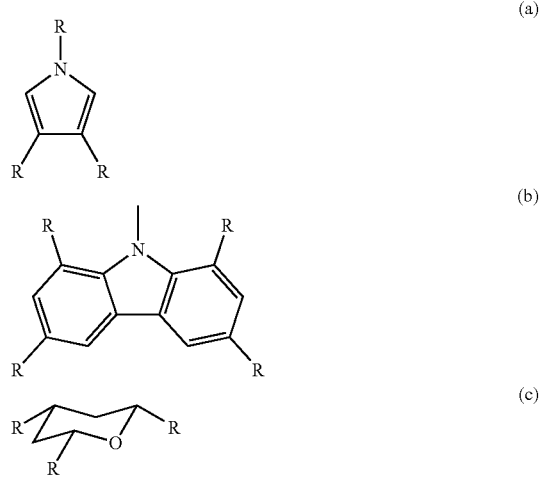

-continued

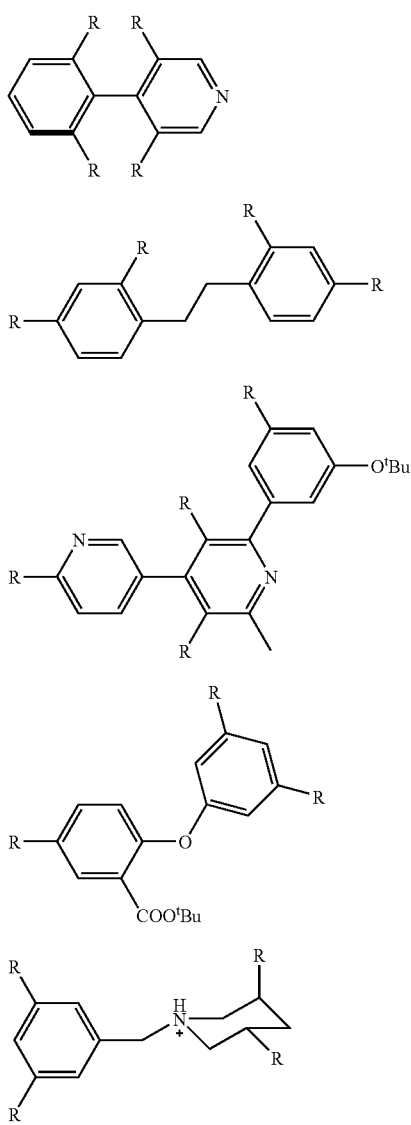

In these examples, each of the indicated substituents R is, independently, a reactive group, and the scaffold precursor can include one or more additional functional groups which are either (1) masked or protected to prevent their reaction with a peripheral moiety precursor (e.g., scaffold precursors f and g, above) or (2) do not react either with R or with a peripheral moiety precursor under the given reaction conditions (e.g., scaffold precursor h, above, in which R=C(O)O($C_6F_5$) and the peripheral moiety precursors include primary amino groups).

A peripheral moiety precursor is a compound which includes a reactive group which is complementary to one or more of the reactive groups of the scaffold precursor. In addition to the reactive group, a peripheral moiety precursor can include a wide variety of structural features. For example, the peripheral moiety precursor can include one or more functional groups in addition to the reactive group. Any additional functional group should be appropriately masked or not interfere with the reaction between the scaffold precursor and the peripheral moiety precursor. In addition, two peripheral moiety precursors should not react together under the conditions employed. For example, a subset of peripheral moiety precursors can include, in addition to the reactive groups, functionalities selected from groups spanning a range of charge, hydrophobicity/hydrophilicity, and sizes. For example, the peripheral moiety precursor can include a negative charge, a positive charge, a hydrophilic group or a hydrophobic group.

In addition to the reactive groups, peripheral moiety precursors can include, for example, functionalities selected from among amino acid side chains, a nucleotide base or nucleotide base analogue, sugar moieties, sulfonamides, peptidomimetic groups, charged or polar functional groups, alkyl groups and aryl groups.

For the present purposes, two reactive groups are complementary if they are capable of reacting together to form a covalent bond. In a preferred embodiment, the bond forming reactions occur rapidly under ambient conditions without substantial formation of side products. Preferably, a given reactive group will react with a given complementary reactive group exactly once.

In one embodiment, the reactive group of the scaffold precursor and the reactive group of the peripheral moiety precursor react, for example, via nucleophilic substitution, to form a covalent bond. In one embodiment, the reactive group of the scaffold precursor is an electrophilic group and the reactive group of the peripheral moiety precursor is a nucleophilic group. In another embodiment, the reactive group of the scaffold precursor is a nucleophilic group, while the reactive group of the peripheral moiety precursor is an electrophilic group.

Complementary electrophilic and nucleophilic groups include any two groups which react via nucleophilic substitution under suitable conditions to form a covalent bond. A variety of suitable bond-forming reactions are known in the art. See, for example, March, *Advanced Organic Chemistry*, fourth edition, New York: John Wiley and Sons (1992), Chapters 10 to 16; Carey and Sundberg, *Advanced, Organic Chemistry*, Part B, Plenum (1990), Chapters 1-11; and Collman et al., *Principles and Applications of Organotransition Metal Chemistry*, University Science Books, Mill Valley, Calif. (1987), Chapters 13 to 20; each of which is incorporated herein by reference in its entirety. Examples of suitable electrophilic groups include reactive carbonyl groups, such as carbonyl chloride (acyl chloride) and carbonyl pentafluorophenyl ester groups, reactive sulfonyl groups, such as the sulfonyl chloride group, and reactive phosphonyl groups. Other electrophilic groups which can be used include terminal epoxide groups and the isocyanate group. Suitable nucleophilic groups include primary and secondary amino groups and alcohol (hydroxyl) groups.

Examples of suitable scaffold precursors with specified reactive groups are shown below.

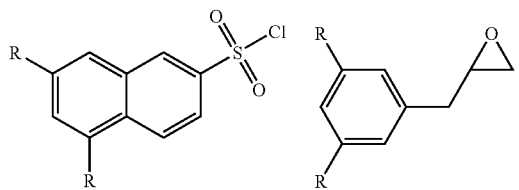

-continued

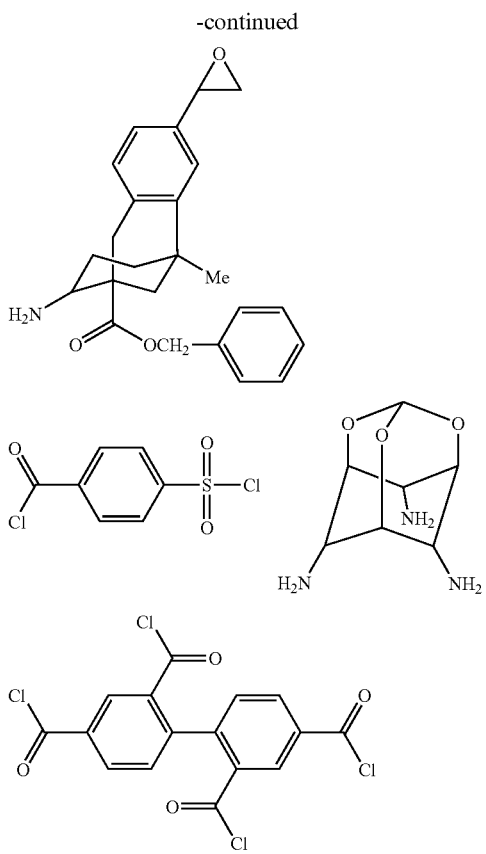

In these examples, each R is, independently, an additional reactive group which can be the same as the specified reactive group or a different group.

Illustrated below are examples of suitable peripheral moiety precursors having amino groups.

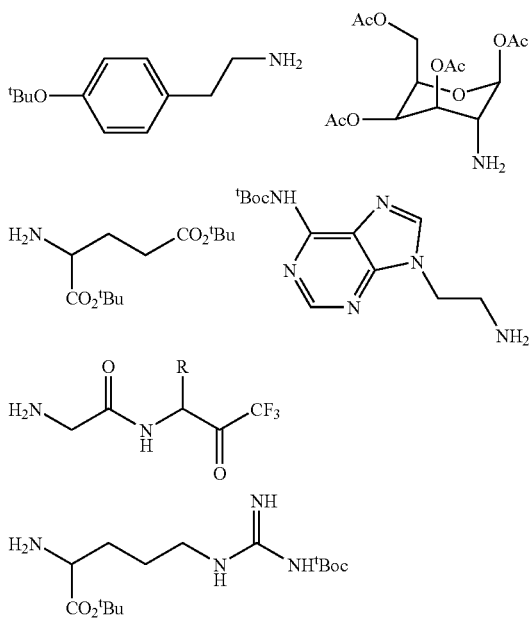

-continued

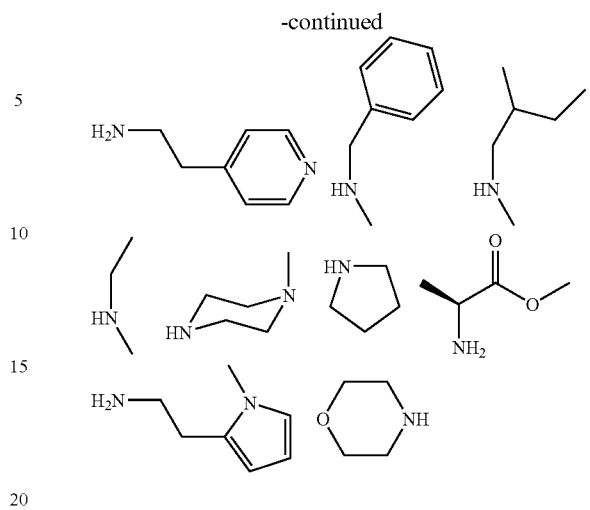

R in this case is an amino acid side chain, $^t$Boc is $^t$butoxycarbonyl, Ac is acetyl and $^t$Bu is tertiary butyl.

Examples of scaffold precursors and peripheral moiety precursors which have complementary reactive groups include the following, which are provided for the purposes of illustration and are not to be construed as limiting in any way:

1. The scaffold precursor includes from two to about six reactive carbonyl groups, reactive sulfonyl groups or reactive phosphonyl groups, or a combination thereof. Each peripheral moiety precursor includes a primary or secondary amino group which reacts with the scaffold precursor to form an amide, sulfonamide or phosphonamidate bond.
2. The scaffold precursor includes from two to about six primary or secondary amino groups or a combination thereof. Each peripheral moiety precursor includes a reactive carbonyl group, a reactive sulfonyl group or a reactive phosphonyl group.
3. The scaffold precursor includes from two to about six terminal epoxide groups. Each peripheral moiety precursor includes a primary or secondary amino group. In the presence of a suitable Lewis acid, the scaffold precursor and the peripheral moiety precursors react to form F-amino alcohols.
4. The scaffold precursor includes from two to about six primary or secondary amino groups. Each peripheral moiety precursor contains a terminal epoxide group.
5. The scaffold precursor includes from two to about six isocyanate groups. Each peripheral moiety precursor contains a primary or secondary amino group which reacts with the scaffold precursor to form a urea.
6. The scaffold precursor includes from two to about six primary or secondary amino groups, or a combination thereof. Each peripheral moiety precursor contains an isocyanate group.
7. The scaffold precursor includes from two to about six isocyanate groups. Each peripheral moiety precursor contains an alcohol group which reacts with the scaffold precursor to form a carbamate.
8. The scaffold precursor includes from 2 to about 6 aromatic bromides. Each peripheral moiety precursor is an organo-tributyl-tin compound. The scaffold precursor and the peripheral moiety precursors are reacted in the presence of a suitable palladium catalyst to form one or more carbon-carbon bonds.

9. The scaffold precursor includes from 2 to about 6 aromatic halides or triflates. Each peripheral moiety precursor includes a primary or secondary amino groups. The scaffold precursor and the peripheral moiety precursors are reacted in the presence of a suitable palladium catalyst to form one or more carbon-nitrogen bonds.
10. The scaffold precursor includes from two to about six amino groups. Each peripheral moiety precursor contains an aldehyde or ketone group which reacts with the scaffold precursor under reducing conditions (reductive amination) to form an amine.
11. The scaffold precursor includes from two to about six aldehyde or ketone groups. Each peripheral moiety precursor contains an amino group which reacts with the scaffold precursor under reducing conditions (reductive amination) to form an amine.
12. The scaffold precursor includes from two to about six phosphorous ylide groups. Each peripheral moiety precursor contains an aldehyde or ketone group which reacts with the scaffold precursor (Wittig type reaction) to form an alkene.
13. The scaffold precursor includes from two to about six aldehyde or ketone groups. Each peripheral moiety precursor contains a phosphorous ylide group which reacts with the scaffold precursor (Wittig type reaction) to form an alkene.

The scaffold is that portion of the scaffold precursor which remains after each reactive group of the scaffold precursor has reacted with a peripheral moiety precursor. A peripheral moiety is that portion of the peripheral moiety precursor which is bonded to the scaffold following the bond-forming reaction. A peripheral moiety which results from the reaction of a particular peripheral moiety precursor with a reactive functional group of a scaffold precursor is said to be "derived" from that peripheral moiety precursor.

A peripheral moiety precursor can include one or more functional groups in addition to the reactive group. One or more of these additional functional groups can be protected to prevent undesired reactions of these functional groups. Suitable protecting groups are known in the art for a variety of functional groups (Greene and Wuts, *Protective Groups in Organic Synthesis,* second edition, New York: John Wiley and Sons (1991), incorporated herein by reference). Particularly useful protecting groups include t-butyl esters and ethers, acetals, trityl ethers and amines, acetyl esters, trimethylsilyl ethers and trichloroethyl ethers and esters.

Figure 3:
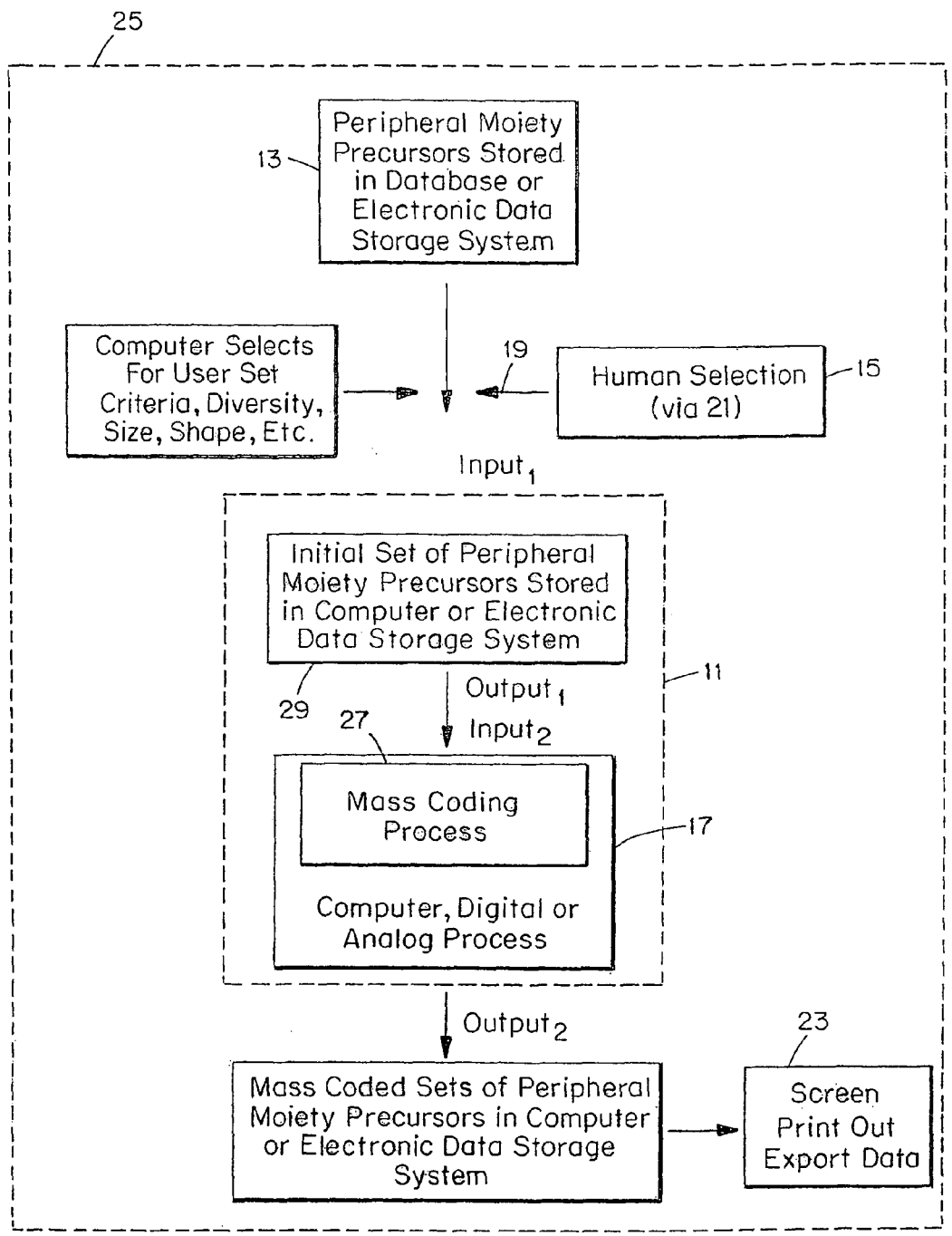
FIG. 3 is a schematic diagram of a computer system employing a digital processor assembly embodying the invention method of selecting a subset of peripheral moiety precursors which minimize or eliminate mass redundancy in a library.

The compounds within the set are mass-coded as a result of the selection of a subset of suitable peripheral moiety precursors. The subset of peripheral moiety precursors is selected such that for a scaffold precursor having n reactive groups, where n is an integer from 2 to about 6, there exist at least about 50, 100, 250 or 500 different combinations of n peripheral moieties derived from the peripheral moiety precursor subset. At least about 90% of the possible combinations of n peripheral moieties derived from the peripheral moiety precursors within the subset will have a distinct mass sum. In one embodiment, the selection of suitable peripheral moiety precursors for the production of a mass-coded set of compounds includes one or more automated steps utilizing hardware apparatus, software apparatus or any combination thereof. In the preferred embodiment, a digital processor assembly employs a suitable software routine which selects a subset of peripheral moiety precursors which minimize or eliminate mass redundancy in the library. FIG. 3 is illustrative of such apparatus employing a digital processor assembly for carrying out the present invention method.

Referring to FIG. 3, there is shown a computer system 25 formed of (a) a digital processor 11 having working memory 17 for executing programs, routines, procedures and the like, (b) input means 21 coupled to the digital processor 11 for providing data, parameters and the like to support execution of the programs, routines and/or procedures in the digital processor working memory 17, and (c) output means 23 coupled to the digital processor 11 for displaying results, prompts, messages and the like from operation of the digital processor 11. The input means 21 include a keyboard, mouse and the like common in the art. The output means 23 include a viewing monitor, printer and the like common in the art. The invention software routine 27 is executed in the working memory 17 by the digital processor 11 as follows.

First, a user interface prompts the end-user to input indications of an initial set 13 of peripheral moiety precursors and the exact masses of the peripheral moieties which are derived therefrom. This initial set 13 may be copied, transferred or otherwise obtained from a database or other source such as is known in the art. The user interface also obtains from the end-user a set of user determined/desired criteria 19. In the preferred embodiment, the user selected criteria 19 includes (i) the total count j of peripheral moiety precursors in the initial set, (ii) the value of n indicating the number of reactive groups of a subject scaffold precursor for which the invention software routine 27 is to select a subset of peripheral moiety precursors from the input initial set 13 and (iii) the number of members of the subset, k. Preferably, the user interface enables the end-user to interactively provide the user selected criteria 19 through the input means 21 as indicated at 15 in FIG. 3.

The digital processor 11 is responsive to the foregoing input and stores the indications of the initial set 13 of peripheral moiety precursors in a memory area 29 or data storage system associated locally or off disk with the software routine 27. That is, the memory area 29 or data storage system supports the invention software routine 27. For each peripheral moiety precursor in the initial set 13 as indicated in memory area 29, an identifier and indication of respective exact mass of the the peripheral moiety derived from the peripheral moiety precursor is provided to the software routine 27. Upon receipt of the peripheral moiety precursor identifiers, indications of exact mass, and user selected criteria (n, j and k), the software routine 27 determines and generates a subset of k peripheral moiety precursors which minimize or eliminate mass redundancy in a resulting library of compounds of the formula $XY_n$, wherein X is a scaffold, each Y is, independently, a peripheral moiety, and n is an integer greater than 1, typically from 2 to about 6. Preferably, the software routine 27 determines a subset of peripheral moiety precursors in which at least about 90% of the possible combinations of n peripheral moieties derived from the subset have a distinct mass sum. The details of the software routine 27 employed in the preferred embodiment are discussed next for purposes of illustration and not limitation. It is understood that other software or firmware routines for accomplishing the present invention method of selecting a subset of the initial set 13 of peripheral moiety precursors are suitable and within the purview of one skilled in the art given this disclosure.

A typical situation involves a scaffold precursor with n reactive groups, where n is an integer, a set of j peripheral moiety precursors, where j is an integer 6 or greater, where the peripheral moieties derived from the peripheral moiety precursors have molecular masses $y_1, y_2, \ldots y_j$. An example of a software routine which can be employed to select a suitable subset of k peripheral moiety precursors (k≦j) from the set of j peripheral moiety precursors includes the following steps:
1. From an initial set of j peripheral moiety precursors, choose every set of two peripheral moiety precursors. If $y_a=y_b$, randomly remove either $y_a$ or $y_b$.
2. From the remaining set of peripheral moiety precursors, choose every set of four peripheral moiety-precursors. If $y_a+y_b=y_c+y_d$, randomly remove either $y_a$, $y_b$, $y_c$ or $y_d$.
3. From the remaining set of peripheral moiety precursors, choose every set of six peripheral moiety precursors. If $y_a+y_b+y_c=y_d+y_e+y_f$, randomly remove either $y_a$, $y_b$, $y_c$, $y_d$, $y_e$ or $y_f$.
If at any step 1 through 3 the remaining number of peripheral moiety precursors becomes <k, then there is no mass coded subset k which can be made from set j, and a new set j must be employed.
4. From the remaining computer selected set of peripheral moiety precursors, choose any or all subsets of k peripheral moiety precursors.
5. Generate all possible combinations of n peripheral moiety precursors from this subset.
6. If the % mass redundancy of the resulting set of combinations is found to be unacceptable, repeat step 5 until a desired mass coded library has been obtained or no further possible combinations of peripheral moiety precursors remain. In the latter case, begin again with step 1.

Once an above subset of mass-coded peripheral moiety precursors is determined, the scaffold precursor is contacted with the subset of complementary peripheral moiety precursors under conditions suitable for bond-forming reactions to occur between the peripheral moiety precursors and the scaffold precursor. The mass-coded set of compounds is, preferably, synthesized in solution as a combinatorial library.

Figure 1B:
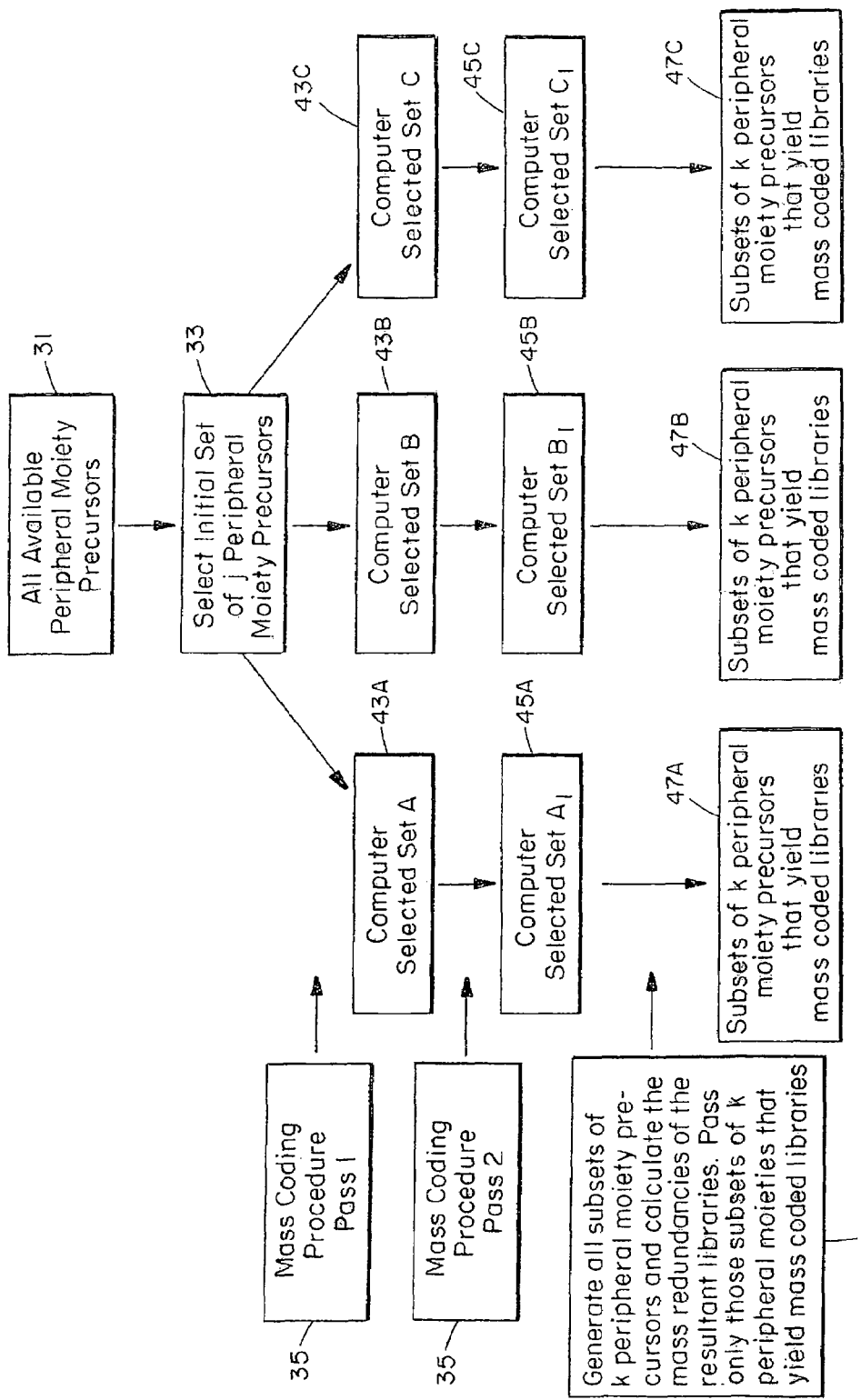

The foregoing selection of a subset from a larger peripheral moiety precursor set and generation of a mass-coded set of compounds using the selected subset is more generally illustrated in FIGS. 1A and 1B. Referring to FIG. 1A, the larger set of peripheral moiety precursors is provided at 31 from known sources. The end-user (e.g., chemist) selects an initial set of j peripheral moiety precursors from the larger set 31 at step 33. Typically the chemist chooses all of the larger set to form the initial set at 33. The invention mass coding selection procedure 35 is applied to the initial set. The result of the mass-coding procedure 35 is a subset 37 of peripheral moiety precursors that satisfies the mass-coding criteria outlined above. In step 39, this subset of peripheral moiety precursors is used to generate all theoretical subsets of of k peripheral moiety precursors. Also in step 39, the mass redundancies of the libraries obtained from all theoretical subsets of k peripheral moieties are calculated, and only those subsets which yield mass-coded libraries, as defined above, are passed to 41. The net result is one or more subsets 41 of k peripheral moiety precursors in which there are 50, 100, 250, or 500 distinct combinations of n peripheral moiety precursors in a given subset and at least 90% of all possible combinations of n peripheral moieties derived from a given subset have a molecular mass sum which is distinct from the molecular mass sums of all of the other combinations of n peripheral moieties, as discussed above. The subset(s) 41 of peripheral moiety precursors would subsequently yield mass-coded sets of compounds when contacted with an appropriate scaffold precursor in the manner discussed above.

As an alternative to the single-step application of the invention mass-coding selection procedure 35 in FIG. 1A, multiple or stepped application of procedure 35 is suitable and in certain cases may be advantageous. For instance, using mass-coding procedures at each level allows for rapid sorting into distinct sets, each of which may yield optimal mass-coding. During the mass-coding process, certain criteria reduce the set size as it is passed into the next layer through mass-coding. This multi-layer approach yields advantages in speed and the elimination of mass redundancy.

Multiple application of mass-coding selection procedure 35 on initial set 33 is illustrated in FIG. 1B. Here initial set 33 is divided into plural parts (the starting larger set of peripheral moiety precursors 31 and chemist selection 33 being similar to that in FIG. 1A) The mass-coding selection procedure 35 is applied to each plural part and results in intermediate resultant sets 43A, 43B, 43C. The mass-coded selection procedure 35 is applied in a second round/level, but this time with intermediate resultant sets 43A, 43B, 43C. This produces final sets 45A, 45B, 45C. Step 39 is as in FIG. 1A and generates the subsets 47A, 47B, 47C of k peripheral moiety precursors that would subsequently yield mass-coded stes of compounds when contacted with an appropriate scaffold precursor in a manner discussed above.

It is understood that other variations between the approach illustrated in FIG. 1A and that in FIG. 1B are within the purview of one skilled in the art. The foregoing discussion and Figures are for purposes of illustrating and not limiting the present invention method.

In one embodiment, the scaffold precursor is contacted with all members of the peripheral moiety precursor subset simultaneously. In general, a scaffold precursor having n reactive groups, where n is an integer from 2 to about 6, will be contacted with at least about n molar equivalents relative to the scaffold precursor of peripheral moiety precursors from the selected subset. For example, the scaffold precursor can be contacted with a solution comprising each member of the subset in approximately equal concentrations. For example, if the scaffold precursor includes n reactive groups, where n is an integer greater than 1, and the number of peripheral moiety precursors in the subset is denoted by p, the scaffold precursor can be contacted with about n/p to about (1.1)n/p molar equivalents of each peripheral moiety precursor.

In another embodiment, the scaffold precursor is contacted with the members of the peripheral moiety precursor subset sequentially. This results in the formation of intermediate partially reacted scaffold precursor molecules which include at least one peripheral moiety and at least one reactive group. For example, the scaffold precursor can be contacted with one or more peripheral moiety precursors under conditions suitable for bond formation to occur. The resulting intermediates can then be contacted with one or more additional peripheral moiety precursors under suitable conditions for bond formation to occur. These steps can be repeated until each scaffold precursor reactive group has reacted with a peripheral moiety precursor.

In one embodiment, the reactive groups of the scaffold precursor can react sequentially with the subset of peripheral moiety precursors using a suitable reactive group protection/deprotection scheme. For example, the scaffold precursor can include two or more sets of reactive groups, where one set is unprotected and another set is protected, or where two sets are masked by different protecting groups. An example is the use of the scaffold precursor

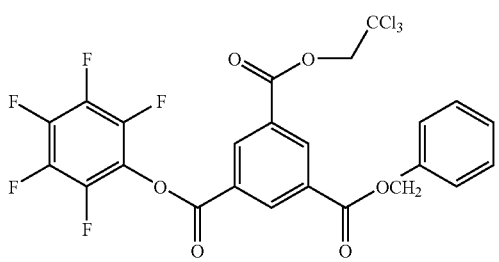

which contains one unprotected reactive group and two protected reactive groups. In this case, the unprotected pentafluorophenyl ester can react with a peripheral moiety precursor first (e.g., a primary amine). Either the Cl₃CCH₂O-protected group or the benzyloxy-protected group can then be deprotected using standard methods and reacted with a set of peripheral moiety precursors. Finally, the remaining protected group or groups can be deprotected and reacted with a set of peripheral moiety precursors.

Following the reaction of each scaffold precursor reactive group with a peripheral moiety precursor, any peripheral moiety having a protected functional group can be deprotected using methods known in the art.

The ability to identify individual scaffold plus peripheral moiety combinations derived from such a mixture is a consequence of the mass-coding of the library and the ability of mass spectrometry to identify a molecular mass. This allows the identification of individual scaffold plus peripheral moiety combinations within the set which have a particular activity, such as binding to a particular biomolecule.

In one embodiment, the present invention provides a method for identifying a compound or compounds within a mass-coded combinatorial library which bind to, or are ligands for, a biomolecule, such as a protein or nucleic acid molecule. The mass-coded combinatorial library can be produced, for example, by the method of the invention disclosed above. The target biomolecule, such as a protein, is contacted with the mass-coded combinatorial library, and, if any members of the library are ligands for the biomolecule, biomolecule-ligand complexes form. Compounds which do not bind the biomolecule are separated from the biomolecule-ligand complexes. The biomolecule-ligand complexes are dissociated and the ligands are separated and their molecular masses are determined. Due to the mass-coding of the combinatorial library, a given molecular mass is characteristic of a unique combination of peripheral moieties or only a small number of such combinations. Thus, a ligand's molecular mass allows the determination of its composition.

In one embodiment, the target is immobilized on a solid support by any known immobilization technique. The solid support can be, for example, a water-insoluble matrix contained within a chromatography column or a membrane. The mass-coded set of compounds can be applied to a water-insoluble matrix contained within a chromatography column. The column is then washed to remove non-specific binders. Target-bound compounds (ligands) can then be dissociated by changing the pH, salt concentration, organic solvent concentration, or other methods, such as competition with a known ligand to the target. The dissociated ligands are injected directly onto a reverse phase column. The reverse phase column acts as a concentrator/collector and can be interfaced directly to a mass spectrometer, such as an electrospray mass spectrometer (ES-MS) Mass information provided by the mass spectrometer is sufficient for identifying the combination of scaffold and peripheral moieties within the ligand.

In another embodiment, the target is free in solution and is incubated with the mass-coded set of compounds. Compounds which bind to the target (ligands) are selectively isolated by a size separation step such as gel filtration or ultrafiltration. In one embodiment, the mixture of mass-coded compounds and the target biomolecule are passed through a size exclusion chromatography column (gel filtration), which separates any ligand-target complexes from the unbound compounds. The ligand-target complexes are transferred to a reverse-phase chromatography column, which dissociates the ligands from the target. The dissociated ligands are then analyzed by mass spectrometry. Mass information provided by the mass spectrometer is sufficient for identifying the scaffold and peripheral moiety composition of the ligand. This approach is particularly advantageous in situations where immobilization of the target may result in a loss of activity.

Once single ligands are identified by the above-described process, various levels of analysis can be applied to yield SAR information and to guide further optimization of the affinity, specificity and bioactivity of the ligand. For ligands derived from the same scaffold, three-dimensional molecular modeling can be employed to identify significant structural features common to the ligands, thereby generating families of small-molecule ligands that presumably bind at a common site on the target biomolecule.

In order to identify a consensus, highest affinity, ligand for a particular binding site, this analysis should include a ranking of the members of a given ligand family with respect to their affinities for the target. This process can provide this information by identifying both low and high affinity ligands for a target biomolecule in one experiment. For example, when the screen utilizes an immobilized target, the dissociation rate of the ligand is inversely correlated with the number of column volumes employed during of the ligand from its target. When the screen utilizes the target free in solution, weak affinity ligands can be selected by using a higher concentration of the target.

Given that each mass-coded set of compounds is synthesized with a limited number of peripheral moiety precursors, the disclosed approach can, in certain cases, identify a superior ligand which combines structural features of molecules synthesized in separate libraries.

When possible, the analysis of ligand structural features is based on information regarding the target biomolecule's structure, wherein the hypothetical consensus ligand is computationally docked with the putative binding site. Further computational analysis can involve a dynamic search of multiple lowest energy conformations, which allows comparison of high affinity ligands that are derived from different scaffolds. The end goal is the identification of both the optimal functionality and the optimal vectorial presentation of the peripheral moieties that yields the highest binding affinity/specificity. This may provide the basis for the synthesis of an improved, second-generation scaffold.

Due to the modular design of the mass-coded compounds, computational analysis may identify the point of attachment on the scaffold that has the least functional importance with respect to affinity for the target. In many cases, the ligand will not be completely engulfed by the target biomolecule, and one peripheral moiety will be pointed away from the biomolecule towards the bulk solvent. Three-dimensional alignment of a family of ligands will reveal a high degree of functional variability at the site that is presented to the solvent. Modification at this site can then be used to optimize the affinity. For example, the noncritical reactive site can be removed and replaced with a small unreactive group, such as a hydrogen atom or a methyl group. A set of compounds structurally identical except for the peripheral moiety at this position can be examined to identify compounds that most effectively inhibit or promote the binding of another protein/DNA/RNA molecule. Also, the peripheral moiety at this position can be modified to link two ligands together. The joining of two ligands could in certain cases yield a ligand with improved affinity and specificity, if one joins molecules that bind to adjacent sites, or yield a designed biomolecule dimerizer.

A variety of screening approaches can be used to obtain ligands that possess high affinity for one target but significantly weaker affinity for another closely related target. One screening strategy is to identify ligands for both biomolecules in parallel experiments and to subsequently eliminate common ligands by a cross-referencing comparison. In this method, ligands for each biomolecule can be separately identified as disclosed above. This method is compatible with both immobilized target biomolecules and target biomolecules free in solution.

For immobilized target biomolecules, another strategy is to add a preselection step that eliminates all ligands that bind to the non-target biomolecule from the library. For example, a first biomolecule can be contacted with a mass-coded combinatorial library as described above. Compounds which do not bond to the first biomolecule are then separated from any first biomolecule-ligand complexes which form. The second biomolecule is then contacted with the compounds which did not bind to the first biomolecule. Compounds which bind to the second biomolecule can be identified as described above and have significantly greater affinity for the second biomolecule than to the first biomolecule.

The screening approach detailed above can also be applied to identify ligands that selectively interact with an altered version of the same biomolecule, wherein the first biomolecule is the unaltered biomolecule and the second biomolecule is an altered or variant version of the biomolecule. The second biomolecule can, for example, have an amino acid sequence which differs from the amino acid sequence of the first biomolecule by the insertion, deletion or substitution of one or more amino acid residues. For example, the second biomolecule can include a specific amino acid mutation that is linked to the progression of a particular disease. Alternatively, the second biomolecule can also differ from the first biomolecule in having a different post-translational modification, such as an extra site of phosphorylation or glycosylation, or it may be truncated or aberrantly fused with another biomolecule.

The screening approach detailed above can also serve as a method for identifying small molecule ligands that bind at the same site on a biomolecule as another known, biologically relevant ligand. This known ligand can be another biomolecule, such as a protein or peptide, or it can be a DNA or RNA molecule, or a substrate or cofactor involved in an enzymatic reaction. In one embodiment, the first and second biomolecules are both proteins. The first protein is a complex of the protein and the known ligand, while the second protein is the protein alone. Compounds which bind to the protein alone, but not to the complex of the protein with the known ligand, bind to the protein at the binding site of the known ligand. This approach is especially well suited to the development of small molecule replacements of known therapeutic ligands, such as peptides or proteins.

An advantage of the present method is that it can be used to identify chemical compounds that bind tightly to any biomolecule of interest, even when the function of that biomolecule is not well understood, as is often the case with gene products defined through genomics, or when a functional assay is not available. The screening technologies described can be miniaturized to provide massive parallel screening capabilities.

A ligand for a biomolecule of unknown function which is identified by the method disclosed above can also be used to determine the biological function of the biomolecule. This is advantageous because although new gene sequences continue to be identified, the functions of the proteins encoded by these sequences and the validity of these proteins as targets for new drug discovery and development are difficult to determine and represent perhaps the most significant obstacle to applying genomic information to the treatment of disease. Target-specific ligands obtained through the process described in this invention can be effectively employed in whole cell biological assays or in appropriate animal models to understand both the function of the target protein and the validity of the target protein for therapeutic intervention. This approach can also confirm that the target is specifically amenable to small molecule drug discovery. The ligands obtained through the process described in this invention are small molecules and are, thus, similar to actual human therapeutics (small molecule drugs).

In one embodiment, a member of a combinatorial library is identified as a ligand for a particular biomolecule using the method described above. The ligand can then be assessed in an in vitro assay for the effect of the binding of the ligand to the biomolecule on the function of the biomolecule. For a biomolecule having a known function, the assay can include a comparison of the activity of the biomolecule in the presence and absence of the ligand. If the biomolecule is of unknown function, a cell which expresses the biomolecule can be contacted with the ligand and the effect of the ligand on the viability or function of the cell is assessed. The in vitro assay can be, for example, a cell death assay, a cell proliferation assay or a viral replication assay. For example, if the biomolecule is a protein expressed by a virus, the a cell infected with the virus can be contacted with a ligand for the protein. The affect of the binding of binding of the ligand to the protein on viral viability can then be assessed.

A ligand identified by the method of the invention can also be assessed in an in vivo model or in a human. For example, the ligand can be evaluated in an animal or organism which produces the biomolecule. Any resulting change in the health status (e.g., disease progression) of the animal or organism can be determined.

For a biomolecule, such as a protein or a nucleic acid molecule, of unknown function, the effect of a ligand which binds to the biomolecule on a cell or organism which produces the biomolecule can provide information regarding the biological function of the biomolecule. For example, the observation that a particular cellular process is inhibited in the presence of the ligand indicates that the process depends, at least in part, on the function of the biomolecule.

The mass-coded libraries provided by the present method enable the development of an information set that describes how the universe of small molecules interacts with any biomolecule encoded within the human and other genomes. This information set would include data regarding: 1) those libraries and components therein which bind to the target biomolecule, 2) quantitative structure-activity relationships (SAR) on chemical functionalities which contribute to the binding affinity of a compound for a biomolecule target, and 3) the domains of the biomolecule that are bound by chemical compounds. The database can be used to expedite drug development in a number of ways, for example, by identifying chemical pharmacophores that interact with high affinity with a specific drug binding site.

The invention will now be further and more specifically described in the following examples.

EXAMPLES

Example 1

Application of Mass-Coding by Computer Algorithms: Comparison of Mass-coded and Non-Mass-Coded Combinatorial Libraries The following is an analysis of the application of mass-coding algorithms towards the design of combinatorial libraries. The sequence of steps involved in identifying subsets of peripheral moiety precursors that can be allowed to react with a predetermined scaffold precursor to yield a mass-coded combinatorial library of compounds with the molecular formula $X(Y)_n$ is shown in FIG. 1A; FIG. 1B is an alternate sequence of steps. It is to be understood that the molecular mass sum of the combination of the n peripheral moieties in a particular compound of the formula $X(Y)_n$ is the collective contribution of the n peripheral moieties to the molecular mass of the compound. As each compound within the library includes a constant scaffold, the mass redundancy of the mass-coded library is equivalent to the molecular mass sum redundancy of all combinations of n peripheral moieties derived from the identified subset of peripheral moiety precursors.

The mass-coding analysis was performed on the initial set of 22 peripheral moieties shown below. This initial set was selected arbitrarily. Included were peripheral moiety precursors having the same exact mass. The master set consisted of the peripheral moiety precursors shown below, along with the exact masses of the resulting peripheral moieties. The molecular masses given are the exact molecular masses and not the isotope averages. The exact molecular masses are also adjusted for any atoms which are lost as a result of the reaction with the scaffold precursor (in this case the loss of a hydrogen atom). From the initial set of 22 peripheral moiety precursors, two sets of 16 peripheral moiety precursors were generated. One set was chosen by the computer using the mass coding algorithm described herein (computer selected set). The other set was randomly chosen.

From each set of 16 peripheral moiety precursors the computer generated every possible subset of 12 peripheral moiety precursors. These subsets were used to generate all combinations of peripheral moiety precursors taken 4 at a time (representing libraries synthesized with a scaffold precursor having four reactive groups, such as four pentafluorophenyl esters). This process yielded two sets of 16 peripheral moiety precursors containing 1820 subsets of 12 each. Theoretically, these subsets of 12 peripheral moiety precursors would each yield a library of 1365 compounds containing different peripheral moiety combinations when allowed to react simultaneously with an appropriate scaffold precursor containing four reactive groups ($15!/[(15-4)!*4!]=1365$). The computer sorted every precursor subset and checked for mass redundancy in the resultant libraries (in this example mass redundancies were checked to the second significant digit after the decimal point).

It is noteworthy that the mass coding algorithms and the mass redundancy check are both flexible in that it is possible to adjust the computational filter to check mass redundancy to any significant figure. This architecture for mass-coding allows for rapid automated mass-coding, insures that a significant portion of the libraries generated with the computer selected set have less than 10% redundancy, and includes parameters for peripheral moiety precursor selection outside of exact mass. The computational requirements for this selection are fairly significant. The mass-coding algorithms are essential because it is computationally intractable to brute force calculate and check every possible set of peripheral moiety precursors from a master set of 60 or more peripheral moiety precursors.

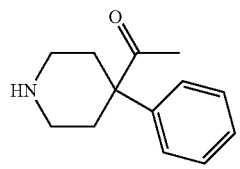

1a 202.1232

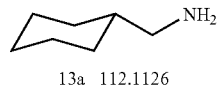

13a 112.1126

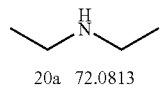

20a 72.0813

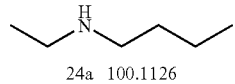

24a 100.1126

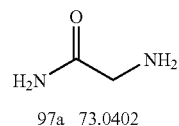

97a 73.0402

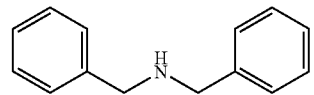

19a 196.1126

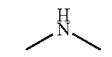

21a 44.0500

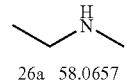

26a 58.0657

-continued

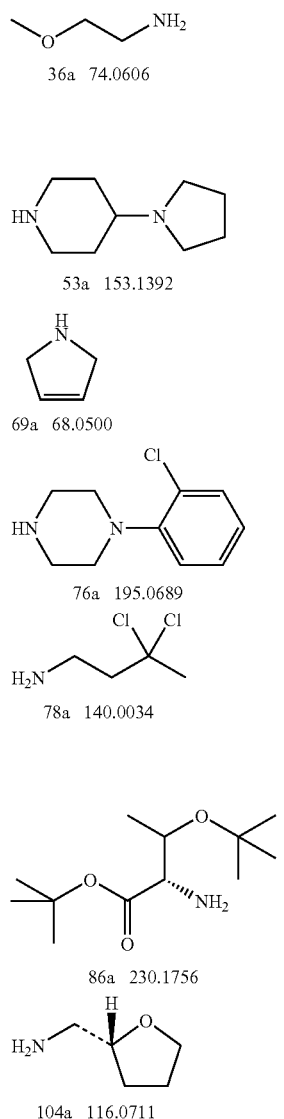
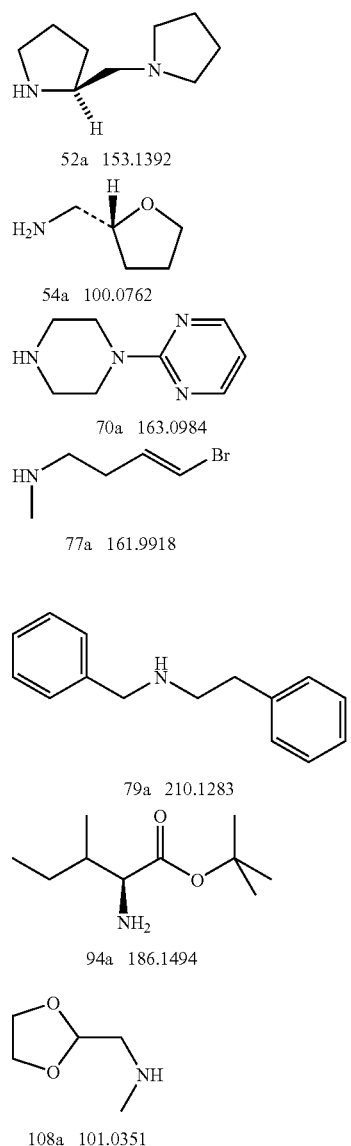

Results

Figure 2A:
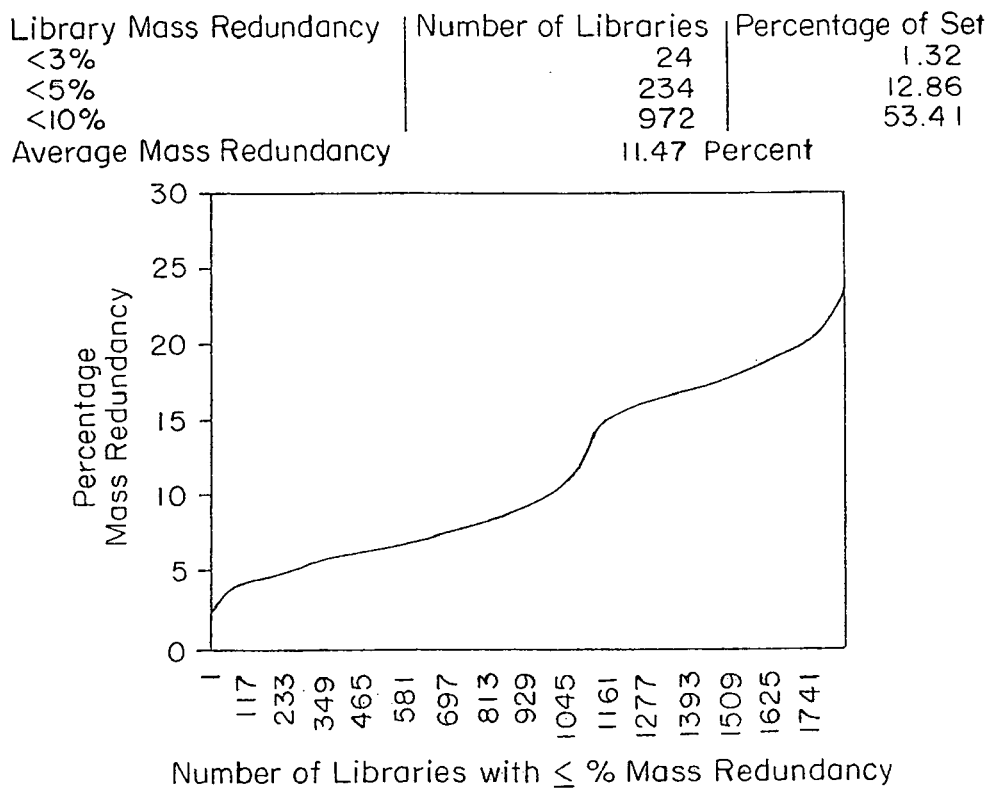
FIG. 2A is a graph illustrating the mass redundancy of the combinatorial libraries resulting from a computer selected set of peripheral moiety precursors selected using a mass-coding algorithm.
Figure 2B:
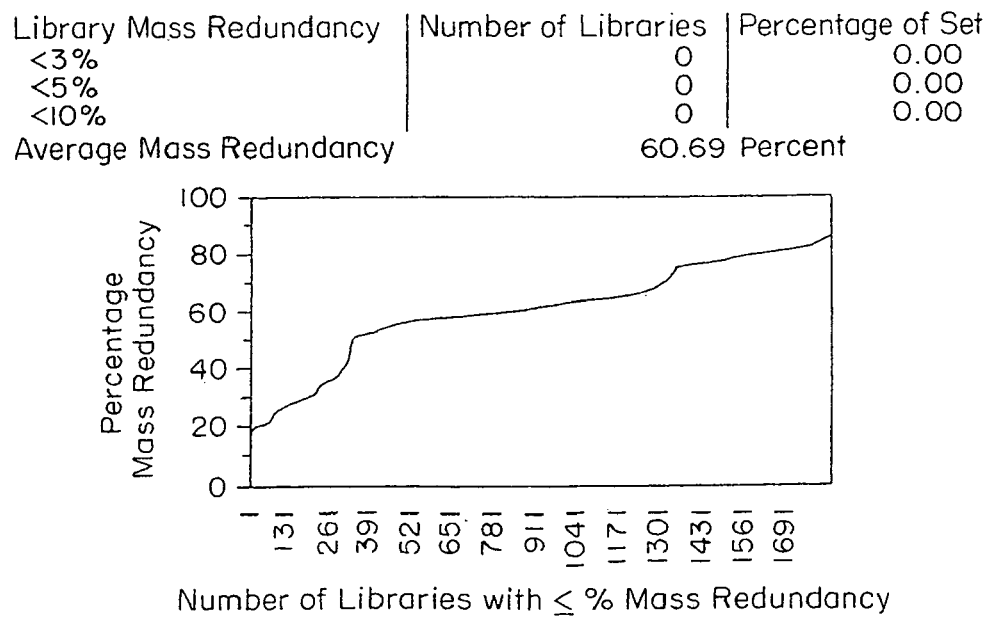
FIG. 2B is a graph illustrating the mass redundancy of the combinatorial libraries resulting from a set of peripheral moiety precursors selected randomly.
Figure 2C:
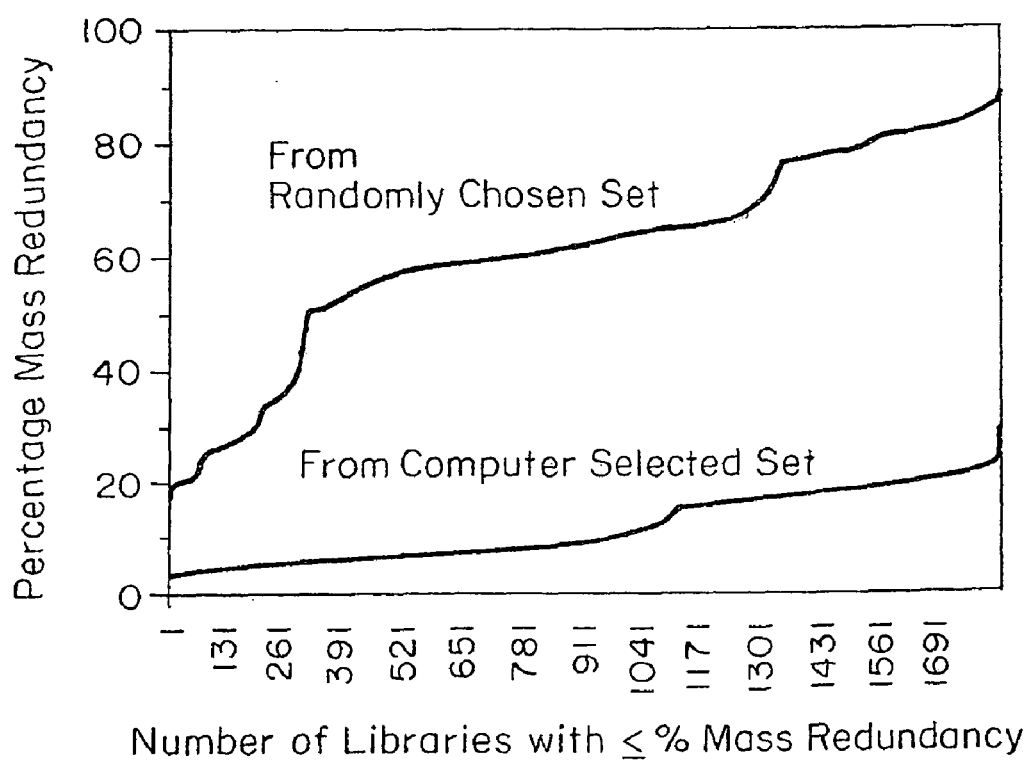
FIG. 2C presents graphs illustrating the mass redundancy of the combinatorial libraries resulting from (1) a computer optimized set of peripheral moiety precursors selected using a mass-coding algorithm ( . . . ) and (2) a set of peripheral moiety precursors selected randomly (-).

The computer selected set of 16 peripheral moiety precursors contained 86a, 79a, 13a, 108a, 76a, 20a, 69a, 1a, 70a, 26a, 24a, 36a, 97a, 94a, 104a, and 21a. The set of 16 randomly chosen peripheral moiety precursors contained 79a, 13a, 20a, 69a, 1a, 26a, 24a, 104a; 52a, 54a, 19a, 77a, 53a, 21a, 55a, 36a. The libraries generated from the computer selected set of peripheral moiety precursors had an average mass redundancy of 11.5% per library with 234 libraries having mass redundancies of less than 5% and 972 libraries having mass redundancies of less than 10% (FIG. 2A). The libraries generated from the randomly chosen set of peripheral moiety precursors had an average mass redundancy of 60.7% with no libraries having a mass redundancy of less than 10% (FIG. 2B). A direct graphical comparison of the mass redundancies of the two sets of libraries is shown in FIG. 2C. The libraries derived from the computer-selected set of peripheral moiety precursors and the corresponding mass redundancies are listed in the Table below.

Example 2

Development of Ligands for a Monofunctional Protein

A mass-coded combinatorial library can be used to identify ligands that have a high affinity for a monofunctional protein. One such monofunctional protein is the serine protease trypsin. Ligands that exhibit a high affinity for trypsin would be candidates to screen further for their ability to inhibit the proteolytic activity of trypsin. The identification of ligands to trypsin involves the following steps: trypsin is covalently biotinylated by incubation of the protein with a chemically activated biotin precursor. The biotin-trypsin conjugate is immobilized by binding to a streptavidin-derivatized water-insoluble column matrix. The mass-coded combinatorial library is solubilized in an appropriate binding buffer and injected onto a column containing the trypsin+streptavidin complex. Compounds that do not bind to the column are washed off with binding buffer. Compounds that bind to the column are dissociated by a change in the buffer conditions, such as a change in the pH or an increase in the percentage of organic solvent. These compounds are then loaded onto a reversed-phase column that is placed downstream of the trypsin+streptavidin column. The compounds are eluted from the reversed-phase column and analyzed by mass spectrometry. Molecular masses that correspond to ligands for trypsin are identified by eliminating those masses which are also observed when the library is similarly screened with a streptavidin column. The molecular mass of each trypsin ligand identifies one combination of peripheral moieties plus scaffold. The individual compound or compounds that result from the identified combination of peripheral moieties plus scaffold are synthesized and tested for their in vitro activity as inhibitors of trypsin.

Example 3

Development of Ligands for a Multifunctional Protein

Many proteins, especially human proteins, are multifunctional, and these functions are often mediated through interactions with multiple proteins. Ligands that bind to different sites on the protein might therefore yield different therapeutic results. The human protein HSP70 is one such example of a multifunctional protein. HSP70 has been shown to interact with multiple polypeptides, which are largely unfolded, to facilitate their translocation and folding. This role of HSP70 has been implicated in a variety of physiological processes, including antigen processing/presentation, development of certain cancers, and replication of a variety of human viruses. A mass-coded combinatorial library can be used to identify ligands that have a high affinity for HSP70 and bind at different sites. These ligands for HSP70 can be further evaluated in secondary assays to establish their effects on the immune response, cancer progression, and viral infection.

The identification of ligands to HSP70 involves the following steps: HSP70 is covalently biotinylated by incubation of the protein with a chemically activated biotin precursor. The biotin-HSP70 conjugate is immobilized by binding to a streptavidin-derivatized water-insoluble column matrix. The mass-coded library is solubilized in an appropriate binding buffer and injected onto a column containing the HSP70-streptavidin complex. Compounds that do not bind to the column are washed off with binding buffer. Compounds that bind to the column are dissociated by a change in the buffer conditions, such as a change in the pH or an increase in the percentage of organic solvent. Compounds that are dissociated from the column are loaded onto a reversed-phase column that is placed downstream of the HSP70-streptavidin column. Compounds are eluted from the reversed-phase column and analyzed by mass spectrometry. Masses that correspond to ligands for HSP70 are identified by eliminating those masses which are also observed when the library is similarly screened with a streptavidin column. The mass of each HSP70 ligand identifies one combination of peripheral moieties plus scaffold. The individual compound(s) that result from the identified combination of peripheral moieties plus scaffold are synthesized and tested for their in vivo ability to affect the immune response, cancer progression, and viral infection.

Example 3

Development of Ligands that Affect the Binding of a Known Ligand to a Protein

It is often the situation that a biologically important ligand is known for a target protein, but development of a high-throughput screen for molecules that modulate the binding of that ligand is not practical. For instance, it is known that HSP70 binds unfolded polypeptides in the presence of ADP, and that the binding of ATP to HSP70 leads to the dissociation of the polypeptide. Mass-coded combinatorial libraries can be used in the discovery of small molecule ligands that affect the binding of ATP, ADP, or unfolded peptides to HSP70, and one configuration is listed below: HSP70 is covalently biotinylated by incubation of the protein with a chemically activated biotin precursor. The biotin-HSP70 conjugate is immobilized by binding to a streptavidin-derivatized water-insoluble column matrix. The mass-coded library is solubilized in an appropriate binding buffer and injected onto a column containing the HSP70-streptavidin complex. Compounds that do not bind to the column are washed off with binding buffer. Compounds that bind to the column are dissociated upon addition of ATP, ADP, or ADP plus an unfolded peptide. Only compounds that bind to the same sites on HSP70 as these known ligands will be eluted under these conditions. Compounds that are dissociated from the column are loaded onto a reversed-phase column that is placed downstream of the HSP70-streptavidin column. Compounds are eluted from the reversed-phase column and analyzed by mass spectrometry. Masses that correspond to ligands for HSP70 are identified by eliminating those masses which are also observed when the library is similarly screened with a streptavidin column. The mass of each HSP70 ligand identifies one combination of peripheral moieties plus scaffold. The individual compound(s) that result from the identified combination of peripheral moieties plus scaffold are synthesized and tested in vitro for the ability to compete with these known ligands to HSP70 and for their in vivo ability to affect the immune response, cancer progression, and viral infection.

Example 4

Discovery of Small Molecule Replacements for Protein Therapeutics

In some instances, the known ligand to a target protein is in fact another protein, and the binding of these two proteins confers a therapeutic benefit. An example of such an interaction is the binding of granulocyte colony stimulating factor (G-CSF) to the G-CSF receptor (G-CSF-R). Replacement of G-CSF with a non-peptide small molecule can be undertaken using a mass-coded combinatorial library, and one approach is detailed below: in two separate and parallel experiments, the mass-coded library is solubilized in an appropriate binding buffer and incubated with either the G-CSF-R alone or the G-CSF-R plus G-CSF. Compounds that bind to the protein(s) are separated from the unbound compounds by rapid size exclusion chromatography. The binding compounds are loaded with the protein(s) onto a reversed-phase column that is placed downstream of the size exclusion column. The binding compounds are dissociated from the protein(s) and are eluted from the reversed-phase column and analyzed by mass spectrometry. Masses that correspond to compounds that bind to the G-CSF/G-CSF-R interface are identified as those masses which are only observed when the library is screened with G-CSF-R alone; masses which are also observed in the screen with the G-CSF/G-CSF-R complex are ignored. The mass of each interface-specific compound identifies one combination of peripheral moieties plus scaffold. The individual compound(s) that result from the identified combination of peripheral moieties plus scaffold are then synthesized and tested for their in vitro or in vivo ability to mimic G-CSF.

Example 5

Development of Small Molecules that Dimerize Two Proteins

Certain therapeutic proteins, such as erythropoietin (EPO), are multivalent and act by binding two molar equivalents of the target protein, thereby dimerizing the target protein, which, in the case of EPO is the EPO receptor (EPO-R). The protein replacement strategy outlined in Example 3 can be extended to yield non-peptide compounds that act therapeutically by inducing the dimerization of two EPO-R molecules. In two separate and parallel experiments, the mass-coded library is solubilized in an appropriate binding buffer and incubated with either EPO-R alone or EPO-R plus EPO. Compounds that bind to the protein(s) are separated from the unbound compounds by rapid size exclusion chromatography. The bound compounds are loaded with the protein(s) onto a reversed-phase column that is placed downstream of the size exclusion column. The bound compounds are dissociated from the protein(s) and are eluted from the reversed-phase column and analyzed by mass spectrometry. Masses that correspond to compounds that bind to the EPO/EPO-R interface are identified as those masses which are observed only when the library is screened with EPO-R alone; masses which are also observed in the screen with the EPO/EPO-R complex are ignored. The mass of each interface-specific compound identifies one combination of peripheral moieties plus scaffold. The individual compound(s) that result from the identified combination of peripheral moieties plus scaffold are synthesized and tested for their in vitro ability to bind to the target protein, EPO-R. Those compounds exhibiting the highest affinity for the target protein are compared to identify similarities among them. Ideally, it is observed that one site of derivatization on the scaffold is relatively unimportant for high affinity binding. The peripheral moiety at this site is subsequently replaced with a covalent tether that joins two molecules of the highest affinity compound to yield a non-peptide compound that dimerizes the target protein, EPO-R.

Example 6

Simultaneous Target Validation and Small-Molecule Drug Discovery

An example of a class of target proteins whose roles in a disease process can be validated by application of target-specific ligands to a bioassay are the proteins encoded by the open reading frames (ORF) of the Herpes Simplex Virus. The identification of ligands to an ORF-encoded protein and the use of the resulting ligands to determine the function of the ORF-encoded protein and its validity as a target for anti-viral drug discovery involves the following steps: the ORF-encoded protein is covalently biotinylated by incubation of the ORF-encoded protein with a chemically activated biotin precursor. The ORF-encoded protein-biotin conjugate is immobilized by binding to a streptavidin-derivatized water-insoluble column matrix. The mass-coded library is solubilized in an appropriate binding buffer and injected onto a column containing the ORF-encoded protein+streptavidin complex. Compounds that do not bind to the column are washed off with binding buffer. Compounds that bind to the column are dissociated by a change in the buffer conditions, such as a change in the pH or an increase in the percentage of organic solvent. These compounds are loaded onto a reversed-phase column placed downstream of the ORF-encoded protein+streptavidin column. The binding compounds are eluted from the reversed-phase column and analyzed by mass spectrometry. Molecular masses that correspond to ligands for the ORF-encoded protein are identified by eliminating those masses that are also observed when the library is similarly screened with a streptavidin column. The molecular mass of each ligand for the ORF-encoded protein identifies one combination of peripheral moieties plus scaffold. The individual compound(s) that result from the identified combination of peripheral moieties plus scaffold are synthesized and tested for their ability to inhibit the replication or transmission of the virus in a mammalian cell bioassay or animal model.

The observation of a virus-specific inhibitory activity implicates the ORF-encoded protein as a critical component of the viral disease process and confirms that the ORF-encoded protein is specifically amenable to small molecule anti-viral drug discovery. Observation of a direct correlation between the relative binding affinities of the ORF-encoded protein-specific ligands and the relative inhibitory concentrations of the ORF-encoded protein-specific ligands further strengthens the identification of the ORF-encoded protein as a target for small molecule anti-viral drug discovery.

Example 7

Development of Small Molecules that can be Applied to the Affinity Purification of a Target Protein A mass-coded combinatorial library can be used to identify ligands that have a high affinity for a target protein. One such target protein is human erythropoietin (EPO), which is expressed and purified industrially for use as a therapeutic drug. Ligands that exhibit a high affinity for EPO can be immobilized on a solid support to generate an EPO-specific affinity matrix.

The identification of ligands to EPO and the construction of an EPO-specific affinity matrix involves the following steps: the mass coded library is solubilized in an appropriate binding buffer and incubated with the EPO protein. Compounds that bind to the EPO protein are separated from the unbound compounds by rapid size exclusion chromatography. These compounds are loaded with the EPO protein onto a reversed-phase column that is placed downstream of the size exclusion column. The compounds are dissociated from the EPO protein and are eluted from the reversed-phase column and analyzed by mass spectrometry. The molecular mass of each EPO protein-specific ligand identifies one combination of peripheral moieties plus scaffold. The individual ligand(s) that result from the identified combination of peripheral moieties plus scaffold are synthesized and tested for their in vitro ability to bind to the EPO protein. Compounds exhibiting the highest affinity for the EPO protein are compared to identify similarities between the compounds. If it is observed that one reactive site on the scaffold is relatively unimportant for high affinity binding, the peripheral moiety at this site is subsequently replaced with a covalent tether that joins the EPO-specific ligand to a water insoluble matrix, thereby generating an EPO-specific affinity matrix.

Alternatively, the covalent tether is used to join the EPO-specific ligand to a another molecule, such as biotin, which possesses a high affinity for a commercially available affinity matrix (streptavidin-derivatized agarose). The biotin-streptavidin interaction is used as a strong, non-covalent immobilization technique.

Example 8

Development of Small Molecules that can be Applied to the Visualization of a Target Protein A mass-coded combinatorial library can be used to identify ligands that have a high affinity for a target protein. One such target protein is the human protein telomerase, the expression of which is linked to cancer progression and aging. Ligands that exhibit a high affinity for telomerase can be functionalized with a radioactive or non-radioactive tag to thereby generate a telomerase-specific affinity probe for visualization of the enzyme in vitro or in vivo. The identification of ligands to telomerase and the construction of a telomerase-specific affinity probe would involve the following steps: a mass-coded library is solubilized in an appropriate binding buffer and incubated with telomerase protein alone. Compounds that bind to the telomerase protein are separated from the unbound compounds by rapid size exclusion chromatography. The binding compounds are loaded with the telomerase protein onto a reversed-phase column that is placed downstream of the size exclusion column. The compounds are dissociated from the telomerase protein and are eluted from the reversed-phase column and analyzed by mass spectrometry mass of each telomerase protein-specific ligand identifies one combination of peripheral moieties plus scaffold. The individual ligand(s) that result from the identified combination of peripheral moieties plus scaffold are synthesized and tested for their in vitro ability to bind to the telomerase protein. Compounds exhibiting the highest affinity for the telomerase protein are compared to identify similarities between the compounds. Ideally, it is observed that one reactive site on the scaffold is relatively unimportant for high affinity binding. The peripheral moiety at this site is subsequently replaced with a covalent tether that joins the telomerase-specific ligand to a radioactive moiety or a non-radioactive moiety such as a fluorophore, thereby generating a telomerase-specific affinity probe.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

TABLE

| Field1 | 1 | 2 | 3 | 4 | 5 | 6 | 7 | 8 | 9 | 10 | 11 | 12 |
|---|---|---|---|---|---|---|---|---|---|---|---|---|
| 2.197802 | 86a | 79a | 13a | 108a | 76a | 20a | 1a | 70a | 26a | 94a | 21a | 97a |
| 2.490843 | 86a | 108a | 76a | 69a | 1a | 70a | 26a | 24a | 36a | 94a | 21a | 97a |
| 2.637363 | 86a | 13a | 108a | 76a | 69a | 1a | 70a | 26a | 24a | 36a | 94a | 97a |
| 2.783883 | 86a | 79a | 13a | 108a | 76a | 20a | 69a | 1a | 70a | 26a | 94a | 21a |
| 2.783883 | 86a | 79a | 13a | 108a | 76a | 20a | 69a | 1a | 70a | 36a | 94a | 21a |
| 2.783883 | 86a | 13a | 108a | 76a | 20a | 69a | 1a | 70a | 24a | 36a | 94a | 97a |
| 2.783883 | 86a | 79a | 13a | 108a | 76a | 70a | 26a | 24a | 36a | 94a | 21a | 97a |
| 2.930403 | 86a | 13a | 108a | 76a | 20a | 69a | 1a | 70a | 36a | 94a | 21a | 97a |
| 2.930403 | 86a | 13a | 108a | 76a | 1a | 70a | 26a | 24a | 36a | 94a | 21a | 97a |
| 2.930403 | 86a | 13a | 108a | 76a | 69a | 1a | 70a | 26a | 36a | 94a | 21a | 97a |
| 2.930403 | 86a | 79a | 13a | 108a | 76a | 20a | 69a | 1a | 70a | 26a | 94a | 104a |
| 3.003663 | 86a | 79a | 13a | 108a | 76a | 20a | 69a | 70a | 26a | 24a | 94a | 104a |
| 3.003663 | 86a | 79a | 13a | 108a | 20a | 69a | 1a | 70a | 36a | 94a | 21a | 97a |
| 3.076923 | 86a | 13a | 108a | 76a | 20a | 69a | 1a | 70a | 26a | 24a | 94a | 97a |
| 3.076923 | 86a | 13a | 108a | 76a | 69a | 1a | 70a | 26a | 24a | 36a | 94a | 104a |
| 3.076923 | 86a | 13a | 108a | 76a | 20a | 69a | 1a | 70a | 26a | 94a | 21a | 97a |
| 3.076923 | 86a | 108a | 76a | 20a | 69a | 1a | 70a | 24a | 36a | 94a | 104a | 97a |
| 3.076923 | 79a | 13a | 108a | 76a | 20a | 69a | 1a | 70a | 36a | 94a | 21a | 97a |
| 3.076923 | 86a | 79a | 13a | 108a | 76a | 20a | 69a | 70a | 26a | 94a | 104a | 21a |
| 3.076923 | 86a | 79a | 13a | 108a | 76a | 20a | 1a | 70a | 36a | 94a | 21a | 97a |
| 3.223443 | 86a | 13a | 108a | 76a | 69a | 1a | 70a | 26a | 36a | 94a | 104a | 21a |
| 3.223443 | 86a | 79a | 13a | 108a | 76a | 69a | 1a | 70a | 26a | 94a | 104a | 21a |
| 3.223443 | 86a | 79a | 13a | 108a | 20a | 69a | 1a | 70a | 24a | 36a | 94a | 97a |
| 3.369963 | 86a | 79a | 13a | 108a | 20a | 69a | 1a | 70a | 26a | 94a | 21a | 97a |
| 3.369963 | 86a | 13a | 108a | 76a | 20a | 69a | 1a | 70a | 26a | 94a | 104a | 21a |
| 3.369963 | 86a | 79a | 13a | 108a | 76a | 20a | 1a | 70a | 26a | 94a | 104a | 21a |
| 3.516484 | 86a | 13a | 108a | 76a | 20a | 69a | 1a | 70a | 26a | 24a | 36a | 97a |
| 3.516484 | 86a | 79a | 13a | 108a | 20a | 69a | 1a | 70a | 26a | 24a | 94a | 97a |
| 3.516484 | 86a | 13a | 108a | 76a | 20a | 69a | 1a | 70a | 26a | 24a | 94a | 104a |
| 3.516484 | 86a | 79a | 13a | 108a | 76a | 20a | 69a | 1a | 70a | 26a | 104a | 21a |
| 3.516484 | 86a | 13a | 108a | 76a | 20a | 69a | 1a | 70a | 26a | 36a | 21a | 97a |
| 3.663004 | 86a | 79a | 13a | 108a | 76a | 20a | 69a | 1a | 70a | 26a | 94a | 104a |
| 3.663004 | 79a | 13a | 108a | 76a | 69a | 1a | 70a | 36a | 94a | 104a | 21a | 97a |
| 3.663004 | 79a | 13a | 108a | 76a | 20a | 1a | 70a | 26a | 94a | 104a | 21a | 97a |
| 3.663004 | 86a | 79a | 108a | 76a | 69a | 70a | 26a | 24a | 36a | 94a | 21a | 97a |
| 3.663004 | 86a | 79a | 13a | 108a | 76a | 20a | 69a | 1a | 70a | 94a | 104a | 21a |
| 3.663004 | 86a | 13a | 108a | 76a | 20a | 69a | 1a | 70a | 26a | 36a | 94a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 3.809524 | 86a | 13a | 108a | 76a | 69a | 1a | 70a | 24a | 36a | 94a | 104a | 97a |
| 3.809524 | 79a | 13a | 108a | 76a | 69a | 1a | 70a | 26a | 94a | 104a | 21a | 97a |
| 3.809524 | 86a | 79a | 13a | 108a | 76a | 1a | 70a | 26a | 24a | 94a | 21a | 97a |
| 3.809524 | 79a | 13a | 108a | 76a | 20a | 69a | 1a | 26a | 94a | 104a | 21a | 97a |
| 3.809524 | 79a | 13a | 108a | 76a | 69a | 70a | 26a | 24a | 36a | 94a | 104a | 97a |
| 3.809524 | 86a | 79a | 13a | 108a | 76a | 20a | 69a | 1a | 70a | 26a | 94a | 21a | 97a |
| 3.882784 | 79a | 13a | 108a | 76a | 69a | 70a | 26a | 36a | 94a | 104a | 21a | 97a |
| 3.956044 | 86a | 79a | 108a | 76a | 20a | 69a | 70a | 26a | 24a | 94a | 104a | 97a |
| 3.956044 | 86a | 79a | 13a | 108a | 76a | 20a | 69a | 1a | 70a | 24a | 36a | 94a |
| 3.956044 | 86a | 79a | 13a | 108a | 76a | 20a | 69a | 1a | 36a | 94a | 21a | 97a |
| 3.956044 | 86a | 13a | 108a | 76a | 69a | 1a | 70a | 26a | 24a | 36a | 94a | 21a |
| 3.956044 | 86a | 79a | 13a | 108a | 76a | 69a | 1a | 70a | 26a | 94a | 21a | 97a |
| 3.956044 | 86a | 108a | 76a | 69a | 1a | 70a | 24a | 36a | 94a | 104a | 21a | 97a |
| 3.956044 | 79a | 13a | 108a | 76a | 20a | 69a | 1a | 70a | 26a | 24a | 104a | 97a |
| 3.956044 | 86a | 79a | 13a | 108a | 20a | 69a | 1a | 70a | 24a | 94a | 104a | 97a |
| 3.956044 | 86a | 79a | 108a | 76a | 20a | 69a | 1a | 70a | 26a | 94a | 104a | 21a |
| 3.956044 | 86a | 79a | 13a | 108a | 76a | 20a | 69a | 1a | 26a | 94a | 104a | 21a |
| 4.029304 | 86a | 79a | 13a | 76a | 20a | 69a | 1a | 70a | 26a | 24a | 94a | 104a |
| 4.102564 | 86a | 79a | 13a | 108a | 76a | 20a | 69a | 1a | 70a | 26a | 24a | 94a |
| 4.102564 | 86a | 13a | 108a | 76a | 69a | 1a | 70a | 24a | 36a | 94a | 21a | 97a |
| 4.102564 | 86a | 108a | 76a | 69a | 1a | 70a | 26a | 24a | 36a | 94a | 104a | 21a |
| 4.102564 | 79a | 13a | 108a | 76a | 20a | 69a | 1a | 70a | 94a | 104a | 21a | 97a |
| 4.102564 | 86a | 79a | 13a | 108a | 76a | 20a | 69a | 1a | 70a | 26a | 24a | 36a |
| 4.102564 | 86a | 13a | 108a | 76a | 20a | 69a | 1a | 26a | 24a | 36a | 94a | 97a |
| 4.175824 | 86a | 79a | 13a | 108a | 20a | 69a | 1a | 70a | 26a | 24a | 94a | 104a |
| 4.175824 | 86a | 79a | 13a | 108a | 76a | 69a | 70a | 26a | 36a | 94a | 21a | 97a |
| 4.175824 | 86a | 79a | 108a | 76a | 20a | 69a | 1a | 70a | 36a | 94a | 21a | 97a |
| 4.249084 | 86a | 79a | 13a | 108a | 76a | 1a | 70a | 26a | 36a | 94a | 21a | 97a |
| 4.249084 | 86a | 13a | 108a | 76a | 69a | 1a | 26a | 24a | 36a | 94a | 21a | 97a |
| 4.249084 | 86a | 79a | 13a | 108a | 76a | 69a | 70a | 26a | 36a | 94a | 104a | 21a |
| 4.249084 | 86a | 13a | 108a | 76a | 20a | 69a | 1a | 70a | 26a | 24a | 36a | 94a |
| 4.249084 | 86a | 79a | 13a | 108a | 76a | 69a | 1a | 70a | 26a | 36a | 94a | 21a | 97a |
| 4.249084 | 86a | 79a | 13a | 108a | 76a | 20a | 1a | 70a | 26a | 24a | 94a | 97a |
| 4.249084 | 79a | 13a | 108a | 76a | 20a | 69a | 70a | 26a | 24a | 94a | 104a | 97a |
| 4.249084 | 86a | 79a | 108a | 76a | 20a | 69a | 1a | 70a | 26a | 94a | 21a | 97a |
| 4.249084 | 86a | 79a | 13a | 108a | 76a | 20a | 69a | 1a | 70a | 24a | 36a | 97a |
| 4.322344 | 79a | 13a | 108a | 76a | 20a | 69a | 70a | 26a | 36a | 94a | 21a | 97a |
| 4.395605 | 86a | 79a | 13a | 108a | 69a | 1a | 70a | 26a | 24a | 36a | 94a | 97a |
| 4.395605 | 79a | 13a | 108a | 76a | 20a | 69a | 70a | 26a | 94a | 104a | 21a | 97a |
| 4.395605 | 86a | 79a | 13a | 108a | 76a | 20a | 69a | 1a | 70a | 36a | 94a | 97a |
| 4.395605 | 79a | 13a | 108a | 76a | 20a | 69a | 70a | 26a | 24a | 36a | 94a | 97a |
| 4.395605 | 86a | 79a | 13a | 108a | 76a | 20a | 69a | 1a | 70a | 26a | 24a | 97a |
| 4.395605 | 86a | 13a | 108a | 76a | 20a | 69a | 1a | 70a | 26a | 36a | 94a | 104a |
| 4.395605 | 79a | 13a | 108a | 76a | 20a | 69a | 1a | 70a | 26a | 104a | 21a | 97a |
| 4.395605 | 86a | 79a | 13a | 108a | 20a | 69a | 1a | 70a | 26a | 94a | 104a | 21a |
| 4.395605 | 79a | 13a | 108a | 76a | 20a | 69a | 1a | 70a | 26a | 94a | 104a | 21a |
| 4.395605 | 86a | 79a | 13a | 108a | 76a | 20a | 70a | 26a | 36a | 94a | 21a | 97a |
| 4.395605 | 86a | 79a | 13a | 108a | 76a | 20a | 70a | 26a | 24a | 94a | 104a | 97a |
| 4.395605 | 86a | 79a | 13a | 108a | 76a | 69a | 70a | 26a | 24a | 36a | 94a | 21a |
| 4.395605 | 13a | 108a | 76a | 69a | 1a | 70a | 26a | 36a | 94a | 104a | 21a | 97a |
| 4.395605 | 86a | 79a | 13a | 108a | 76a | 20a | 69a | 1a | 70a | 94a | 21a | 97a |
| 4.395605 | 86a | 108a | 76a | 20a | 69a | 1a | 70a | 26a | 24a | 36a | 94a | 97a |
| 4.395605 | 86a | 79a | 13a | 108a | 76a | 20a | 1a | 70a | 26a | 36a | 94a | 97a |
| 4.395605 | 86a | 79a | 13a | 108a | 76a | 69a | 70a | 26a | 24a | 36a | 94a | 97a |
| 4.468864 | 86a | 79a | 13a | 108a | 20a | 69a | 70a | 26a | 24a | 94a | 104a | 97a |
| 4.468864 | 86a | 79a | 13a | 108a | 76a | 20a | 1a | 70a | 26a | 24a | 36a | 97a |
| 4.468864 | 86a | 108a | 76a | 20a | 69a | 1a | 70a | 36a | 94a | 104a | 21a | 97a |
| 4.468864 | 86a | 79a | 13a | 108a | 76a | 20a | 69a | 70a | 26a | 24a | 36a | 94a |
| 4.468864 | 86a | 79a | 13a | 76a | 1a | 70a | 26a | 24a | 36a | 94a | 21a | 97a |
| 4.468864 | 86a | 79a | 13a | 108a | 76a | 20a | 70a | 26a | 24a | 36a | 94a | 97a |
| 4.542125 | 86a | 79a | 13a | 108a | 69a | 1a | 70a | 24a | 36a | 94a | 104a | 97a |
| 4.542125 | 86a | 79a | 13a | 108a | 76a | 20a | 69a | 70a | 26a | 36a | 94a | 21a |
| 4.542125 | 86a | 79a | 13a | 108a | 76a | 69a | 70a | 26a | 24a | 36a | 94a | 104a |
| 4.542125 | 86a | 79a | 13a | 108a | 76a | 20a | 69a | 1a | 26a | 94a | 21a | 97a |
| 4.542125 | 86a | 79a | 13a | 76a | 20a | 69a | 1a | 70a | 24a | 36a | 94a | 97a |
| 4.542125 | 86a | 108a | 76a | 20a | 69a | 1a | 70a | 26a | 36a | 94a | 21a | 97a |
| 4.542125 | 86a | 13a | 108a | 76a | 69a | 70a | 26a | 24a | 36a | 94a | 21a | 97a |
| 4.542125 | 86a | 79a | 13a | 108a | 76a | 1a | 70a | 24a | 36a | 94a | 21a | 97a |
| 4.542125 | 13a | 108a | 76a | 20a | 69a | 1a | 70a | 26a | 94a | 104a | 21a | 97a |
| 4.542125 | 86a | 13a | 108a | 76a | 20a | 69a | 1a | 26a | 36a | 94a | 21a | 97a |
| 4.542125 | 86a | 79a | 13a | 108a | 76a | 69a | 1a | 70a | 26a | 24a | 94a | 104a |
| 4.542125 | 86a | 79a | 13a | 108a | 76a | 20a | 69a | 70a | 26a | 36a | 94a | 97a |
| 4.542125 | 86a | 79a | 13a | 108a | 76a | 20a | 69a | 1a | 70a | 26a | 94a | 97a |
| 4.615385 | 79a | 108a | 76a | 20a | 69a | 1a | 70a | 36a | 94a | 104a | 21a | 97a |
| 4.688645 | 86a | 79a | 13a | 108a | 76a | 20a | 69a | 1a | 70a | 26a | 21a | 97a |
| 4.688645 | 86a | 79a | 13a | 108a | 20a | 69a | 1a | 24a | 36a | 94a | 104a | 97a |
| 4.688645 | 79a | 108a | 76a | 69a | 70a | 26a | 24a | 36a | 94a | 104a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 4.688645 | 86a | 108a | 76a | 69a | 1a | 70a | 26a | 24a | 36a | 94a | 104a | 97a |
| 4.688645 | 79a | 108a | 76a | 20a | 69a | 1a | 70a | 26a | 94a | 104a | 21a | 97a |
| 4.688645 | 13a | 108a | 76a | 69a | 1a | 70a | 26a | 24a | 36a | 94a | 104a | 97a |
| 4.688645 | 86a | 79a | 13a | 108a | 76a | 20a | 69a | 70a | 24a | 36a | 94a | 97a |
| 4.688645 | 86a | 79a | 13a | 76a | 20a | 69a | 1a | 70a | 26a | 94a | 104a | 21a |
| 4.688645 | 86a | 108a | 76a | 20a | 69a | 1a | 70a | 26a | 24a | 94a | 104a | 97a |
| 4.688645 | 86a | 13a | 108a | 76a | 20a | 1a | 70a | 26a | 24a | 36a | 94a | 97a |
| 4.688645 | 86a | 79a | 13a | 108a | 76a | 20a | 69a | 1a | 36a | 94a | 104a | 21a |
| 4.688645 | 86a | 79a | 13a | 108a | 76a | 69a | 1a | 70a | 36a | 94a | 104a | 21a |
| 4.761905 | 86a | 13a | 108a | 76a | 20a | 69a | 1a | 70a | 26a | 24a | 36a | 104a |
| 4.761905 | 86a | 79a | 13a | 108a | 1a | 70a | 26a | 24a | 36a | 94a | 21a | 97a |
| 4.761905 | 86a | 79a | 13a | 108a | 20a | 69a | 1a | 70a | 26a | 24a | 36a | 97a |
| 4.761905 | 86a | 79a | 13a | 76a | 20a | 69a | 1a | 70a | 36a | 94a | 21a | 97a |
| 4.835165 | 79a | 13a | 108a | 76a | 20a | 69a | 1a | 26a | 24a | 94a | 104a | 97a |
| 4.835165 | 86a | 79a | 13a | 108a | 76a | 20a | 69a | 1a | 26a | 24a | 94a | 104a |
| 4.835165 | 79a | 13a | 108a | 76a | 69a | 1a | 70a | 24a | 36a | 94a | 104a | 97a |
| 4.835165 | 86a | 13a | 108a | 76a | 20a | 1a | 70a | 26a | 36a | 94a | 21a | 97a |
| 4.835165 | 86a | 79a | 13a | 108a | 69a | 1a | 70a | 26a | 24a | 94a | 21a | 97a |
| 4.835165 | 79a | 108a | 76a | 20a | 69a | 70a | 26a | 24a | 36a | 94a | 104a | 97a |
| 4.835165 | 86a | 108a | 76a | 69a | 1a | 70a | 26a | 24a | 36a | 104a | 21a | 97a |
| 4.835165 | 86a | 13a | 108a | 76a | 20a | 69a | 1a | 70a | 24a | 36a | 94a | 104a |
| 4.835165 | 79a | 13a | 108a | 76a | 20a | 69a | 1a | 36a | 94a | 104a | 21a | 97a |
| 4.835165 | 13a | 108a | 76a | 20a | 69a | 1a | 70a | 26a | 24a | 36a | 94a | 97a |
| 4.835165 | 86a | 13a | 108a | 76a | 20a | 69a | 70a | 26a | 36a | 94a | 21a | 97a |
| 4.835165 | 13a | 108a | 76a | 20a | 69a | 1a | 70a | 26a | 36a | 94a | 21a | 97a |
| 4.835165 | 86a | 79a | 13a | 108a | 76a | 20a | 1a | 70a | 24a | 36a | 94a | 97a |
| 4.835165 | 86a | 79a | 13a | 108a | 76a | 20a | 69a | 70a | 26a | 24a | 94a | 97a |
| 4.835165 | 86a | 79a | 13a | 76a | 69a | 1a | 70a | 26a | 24a | 36a | 94a | 104a |
| 4.835165 | 79a | 13a | 108a | 76a | 20a | 1a | 70a | 26a | 36a | 94a | 21a | 97a |
| 4.835165 | 86a | 13a | 76a | 20a | 69a | 1a | 70a | 26a | 24a | 36a | 94a | 97a |
| 4.835165 | 86a | 13a | 108a | 76a | 20a | 69a | 1a | 70a | 24a | 94a | 104a | 97a |
| 4.908425 | 86a | 79a | 13a | 108a | 76a | 20a | 69a | 1a | 70a | 36a | 21a | 97a |
| 4.908425 | 86a | 79a | 13a | 108a | 76a | 1a | 70a | 26a | 24a | 36a | 21a | 97a |
| 4.981685 | 79a | 13a | 108a | 76a | 20a | 69a | 1a | 70a | 24a | 36a | 94a | 97a |
| 4.981685 | 86a | 13a | 108a | 76a | 20a | 69a | 1a | 70a | 36a | 94a | 104a | 21a |
| 4.981685 | 86a | 13a | 108a | 76a | 20a | 69a | 1a | 70a | 26a | 36a | 94a | 21a |
| 4.981685 | 79a | 13a | 108a | 20a | 69a | 1a | 70a | 26a | 24a | 94a | 104a | 97a |
| 4.981685 | 86a | 13a | 108a | 76a | 20a | 69a | 70a | 26a | 24a | 36a | 94a | 97a |
| 4.981685 | 86a | 108a | 76a | 20a | 69a | 1a | 70a | 26a | 24a | 36a | 94a | 104a |
| 4.981685 | 79a | 13a | 108a | 76a | 20a | 69a | 1a | 70a | 26a | 94a | 104a | 97a |
| 4.981685 | 86a | 79a | 76a | 69a | 1a | 70a | 24a | 36a | 94a | 104a | 21a | 97a |
| 4.981685 | 86a | 79a | 13a | 108a | 69a | 1a | 70a | 24a | 36a | 94a | 21a | 97a |
| 4.981685 | 86a | 79a | 108a | 76a | 20a | 69a | 1a | 70a | 26a | 24a | 94a | 104a |
| 4.981685 | 86a | 13a | 76a | 69a | 1a | 70a | 26a | 24a | 36a | 94a | 21a | 97a |
| 4.981685 | 86a | 79a | 13a | 108a | 76a | 20a | 69a | 70a | 26a | 94a | 21a | 97a |
| 4.981685 | 86a | 79a | 108a | 20a | 69a | 1a | 70a | 24a | 36a | 94a | 104a | 97a |
| 4.981685 | 86a | 13a | 108a | 76a | 69a | 1a | 70a | 26a | 24a | 36a | 21a | 97a |
| 4.981685 | 86a | 13a | 108a | 76a | 69a | 70a | 26a | 24a | 36a | 94a | 104a | 97a |
| 4.981685 | 86a | 79a | 13a | 108a | 76a | 20a | 1a | 70a | 26a | 36a | 21a | 97a |
| 4.981685 | 86a | 79a | 13a | 108a | 76a | 69a | 1a | 70a | 26a | 24a | 104a | 21a |
| 5.128205 | 13a | 108a | 76a | 20a | 69a | 1a | 70a | 26a | 24a | 94a | 104a | 97a |
| 5.128205 | 86a | 79a | 13a | 76a | 20a | 69a | 1a | 70a | 26a | 24a | 94a | 97a |
| 5.128205 | 86a | 108a | 76a | 20a | 69a | 1a | 70a | 26a | 36a | 94a | 104a | 21a |
| 5.128205 | 79a | 13a | 108a | 20a | 69a | 1a | 70a | 26a | 94a | 104a | 21a | 97a |
| 5.128205 | 86a | 79a | 13a | 76a | 69a | 1a | 70a | 26a | 24a | 36a | 94a | 97a |
| 5.128205 | 86a | 79a | 13a | 108a | 20a | 69a | 1a | 70a | 26a | 24a | 104a | 97a |
| 5.128205 | 79a | 13a | 76a | 20a | 69a | 1a | 70a | 26a | 24a | 94a | 104a | 97a |
| 5.128205 | 86a | 13a | 108a | 76a | 69a | 1a | 70a | 26a | 24a | 94a | 21a | 97a |
| 5.128205 | 86a | 79a | 76a | 20a | 69a | 1a | 70a | 24a | 36a | 94a | 104a | 97a |
| 5.128205 | 79a | 13a | 76a | 20a | 69a | 1a | 70a | 26a | 94a | 104a | 21a | 97a |
| 5.128205 | 86a | 13a | 76a | 20a | 69a | 1a | 70a | 26a | 36a | 94a | 21a | 97a |
| 5.128205 | 86a | 13a | 108a | 69a | 1a | 70a | 26a | 24a | 36a | 94a | 21a | 97a |
| 5.201465 | 86a | 13a | 108a | 76a | 20a | 69a | 1a | 70a | 26a | 36a | 104a | 21a |
| 5.274725 | 86a | 79a | 13a | 108a | 20a | 69a | 1a | 26a | 24a | 94a | 104a | 97a |
| 5.274725 | 79a | 13a | 108a | 76a | 20a | 69a | 70a | 24a | 36a | 94a | 104a | 97a |
| 5.274725 | 86a | 79a | 13a | 108a | 20a | 69a | 1a | 70a | 94a | 104a | 21a | 97a |
| 5.274725 | 86a | 13a | 108a | 20a | 69a | 1a | 70a | 26a | 36a | 94a | 21a | 97a |
| 5.274725 | 86a | 79a | 13a | 108a | 76a | 69a | 1a | 70a | 26a | 24a | 94a | 21a |
| 5.274725 | 86a | 79a | 13a | 108a | 76a | 20a | 69a | 1a | 70a | 24a | 94a | 104a |
| 5.274725 | 86a | 79a | 13a | 76a | 20a | 69a | 1a | 70a | 24a | 36a | 94a | 104a |
| 5.274725 | 86a | 79a | 13a | 108a | 76a | 20a | 1a | 70a | 26a | 24a | 94a | 104a |
| 5.274725 | 86a | 79a | 108a | 76a | 20a | 69a | 1a | 70a | 26a | 36a | 94a | 97a |
| 5.347985 | 86a | 79a | 108a | 76a | 20a | 69a | 1a | 70a | 36a | 94a | 104a | 21a |
| 5.347985 | 86a | 79a | 108a | 76a | 20a | 69a | 70a | 24a | 36a | 94a | 104a | 97a |
| 5.347985 | 79a | 13a | 108a | 76a | 69a | 70a | 26a | 24a | 36a | 94a | 21a | 97a |
| 5.347985 | 86a | 79a | 13a | 108a | 20a | 69a | 1a | 70a | 26a | 36a | 94a | 97a |
| 5.347985 | 79a | 13a | 108a | 76a | 20a | 69a | 70a | 26a | 36a | 94a | 104a | 21a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 5.347985 | 86a | 13a | 108a | 76a | 20a | 69a | 1a | 70a | 26a | 36a | 94a | 104a |
| 5.421246 | 86a | 79a | 13a | 76a | 20a | 69a | 1a | 70a | 26a | 94a | 21a | 97a |
| 5.421246 | 86a | 13a | 108a | 76a | 20a | 69a | 70a | 26a | 24a | 94a | 104a | 97a |
| 5.421246 | 86a | 79a | 13a | 108a | 76a | 69a | 1a | 70a | 26a | 36a | 94a | 97a |
| 5.421246 | 79a | 13a | 108a | 76a | 20a | 69a | 1a | 70a | 26a | 24a | 94a | 97a |
| 5.421246 | 79a | 13a | 108a | 76a | 20a | 69a | 1a | 70a | 24a | 36a | 104a | 97a |
| 5.421246 | 86a | 79a | 108a | 76a | 69a | 70a | 26a | 24a | 36a | 94a | 104a | 21a |
| 5.421246 | 108a | 76a | 69a | 1a | 70a | 26a | 24a | 36a | 94a | 104a | 21a | 97a |
| 5.421246 | 79a | 13a | 76a | 20a | 69a | 1a | 70a | 26a | 24a | 36a | 94a | 97a |
| 5.421246 | 86a | 79a | 108a | 76a | 20a | 69a | 70a | 26a | 36a | 94a | 21a | 97a |
| 5.421246 | 86a | 79a | 108a | 76a | 20a | 69a | 70a | 26a | 24a | 36a | 94a | 97a |
| 5.421246 | 86a | 79a | 108a | 20a | 69a | 1a | 70a | 26a | 24a | 94a | 104a | 97a |
| 5.421246 | 86a | 79a | 108a | 76a | 69a | 70a | 26a | 24a | 36a | 94a | 104a | 97a |
| 5.421246 | 79a | 13a | 108a | 76a | 20a | 69a | 70a | 36a | 94a | 104a | 21a | 97a |
| 5.421246 | 86a | 79a | 13a | 108a | 76a | 69a | 1a | 70a | 26a | 24a | 94a | 97a |
| 5.494505 | 86a | 79a | 13a | 108a | 20a | 69a | 70a | 26a | 24a | 36a | 94a | 97a |
| 5.494505 | 86a | 79a | 108a | 76a | 20a | 69a | 1a | 70a | 26a | 24a | 36a | 97a |
| 5.494505 | 86a | 79a | 108a | 76a | 20a | 69a | 70a | 26a | 36a | 94a | 104a | 21a |
| 5.494505 | 86a | 79a | 13a | 76a | 69a | 1a | 70a | 24a | 36a | 94a | 104a | 97a |
| 5.494505 | 86a | 79a | 13a | 108a | 76a | 20a | 70a | 26a | 94a | 104a | 21a | 97a |
| 5.494505 | 86a | 79a | 108a | 76a | 20a | 69a | 70a | 26a | 24a | 36a | 94a | 104a |
| 5.567766 | 79a | 13a | 108a | 76a | 20a | 1a | 70a | 36a | 94a | 104a | 21a | 97a |
| 5.567766 | 86a | 79a | 13a | 108a | 76a | 69a | 70a | 24a | 36a | 94a | 21a | 97a |
| 5.567766 | 86a | 79a | 13a | 76a | 20a | 69a | 1a | 70a | 26a | 24a | 36a | 97a |
| 5.567766 | 86a | 79a | 108a | 76a | 20a | 69a | 1a | 70a | 26a | 24a | 94a | 97a |
| 5.567766 | 86a | 79a | 108a | 76a | 69a | 1a | 70a | 26a | 24a | 94a | 21a | 97a |
| 5.567766 | 79a | 108a | 76a | 20a | 69a | 70a | 26a | 36a | 94a | 104a | 21a | 97a |
| 5.567766 | 86a | 79a | 13a | 108a | 20a | 69a | 70a | 26a | 36a | 94a | 21a | 97a |
| 5.567766 | 86a | 79a | 13a | 108a | 76a | 20a | 69a | 70a | 26a | 24a | 36a | 97a |
| 5.567766 | 86a | 79a | 13a | 108a | 76a | 20a | 69a | 1a | 24a | 36a | 94a | 97a |
| 5.567766 | 86a | 79a | 13a | 108a | 76a | 20a | 69a | 1a | 26a | 24a | 94a | 97a |
| 5.567766 | 86a | 79a | 13a | 108a | 76a | 69a | 26a | 24a | 36a | 94a | 104a | 97a |
| 5.567766 | 86a | 13a | 108a | 20a | 69a | 1a | 70a | 24a | 36a | 94a | 104a | 97a |
| 5.567766 | 79a | 108a | 76a | 69a | 1a | 70a | 24a | 36a | 94a | 104a | 21a | 97a |
| 5.567766 | 86a | 79a | 108a | 76a | 69a | 1a | 70a | 26a | 24a | 94a | 21a | 97a |
| 5.567766 | 13a | 108a | 76a | 69a | 1a | 70a | 26a | 24a | 36a | 94a | 21a | 97a |
| 5.567766 | 86a | 79a | 13a | 108a | 69a | 70a | 26a | 24a | 36a | 94a | 21a | 97a |
| 5.641026 | 86a | 79a | 13a | 108a | 76a | 20a | 69a | 70a | 26a | 36a | 21a | 97a |
| 5.641026 | 86a | 79a | 13a | 108a | 76a | 20a | 69a | 26a | 24a | 36a | 94a | 97a |
| 5.641026 | 86a | 79a | 13a | 108a | 76a | 20a | 69a | 1a | 26a | 24a | 36a | 97a |
| 5.641026 | 86a | 79a | 13a | 108a | 76a | 70a | 26a | 24a | 36a | 94a | 104a | 97a |
| 5.641026 | 86a | 13a | 108a | 76a | 20a | 69a | 1a | 70a | 94a | 104a | 21a | 97a |
| 5.641026 | 86a | 79a | 76a | 20a | 69a | 1a | 70a | 36a | 94a | 104a | 21a | 97a |
| 5.641026 | 86a | 13a | 108a | 76a | 20a | 69a | 1a | 26a | 24a | 94a | 104a | 97a |
| 5.641026 | 86a | 79a | 13a | 108a | 76a | 20a | 1a | 70a | 26a | 104a | 21a | 97a |
| 5.641026 | 79a | 13a | 108a | 76a | 20a | 69a | 1a | 70a | 26a | 36a | 94a | 97a |
| 5.641026 | 86a | 13a | 108a | 76a | 69a | 1a | 70a | 36a | 94a | 104a | 21a | 97a |
| 5.714286 | 86a | 79a | 13a | 108a | 69a | 1a | 70a | 26a | 24a | 94a | 104a | 97a |
| 5.714286 | 79a | 13a | 108a | 76a | 1a | 70a | 26a | 36a | 94a | 104a | 21a | 97a |
| 5.714286 | 86a | 79a | 13a | 108a | 69a | 70a | 26a | 24a | 36a | 94a | 104a | 97a |
| 5.714286 | 79a | 13a | 108a | 76a | 20a | 69a | 1a | 70a | 26a | 24a | 36a | 97a |
| 5.714286 | 79a | 13a | 108a | 76a | 69a | 1a | 70a | 26a | 24a | 94a | 104a | 97a |
| 5.714286 | 86a | 13a | 108a | 20a | 69a | 1a | 70a | 26a | 24a | 36a | 94a | 97a |
| 5.714286 | 79a | 13a | 108a | 76a | 69a | 1a | 70a | 26a | 24a | 104a | 21a | 97a |
| 5.714286 | 79a | 13a | 108a | 76a | 20a | 69a | 1a | 70a | 36a | 94a | 104a | 21a |
| 5.714286 | 86a | 79a | 13a | 108a | 76a | 20a | 69a | 1a | 70a | 24a | 94a | 97a |
| 5.714286 | 79a | 13a | 108a | 76a | 69a | 1a | 70a | 26a | 24a | 36a | 104a | 97a |
| 5.714286 | 79a | 13a | 108a | 76a | 20a | 69a | 70a | 26a | 24a | 36a | 94a | 104a |
| 5.714286 | 86a | 79a | 76a | 69a | 70a | 26a | 24a | 36a | 94a | 104a | 21a | 97a |
| 5.714286 | 86a | 79a | 13a | 108a | 76a | 69a | 1a | 70a | 26a | 24a | 36a | 97a |
| 5.714286 | 79a | 13a | 76a | 20a | 69a | 70a | 26a | 24a | 36a | 94a | 104a | 97a |
| 5.714286 | 86a | 79a | 13a | 108a | 76a | 69a | 1a | 70a | 26a | 24a | 36a | 94a |
| 5.714286 | 86a | 79a | 13a | 108a | 76a | 20a | 69a | 1a | 24a | 36a | 94a | 104a |
| 5.714286 | 13a | 108a | 76a | 20a | 69a | 1a | 70a | 36a | 94a | 104a | 21a | 97a |
| 5.714286 | 86a | 79a | 76a | 20a | 69a | 70a | 26a | 24a | 36a | 94a | 104a | 97a |
| 5.787546 | 86a | 79a | 13a | 108a | 76a | 1a | 70a | 26a | 24a | 36a | 94a | 97a |
| 5.787546 | 79a | 13a | 108a | 76a | 69a | 1a | 70a | 26a | 36a | 94a | 104a | 97a |
| 5.787546 | 79a | 13a | 108a | 20a | 69a | 1a | 70a | 26a | 36a | 94a | 104a | 97a |
| 5.860806 | 86a | 79a | 13a | 108a | 76a | 69a | 1a | 70a | 26a | 24a | 36a | 104a |
| 5.860806 | 86a | 79a | 13a | 108a | 76a | 20a | 69a | 1a | 26a | 36a | 94a | 97a |
| 5.860806 | 86a | 79a | 108a | 76a | 1a | 70a | 26a | 24a | 36a | 94a | 21a | 97a |
| 5.860806 | 86a | 79a | 13a | 76a | 69a | 70a | 26a | 24a | 36a | 94a | 21a | 97a |
| 5.860806 | 86a | 79a | 13a | 108a | 76a | 1a | 26a | 24a | 36a | 94a | 21a | 97a |
| 5.860806 | 86a | 108a | 76a | 69a | 70a | 26a | 24a | 36a | 94a | 104a | 21a | 97a |
| 5.860806 | 79a | 76a | 20a | 69a | 1a | 70a | 26a | 24a | 36a | 94a | 104a | 97a |
| 5.860806 | 86a | 79a | 13a | 108a | 76a | 69a | 26a | 24a | 36a | 94a | 21a | 97a |
| 5.860806 | 79a | 108a | 76a | 20a | 69a | 1a | 70a | 26a | 24a | 94a | 104a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 5.860806 | 79a | 13a | 108a | 76a | 20a | 69a | 1a | 70a | 26a | 24a | 94a | 104a |
| 5.860806 | 86a | 79a | 108a | 76a | 20a | 69a | 1a | 70a | 24a | 36a | 94a | 97a |
| 5.860806 | 86a | 79a | 108a | 76a | 20a | 69a | 1a | 70a | 26a | 24a | 104a | 97a |
| 5.860806 | 79a | 13a | 76a | 69a | 1a | 70a | 26a | 24a | 36a | 94a | 104a | 97a |
| 5.860806 | 86a | 79a | 13a | 108a | 20a | 1a | 70a | 26a | 24a | 94a | 104a | 97a |
| 5.860806 | 79a | 13a | 108a | 76a | 20a | 69a | 1a | 70a | 36a | 94a | 104a | 97a |
| 5.860806 | 86a | 79a | 13a | 108a | 76a | 69a | 1a | 70a | 24a | 36a | 94a | 104a |
| 5.860806 | 86a | 79a | 13a | 108a | 76a | 20a | 69a | 26a | 24a | 94a | 104a | 97a |
| 5.860806 | 86a | 79a | 13a | 76a | 20a | 1a | 70a | 26a | 24a | 36a | 94a | 97a |
| 5.860806 | 86a | 79a | 13a | 76a | 69a | 1a | 70a | 26a | 24a | 94a | 21a | 97a |
| 5.860806 | 86a | 79a | 13a | 76a | 69a | 1a | 70a | 24a | 36a | 94a | 21a | 97a |
| 5.860806 | 86a | 79a | 13a | 76a | 20a | 69a | 1a | 70a | 36a | 94a | 104a | 21a |
| 5.860806 | 86a | 79a | 13a | 108a | 76a | 20a | 1a | 26a | 36a | 94a | 21a | 97a |
| 5.934066 | 86a | 79a | 13a | 76a | 20a | 69a | 1a | 70a | 26a | 24a | 36a | 94a |
| 5.934066 | 86a | 79a | 108a | 20a | 69a | 1a | 70a | 26a | 24a | 36a | 94a | 97a |
| 5.934066 | 86a | 79a | 13a | 108a | 76a | 20a | 69a | 70a | 24a | 36a | 94a | 104a |
| 5.934066 | 86a | 79a | 13a | 108a | 76a | 1a | 70a | 26a | 24a | 104a | 21a | 97a |
| 5.934066 | 86a | 13a | 108a | 76a | 69a | 1a | 26a | 24a | 36a | 94a | 104a | 97a |
| 5.934066 | 86a | 13a | 108a | 76a | 69a | 70a | 26a | 36a | 94a | 104a | 21a | 97a |
| 5.934066 | 86a | 79a | 13a | 108a | 76a | 20a | 69a | 1a | 26a | 24a | 36a | 104a |
| 5.934066 | 86a | 79a | 13a | 108a | 76a | 20a | 1a | 70a | 26a | 24a | 104a | 97a |
| 5.934066 | 79a | 13a | 108a | 20a | 69a | 1a | 70a | 36a | 94a | 104a | 21a | 97a |
| 6.007326 | 86a | 13a | 108a | 76a | 69a | 1a | 70a | 24a | 36a | 94a | 104a | 21a |
| 6.007326 | 86a | 79a | 13a | 108a | 76a | 1a | 70a | 26a | 24a | 36a | 94a | 21a |
| 6.007326 | 79a | 13a | 108a | 76a | 69a | 1a | 70a | 24a | 36a | 94a | 21a | 97a |
| 6.007326 | 86a | 79a | 13a | 20a | 69a | 1a | 70a | 24a | 36a | 94a | 104a | 97a |
| 6.007326 | 108 | 76a | 20a | 69a | 1a | 70a | 26a | 36a | 94a | 104a | 21a | 97a |
| 6.007326 | 86a | 79a | 108a | 76a | 20a | 69a | 70a | 26a | 94a | 104a | 21a | 97a |
| 6.007326 | 13a | 108a | 76a | 20a | 69a | 1a | 70a | 26a | 36a | 94a | 104a | 21a |
| 6.007326 | 86a | 79a | 108a | 76a | 20a | 1a | 70a | 26a | 36a | 94a | 21a | 97a |
| 6.007326 | 86a | 13a | 108a | 76a | 20a | 69a | 1a | 24a | 36a | 94a | 104a | 97a |
| 6.007326 | 13a | 108a | 76a | 20a | 69a | 1a | 70a | 24a | 36a | 94a | 104a | 97a |
| 6.007326 | 86a | 79a | 13a | 76a | 69a | 70a | 26a | 24a | 36a | 94a | 104a | 97a |
| 6.007326 | 86a | 79a | 108a | 76a | 20a | 69a | 1a | 70a | 24a | 36a | 104a | 97a |
| 6.007326 | 86a | 13a | 108a | 76a | 1a | 70a | 26a | 24a | 36a | 94a | 104a | 21a |
| 6.007326 | 86a | 79a | 13a | 108a | 20a | 69a | 1a | 70a | 26a | 104a | 21a | 97a |
| 6.007326 | 79a | 108a | 76a | 20a | 69a | 1a | 70a | 24a | 36a | 94a | 104a | 97a |
| 6.007326 | 79a | 13a | 108a | 20a | 69a | 1a | 70a | 24a | 36a | 94a | 104a | 97a |
| 6.080586 | 79a | 13a | 108a | 76a | 20a | 69a | 1a | 70a | 36a | 104a | 21a | 97a |
| 6.080586 | 86a | 79a | 13a | 108a | 76a | 20a | 69a | 70a | 36a | 94a | 104a | 21a |
| 6.080586 | 86a | 79a | 13a | 108a | 76a | 20a | 69a | 1a | 70a | 24a | 104a | 97a |
| 6.080586 | 86a | 79a | 13a | 108a | 76a | 20a | 1a | 70a | 94a | 104a | 21a | 97a |
| 6.080586 | 79a | 13a | 76a | 20a | 69a | 70a | 26a | 36a | 94a | 104a | 21a | 97a |
| 6.080586 | 86a | 79a | 13a | 76a | 20a | 69a | 1a | 70a | 26a | 36a | 94a | 97a |
| 6.153846 | 86a | 79a | 13a | 108a | 76a | 20a | 69a | 70a | 24a | 94a | 104a | 97a |
| 6.153846 | 86a | 79a | 13a | 108a | 76a | 69a | 70a | 26a | 24a | 94a | 21a | 97a |
| 6.153846 | 86a | 79a | 13a | 108a | 76a | 69a | 70a | 26a | 24a | 94a | 104a | 21a |
| 6.153846 | 79a | 13a | 76a | 20a | 69a | 1a | 70a | 24a | 36a | 94a | 104a | 97a |
| 6.153846 | 108a | 76a | 20a | 69a | 1a | 70a | 26a | 24a | 36a | 94a | 104a | 97a |
| 6.153846 | 86a | 79a | 13a | 108a | 76a | 69a | 1a | 70a | 24a | 36a | 94a | 21a |
| 6.153846 | 86a | 79a | 13a | 76a | 69a | 70a | 26a | 36a | 94a | 104a | 21a | 97a |
| 6.153846 | 13a | 108a | 76a | 69a | 1a | 70a | 24a | 36a | 94a | 104a | 21a | 97a |
| 6.153846 | 86a | 79a | 13a | 108a | 76a | 1a | 70a | 26a | 24a | 94a | 104a | 21a |
| 6.153846 | 79a | 13a | 108a | 76a | 20a | 69a | 1a | 70a | 24a | 94a | 104a | 97a |
| 6.153846 | 86a | 79a | 13a | 76a | 20a | 1a | 70a | 26a | 36a | 94a | 21a | 97a |
| 6.153846 | 86a | 79a | 13a | 108a | 20a | 69a | 70a | 26a | 94a | 104a | 21a | 97a |
| 6.153846 | 86a | 79a | 13a | 108a | 76a | 69a | 1a | 70a | 26a | 36a | 94a | 21a |
| 6.153846 | 86a | 79a | 13a | 108a | 76a | 20a | 1a | 70a | 26a | 36a | 94a | 21a |
| 6.153846 | 86a | 108a | 76a | 20a | 69a | 70a | 26a | 24a | 36a | 94a | 104a | 97a |
| 6.153846 | 86a | 79a | 13a | 108a | 69a | 1a | 70a | 36a | 94a | 104a | 21a | 97a |
| 6.153846 | 86a | 79a | 76a | 20a | 69a | 70a | 26a | 36a | 94a | 104a | 21a | 97a |
| 6.227106 | 86a | 13a | 108a | 76a | 1a | 70a | 26a | 24a | 36a | 94a | 104a | 97a |
| 6.227106 | 86a | 79a | 108a | 76a | 20a | 69a | 1a | 70a | 36a | 94a | 104a | 97a |
| 6.227106 | 79a | 13a | 76a | 20a | 69a | 1a | 70a | 36a | 94a | 104a | 21a | 97a |
| 6.227106 | 86a | 108a | 76a | 20a | 69a | 1a | 70a | 26a | 24a | 36a | 104a | 97a |
| 6.227106 | 86a | 13a | 108a | 76a | 20a | 1a | 70a | 26a | 24a | 36a | 94a | 104a |
| 6.227106 | 86a | 108a | 76a | 20a | 69a | 1a | 70a | 26a | 94a | 104a | 21a | 97a |
| 6.227106 | 86a | 76a | 69a | 1a | 70a | 26a | 24a | 36a | 94a | 104a | 21a | 97a |
| 6.227106 | 86a | 79a | 13a | 108a | 76a | 20a | 69a | 1a | 70a | 36a | 94a | 104a |
| 6.227106 | 86a | 79a | 13a | 108a | 76a | 20a | 69a | 26a | 24a | 36a | 94a | 104a |
| 6.227106 | 86a | 13a | 108a | 76a | 20a | 1a | 70a | 26a | 24a | 94a | 104a | 97a |
| 6.227106 | 86a | 13a | 108a | 76a | 69a | 1a | 70a | 26a | 24a | 36a | 104a | 21a |
| 6.227106 | 86a | 13a | 108a | 76a | 20a | 69a | 1a | 70a | 26a | 104a | 21a | 97a |
| 6.227106 | 79a | 13a | 108a | 76a | 70a | 26a | 24a | 36a | 94a | 104a | 21a | 97a |
| 6.300366 | 79a | 13a | 108a | 76a | 20a | 1a | 70a | 26a | 24a | 94a | 104a | 97a |
| 6.300366 | 86a | 79a | 108a | 76a | 20a | 69a | 1a | 70a | 26a | 24a | 36a | 104a |
| 6.300366 | 86a | 79a | 13a | 108a | 76a | 20a | 69a | 26a | 36a | 94a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 6.300366 | 86a | 79a | 13a | 108a | 76a | 69a | 1a | 70a | 26a | 24a | 21a | 97a |
| 6.300366 | 79a | 13a | 108a | 76a | 20a | 69a | 1a | 24a | 36a | 94a | 104a | 97a |
| 6.300366 | 86a | 13a | 108a | 76a | 20a | 1a | 70a | 26a | 36a | 94a | 104a | 21a |
| 6.300366 | 86a | 79a | 13a | 108a | 20a | 69a | 1a | 26a | 24a | 36a | 94a | 97a |
| 6.300366 | 86a | 79a | 108a | 76a | 69a | 1a | 70a | 26a | 24a | 104a | 21a | 97a |
| 6.300366 | 86a | 79a | 13a | 76a | 20a | 69a | 70a | 26a | 24a | 36a | 94a | 104a |
| 6.300366 | 86a | 13a | 108a | 20a | 69a | 1a | 70a | 26a | 24a | 94a | 104a | 97a |
| 6.300366 | 86a | 79a | 13a | 108a | 20a | 1a | 70a | 26a | 36a | 94a | 21a | 97a |
| 6.300366 | 86a | 79a | 13a | 108a | 76a | 69a | 70a | 24a | 36a | 94a | 21a | 97a |
| 6.300366 | 79a | 13a | 108a | 76a | 69a | 70a | 24a | 36a | 94a | 104a | 21a | 97a |
| 6.373626 | 86a | 79a | 13a | 76a | 20a | 69a | 1a | 70a | 26a | 24a | 36a | 104a |
| 6.373626 | 86a | 79a | 13a | 108a | 76a | 20a | 69a | 1a | 26a | 36a | 94a | 104a |
| 6.373626 | 79a | 13a | 108a | 76a | 20a | 69a | 1a | 26a | 36a | 94a | 21a | 97a |
| 6.373626 | 86a | 13a | 108a | 76a | 20a | 69a | 1a | 26a | 24a | 36a | 94a | 104a |
| 6.373626 | 86a | 13a | 108a | 76a | 20a | 69a | 70a | 26a | 94a | 104a | 21a | 97a |
| 6.373626 | 86a | 79a | 108a | 69a | 1a | 70a | 26a | 24a | 36a | 94a | 21a | 97a |
| 6.373626 | 86a | 13a | 108a | 76a | 20a | 69a | 70a | 26a | 36a | 94a | 104a | 21a |
| 6.373626 | 86a | 79a | 108a | 76a | 69a | 1a | 70a | 24a | 36a | 104a | 21a | 97a |
| 6.373626 | 86a | 79a | 108a | 76a | 20a | 69a | 1a | 70a | 24a | 36a | 94a | 104a |
| 6.373626 | 79a | 108a | 76a | 20a | 69a | 1a | 70a | 26a | 24a | 36a | 94a | 97a |
| 6.373626 | 86a | 108a | 76a | 69a | 1a | 70a | 26a | 36a | 94a | 104a | 21a | 97a |
| 6.373626 | 86a | 79a | 108a | 76a | 20a | 69a | 1a | 70a | 26a | 36a | 94a | 104a |
| 6.373626 | 86a | 79a | 13a | 108a | 69a | 1a | 70a | 26a | 36a | 94a | 21a | 97a |
| 6.373626 | 86a | 79a | 13a | 108a | 69a | 1a | 26a | 24a | 36a | 94a | 104a | 97a |
| 6.446887 | 86a | 79a | 13a | 108a | 76a | 20a | 1a | 70a | 36a | 94a | 104a | 21a |
| 6.446887 | 86a | 79a | 108a | 76a | 20a | 69a | 26a | 24a | 36a | 94a | 104a | 97a |
| 6.446887 | 13a | 108a | 76a | 20a | 1a | 70a | 26a | 36a | 94a | 104a | 21a | 97a |
| 6.446887 | 86a | 79a | 13a | 108a | 76a | 69a | 70a | 26a | 24a | 94a | 104a | 97a |
| 6.446887 | 86a | 79a | 13a | 108a | 76a | 69a | 1a | 70a | 26a | 36a | 94a | 104a |
| 6.446887 | 86a | 13a | 108a | 76a | 20a | 69a | 1a | 70a | 36a | 94a | 104a | 97a |
| 6.446887 | 86a | 79a | 108a | 76a | 69a | 1a | 70a | 26a | 24a | 94a | 104a | 21a |
| 6.446887 | 86a | 13a | 108a | 76a | 20a | 1a | 70a | 26a | 24a | 36a | 94a | 104a |
| 6.446887 | 13a | 108a | 76a | 1a | 70a | 26a | 24a | 36a | 94a | 104a | 21a | 97a |
| 6.446887 | 86a | 79a | 108a | 76a | 20a | 69a | 1a | 24a | 36a | 94a | 104a | 97a |
| 6.446887 | 86a | 79a | 13a | 108a | 76a | 20a | 69a | 70a | 26a | 24a | 104a | 97a |
| 6.446887 | 86a | 79a | 13a | 76a | 20a | 69a | 70a | 26a | 36a | 94a | 21a | 97a |
| 6.446887 | 86a | 79a | 76a | 20a | 69a | 1a | 70a | 26a | 24a | 36a | 94a | 104a |
| 6.446887 | 86a | 79a | 108a | 69a | 1a | 70a | 24a | 36a | 94a | 104a | 21a | 97a |
| 6.446887 | 86a | 13a | 108a | 69a | 1a | 70a | 26a | 24a | 36a | 94a | 104a | 97a |
| 6.446887 | 86a | 79a | 13a | 108a | 76a | 69a | 1a | 26a | 24a | 36a | 94a | 104a |
| 6.446887 | 86a | 79a | 108a | 76a | 69a | 70a | 26a | 24a | 36a | 104a | 21a | 97a |
| 6.446887 | 79a | 13a | 108a | 76a | 1a | 70a | 26a | 24a | 36a | 94a | 21a | 97a |
| 6.446887 | 86a | 79a | 13a | 108a | 76a | 20a | 69a | 1a | 70a | 104a | 21a | 97a |
| 6.446887 | 86a | 13a | 108a | 76a | 20a | 69a | 1a | 70a | 24a | 36a | 104a | 97a |
| 6.446887 | 86a | 79a | 13a | 108a | 76a | 20a | 69a | 1a | 70a | 24a | 36a | 104a |
| 6.446887 | 86a | 79a | 13a | 108a | 20a | 69a | 1a | 70a | 26a | 94a | 104a | 97a |
| 6.446887 | 86a | 79a | 13a | 108a | 76a | 20a | 69a | 1a | 70a | 26a | 36a | 21a |
| 6.446887 | 86a | 79a | 13a | 108a | 20a | 1a | 70a | 26a | 24a | 36a | 94a | 97a |
| 6.520146 | 13a | 108a | 76a | 20a | 69a | 1a | 70a | 26a | 24a | 36a | 94a | 104a |
| 6.520146 | 79a | 13a | 108a | 76a | 20a | 69a | 1a | 26a | 24a | 36a | 94a | 97a |
| 6.520146 | 86a | 79a | 13a | 76a | 20a | 69a | 70a | 26a | 24a | 36a | 94a | 97a |
| 6.520146 | 86a | 79a | 13a | 108a | 76a | 20a | 1a | 70a | 26a | 94a | 104a | 97a |
| 6.520146 | 86a | 79a | 13a | 108a | 76a | 70a | 26a | 36a | 94a | 104a | 21a | 97a |
| 6.520146 | 86a | 13a | 108a | 76a | 69a | 1a | 70a | 26a | 24a | 36a | 104a | 97a |
| 6.520146 | 79a | 13a | 108a | 76a | 20a | 70a | 26a | 36a | 94a | 104a | 21a | 97a |
| 6.520146 | 86a | 13a | 108a | 76a | 20a | 69a | 1a | 70a | 26a | 24a | 104a | 97a |
| 6.520146 | 86a | 108a | 76a | 20a | 69a | 1a | 70a | 26a | 36a | 94a | 104a | 97a |
| 6.520146 | 86a | 13a | 108a | 76a | 69a | 1a | 70a | 26a | 36a | 94a | 104a | 97a |
| 6.520146 | 86a | 13a | 108a | 76a | 69a | 1a | 70a | 26a | 36a | 104a | 21a | 97a |
| 6.593407 | 86a | 79a | 108a | 76a | 20a | 1a | 70a | 36a | 94a | 104a | 21a | 97a |
| 6.593407 | 79a | 13a | 108a | 76a | 69a | 1a | 70a | 26a | 24a | 94a | 21a | 97a |
| 6.593407 | 86a | 13a | 108a | 76a | 20a | 69a | 1a | 26a | 36a | 94a | 104a | 21a |
| 6.593407 | 86a | 79a | 13a | 108a | 76a | 20a | 69a | 1a | 70a | 94a | 104a | 97a |
| 6.593407 | 86a | 79a | 13a | 76a | 1a | 70a | 24a | 36a | 94a | 104a | 21a | 97a |
| 6.593407 | 86a | 79a | 13a | 108a | 76a | 20a | 69a | 70a | 26a | 24a | 36a | 104a |
| 6.593407 | 86a | 79a | 13a | 76a | 69a | 1a | 70a | 26a | 24a | 94a | 104a | 21a |
| 6.593407 | 86a | 79a | 108a | 76a | 69a | 1a | 70a | 24a | 36a | 94a | 104a | 21a |
| 6.593407 | 79a | 13a | 76a | 20a | 1a | 70a | 26a | 36a | 94a | 104a | 21a | 97a |
| 6.593407 | 86a | 79a | 13a | 108a | 76a | 20a | 69a | 70a | 26a | 104a | 21a | 97a |
| 6.593407 | 86a | 79a | 13a | 108a | 20a | 69a | 1a | 70a | 24a | 36a | 104a | 97a |
| 6.593407 | 86a | 76a | 20a | 69a | 1a | 70a | 26a | 24a | 36a | 94a | 104a | 97a |
| 6.593407 | 86a | 79a | 13a | 76a | 69a | 1a | 70a | 26a | 36a | 94a | 104a | 21a |
| 6.593407 | 86a | 79a | 13a | 108a | 76a | 1a | 70a | 26a | 36a | 94a | 104a | 21a |
| 6.593407 | 86a | 79a | 13a | 108a | 76a | 20a | 69a | 70a | 26a | 36a | 94a | 97a |
| 6.593407 | 86a | 79a | 108a | 76a | 20a | 69a | 1a | 70a | 26a | 94a | 104a | 97a |
| 6.593407 | 79a | 13a | 108a | 76a | 69a | 1a | 70a | 24a | 94a | 104a | 21a | 97a |
| 6.593407 | 86a | 79a | 76a | 20a | 69a | 1a | 70a | 26a | 24a | 94a | 104a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 6.593407 | 86a | 79a | 13a | 20a | 69a | 1a | 70a | 36a | 94a | 104a | 21a | 97a |
| 6.593407 | 79a | 13a | 108a | 76a | 20a | 69a | 26a | 24a | 36a | 94a | 104a | 97a |
| 6.593407 | 86a | 13a | 108a | 76a | 20a | 69a | 70a | 24a | 36a | 94a | 104a | 97a |
| 6.593407 | 86a | 79a | 108a | 76a | 20a | 1a | 70a | 26a | 94a | 104a | 21a | 97a |
| 6.666667 | 86a | 108a | 76a | 20a | 69a | 1a | 70a | 26a | 36a | 104a | 21a | 97a |
| 6.666667 | 86a | 79a | 13a | 76a | 20a | 1a | 70a | 26a | 94a | 104a | 21a | 97a |
| 6.666667 | 79a | 13a | 108a | 69a | 1a | 70a | 26a | 24a | 36a | 94a | 104a | 97a |
| 6.666667 | 79a | 13a | 108a | 76a | 69a | 1a | 70a | 26a | 24a | 36a | 94a | 97a |
| 6.666667 | 86a | 79a | 13a | 76a | 20a | 69a | 70a | 26a | 36a | 94a | 104a | 21a |
| 6.666667 | 86a | 79a | 13a | 108a | 69a | 1a | 70a | 26a | 94a | 104a | 21a | 97a |
| 6.739927 | 86a | 79a | 13a | 108a | 76a | 69a | 1a | 24a | 36a | 94a | 104a | 97a |
| 6.739927 | 79a | 13a | 108a | 76a | 1a | 70a | 24a | 36a | 94a | 104a | 21a | 97a |
| 6.739927 | 86a | 79a | 13a | 108a | 76a | 69a | 1a | 70a | 24a | 36a | 21a | 97a |
| 6.739927 | 86a | 79a | 108a | 76a | 69a | 1a | 70a | 26a | 24a | 36a | 94a | 97a |
| 6.739927 | 86a | 79a | 13a | 76a | 20a | 1a | 70a | 24a | 36a | 94a | 104a | 97a |
| 6.739927 | 79a | 108a | 76a | 20a | 69a | 1a | 70a | 26a | 36a | 94a | 21a | 97a |
| 6.739927 | 86a | 79a | 13a | 108a | 69a | 1a | 70a | 24a | 94a | 104a | 21a | 97a |
| 6.739927 | 86a | 79a | 108a | 76a | 20a | 69a | 1a | 70a | 26a | 104a | 21a | 97a |
| 6.739927 | 86a | 79a | 13a | 76a | 20a | 1a | 70a | 36a | 94a | 104a | 21a | 97a |
| 6.739927 | 86a | 79a | 13a | 108a | 20a | 69a | 1a | 36a | 94a | 104a | 21a | 97a |
| 6.739927 | 86a | 79a | 13a | 76a | 69a | 1a | 70a | 24a | 36a | 94a | 104a | 21a |
| 6.739927 | 86a | 79a | 13a | 108a | 76a | 20a | 69a | 70a | 26a | 36a | 104a | 21a |
| 6.739927 | 79a | 13a | 108a | 76a | 20a | 70a | 26a | 24a | 36a | 94a | 104a | 97a |
| 6.739927 | 86a | 79a | 13a | 108a | 20a | 69a | 1a | 70a | 36a | 94a | 104a | 97a |
| 6.739927 | 86a | 79a | 108a | 76a | 20a | 1a | 70a | 24a | 36a | 94a | 104a | 97a |
| 6.739927 | 79a | 13a | 108a | 76a | 69a | 1a | 70a | 26a | 36a | 94a | 21a | 97a |
| 6.739927 | 86a | 79a | 13a | 108a | 20a | 69a | 1a | 70a | 24a | 36a | 94a | 104a |
| 6.739927 | 79a | 13a | 108a | 76a | 20a | 1a | 70a | 26a | 24a | 36a | 94a | 97a |
| 6.739927 | 86a | 79a | 13a | 108a | 20a | 1a | 70a | 26a | 94a | 104a | 21a | 97a |
| 6.739927 | 86a | 79a | 13a | 108a | 76a | 69a | 1a | 70a | 24a | 94a | 104a | 21a |
| 6.813187 | 86a | 79a | 13a | 108a | 69a | 70a | 26a | 36a | 94a | 104a | 21a | 97a |
| 6.813187 | 79a | 13a | 76a | 20a | 69a | 1a | 26a | 24a | 36a | 94a | 104a | 97a |
| 6.813187 | 86a | 79a | 13a | 108a | 76a | 20a | 69a | 1a | 70a | 26a | 36a | 97a |
| 6.813187 | 86a | 79a | 13a | 108a | 20a | 69a | 1a | 70a | 26a | 24a | 36a | 94a |
| 6.813187 | 13a | 76a | 20a | 69a | 1a | 70a | 26a | 24a | 36a | 94a | 104a | 97a |
| 6.813187 | 86a | 79a | 13a | 108a | 76a | 20a | 69a | 26a | 36a | 94a | 104a | 21a |
| 6.813187 | 86a | 13a | 76a | 69a | 1a | 70a | 26a | 24a | 36a | 94a | 104a | 97a |
| 6.813187 | 86a | 79a | 108a | 76a | 70a | 26a | 24a | 36a | 94a | 104a | 21a | 97a |
| 6.886447 | 79a | 13a | 108a | 76a | 20a | 1a | 70a | 26a | 36a | 94a | 104a | 21a |
| 6.886447 | 86a | 79a | 108a | 76a | 20a | 69a | 1a | 70a | 24a | 94a | 104a | 97a |
| 6.886447 | 86a | 79a | 108a | 76a | 20a | 1a | 70a | 26a | 24a | 94a | 104a | 97a |
| 6.886447 | 86a | 79a | 108a | 20a | 69a | 1a | 70a | 36a | 94a | 104a | 21a | 97a |
| 6.886447 | 79a | 13a | 108a | 76a | 69a | 70a | 26a | 24a | 94a | 104a | 21a | 97a |
| 6.886447 | 86a | 79a | 13a | 76a | 69a | 1a | 70a | 26a | 36a | 94a | 104a | 21a |
| 6.886447 | 79a | 13a | 108a | 76a | 20a | 69a | 1a | 70a | 26a | 36a | 94a | 21a |
| 6.886447 | 86a | 13a | 108a | 76a | 69a | 1a | 70a | 26a | 24a | 94a | 104a | 21a |
| 6.886447 | 13a | 76a | 20a | 69a | 1a | 70a | 26a | 36a | 94a | 104a | 21a | 97a |
| 6.886447 | 86a | 79a | 108a | 76a | 69a | 1a | 70a | 26a | 24a | 36a | 94a | 21a |
| 6.886447 | 86a | 13a | 108a | 76a | 20a | 69a | 70a | 26a | 24a | 36a | 94a | 104a |
| 6.886447 | 79a | 13a | 108a | 76a | 1a | 70a | 26a | 24a | 94a | 104a | 21a | 97a |
| 6.886447 | 79a | 13a | 76a | 69a | 1a | 70a | 24a | 36a | 94a | 104a | 21a | 97a |
| 6.886447 | 86a | 79a | 13a | 108a | 76a | 69a | 1a | 70a | 24a | 36a | 104a | 21a |
| 6.959707 | 86a | 13a | 76a | 69a | 1a | 70a | 26a | 36a | 94a | 104a | 21a | 97a |
| 6.959707 | 79a | 13a | 108a | 76a | 20a | 69a | 26a | 36a | 94a | 104a | 21a | 97a |
| 6.959707 | 86a | 13a | 108a | 76a | 69a | 1a | 70a | 26a | 24a | 94a | 104a | 97a |
| 6.959707 | 86a | 79a | 13a | 20a | 69a | 1a | 70a | 26a | 24a | 94a | 104a | 97a |
| 6.959707 | 86a | 13a | 108a | 76a | 20a | 69a | 1a | 70a | 26a | 94a | 104a | 97a |
| 6.959707 | 86a | 79a | 13a | 108a | 76a | 20a | 69a | 70a | 26a | 36a | 94a | 104a |
| 6.959707 | 79a | 108a | 76a | 69a | 1a | 70a | 26a | 24a | 36a | 94a | 104a | 97a |
| 6.959707 | 79a | 13a | 108a | 76a | 20a | 69a | 1a | 70a | 26a | 24a | 36a | 104a |
| 7.032967 | 86a | 79a | 108a | 76a | 20a | 70a | 26a | 24a | 36a | 94a | 104a | 97a |
| 7.032967 | 86a | 79a | 108a | 76a | 20a | 69a | 70a | 26a | 24a | 36a | 104a | 97a |
| 7.032967 | 86a | 13a | 108a | 20a | 69a | 1a | 70a | 36a | 94a | 104a | 21a | 97a |
| 7.032967 | 86a | 79a | 13a | 108a | 20a | 1a | 70a | 24a | 36a | 94a | 104a | 97a |
| 7.032967 | 79a | 13a | 108a | 76a | 20a | 69a | 1a | 70a | 24a | 36a | 94a | 104a |
| 7.032967 | 79a | 108a | 76a | 69a | 1a | 70a | 26a | 24a | 94a | 104a | 21a | 97a |
| 7.032967 | 86a | 79a | 108a | 76a | 20a | 69a | 1a | 70a | 94a | 104a | 21a | 97a |
| 7.032967 | 13a | 108a | 76a | 20a | 69a | 1a | 26a | 36a | 94a | 104a | 21a | 97a |
| 7.032967 | 86a | 13a | 108a | 76a | 20a | 69a | 1a | 70a | 36a | 104a | 21a | 97a |
| 7.032967 | 86a | 76a | 20a | 69a | 1a | 70a | 26a | 36a | 94a | 104a | 21a | 97a |
| 7.032967 | 79a | 13a | 108a | 76a | 69a | 1a | 70a | 24a | 36a | 104a | 21a | 97a |
| 7.032967 | 79a | 13a | 76a | 20a | 69a | 1a | 70a | 26a | 24a | 36a | 94a |  |
| 7.032967 | 86a | 79a | 13a | 108a | 69a | 1a | 70a | 26a | 24a | 94a | 104a | 21a |
| 7.032967 | 86a | 13a | 76a | 20a | 69a | 1a | 70a | 24a | 36a | 94a | 104a | 97a |
| 7.032967 | 79a | 13a | 76a | 69a | 1a | 70a | 26a | 24a | 94a | 104a | 21a | 97a |
| 7.106227 | 79a | 13a | 108a | 76a | 1a | 70a | 26a | 24a | 36a | 104a | 21a | 97a |
| 7.106227 | 86a | 79a | 108a | 76a | 69a | 70a | 26a | 36a | 94a | 104a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 7.106227 | 86a | 79a | 13a | 108a | 76a | 20a | 70a | 26a | 36a | 94a | 104a | 21a |
| 7.106227 | 86a | 79a | 13a | 108a | 76a | 69a | 70a | 24a | 36a | 94a | 104a | 97a |
| 7.106227 | 79a | 13a | 76a | 20a | 69a | 1a | 70a | 26a | 36a | 94a | 21a | 97a |
| 7.106227 | 86a | 79a | 13a | 76a | 20a | 1a | 70a | 26a | 24a | 94a | 104a | 97a |
| 7.106227 | 86a | 79a | 13a | 108a | 76a | 70a | 26a | 24a | 36a | 94a | 104a | 21a |
| 7.106227 | 86a | 79a | 108a | 76a | 20a | 69a | 1a | 36a | 94a | 104a | 21a | 97a |
| 7.106227 | 86a | 79a | 13a | 108a | 76a | 70a | 26a | 24a | 94a | 104a | 21a | 97a |
| 7.106227 | 86a | 13a | 76a | 20a | 69a | 1a | 70a | 26a | 24a | 36a | 94a | 104a |
| 7.106227 | 13a | 108a | 76a | 20a | 69a | 1a | 26a | 24a | 36a | 94a | 104a | 97a |
| 7.179487 | 86a | 79a | 13a | 108a | 76a | 69a | 1a | 24a | 36a | 94a | 21a | 97a |
| 7.179487 | 86a | 79a | 108a | 76a | 69a | 26a | 24a | 36a | 94a | 104a | 21a | 97a |
| 7.179487 | 79a | 108a | 76a | 20a | 69a | 1a | 70a | 26a | 24a | 36a | 104a | 97a |
| 7.179487 | 86a | 13a | 108a | 20a | 69a | 1a | 70a | 26a | 36a | 94a | 104a | 21a |
| 7.179487 | 86a | 79a | 13a | 108a | 76a | 20a | 69a | 24a | 36a | 94a | 104a | 97a |
| 7.179487 | 86a | 13a | 108a | 76a | 20a | 1a | 70a | 26a | 94a | 104a | 21a | 97a |
| 7.179487 | 86a | 79a | 13a | 108a | 76a | 1a | 70a | 26a | 94a | 104a | 21a | 97a |
| 7.179487 | 86a | 79a | 13a | 108a | 76a | 69a | 1a | 26a | 36a | 94a | 104a | 21a |
| 7.179487 | 86a | 79a | 13a | 108a | 76a | 20a | 69a | 1a | 24a | 36a | 94a | 97a |
| 7.179487 | 86a | 79a | 13a | 20a | 69a | 1a | 70a | 26a | 24a | 36a | 94a | 97a |
| 7.179487 | 86a | 79a | 13a | 108a | 20a | 69a | 70a | 24a | 36a | 94a | 104a | 97a |
| 7.179487 | 86a | 79a | 13a | 108a | 20a | 69a | 1a | 70a | 36a | 94a | 104a | 21a |
| 7.179487 | 86a | 79a | 13a | 108a | 20a | 69a | 1a | 94a | 104a | 21a | 97a | |
| 7.252747 | 79a | 13a | 76a | 20a | 1a | 70a | 26a | 24a | 36a | 94a | 104a | 97a |
| 7.252747 | 86a | 79a | 13a | 108a | 76a | 20a | 1a | 70a | 26a | 24a | 36a | 104a |
| 7.252747 | 86a | 79a | 13a | 108a | 20a | 69a | 1a | 70a | 26a | 36a | 21a | 97a |
| 7.252747 | 86a | 79a | 108a | 76a | 20a | 69a | 1a | 70a | 36a | 104a | 21a | 97a |
| 7.252747 | 86a | 79a | 13a | 108a | 76a | 20a | 70a | 26a | 24a | 36a | 94a | 104a |
| 7.252747 | 86a | 79a | 13a | 108a | 76a | 69a | 1a | 36a | 94a | 104a | 21a | 97a |
| 7.252747 | 86a | 79a | 13a | 108a | 76a | 69a | 1a | 70a | 36a | 94a | 104a | 97a |
| 7.252747 | 86a | 79a | 13a | 76a | 20a | 69a | 1a | 70a | 26a | 36a | 94a | 104a |
| 7.252747 | 79a | 13a | 108a | 76a | 69a | 1a | 26a | 24a | 36a | 94a | 104a | 97a |
| 7.252747 | 86a | 108a | 76a | 20a | 69a | 1a | 26a | 24a | 36a | 94a | 104a | 97a |
| 7.252747 | 86a | 79a | 108a | 76a | 69a | 70a | 24a | 36a | 94a | 104a | 21a | 97a |
| 7.252747 | 86a | 79a | 13a | 108a | 76a | 69a | 70a | 26a | 24a | 36a | 21a | 97a |
| 7.326007 | 86a | 79a | 108a | 76a | 20a | 69a | 70a | 36a | 94a | 104a | 21a | 97a |
| 7.326007 | 86a | 79a | 13a | 108a | 76a | 1a | 70a | 36a | 94a | 104a | 21a | 97a |
| 7.326007 | 86a | 79a | 76a | 20a | 69a | 1a | 70a | 26a | 94a | 104a | 21a | 97a |
| 7.326007 | 79a | 13a | 108a | 69a | 1a | 70a | 24a | 36a | 94a | 104a | 21a | 97a |
| 7.326007 | 86a | 79a | 13a | 108a | 69a | 1a | 70a | 26a | 24a | 36a | 94a | 104a |
| 7.326007 | 86a | 79a | 13a | 76a | 20a | 69a | 1a | 24a | 36a | 94a | 104a | 97a |
| 7.326007 | 86a | 79a | 13a | 108a | 76a | 20a | 69a | 1a | 36a | 94a | 104a | 97a |
| 7.326007 | 86a | 79a | 13a | 108a | 76a | 20a | 1a | 26a | 94a | 104a | 21a | 97a |
| 7.326007 | 86a | 79a | 13a | 108a | 76a | 69a | 1a | 26a | 24a | 36a | 94a | 97a |
| 7.326007 | 86a | 79a | 13a | 108a | 76a | 69a | 1a | 26a | 36a | 94a | 21a | 97a |
| 7.326007 | 86a | 79a | 13a | 108a | 76a | 20a | 69a | 1a | 70a | 36a | 104a | 21a |
| 7.326007 | 86a | 79a | 108a | 76a | 20a | 69a | 1a | 70a | 26a | 24a | 36a | 94a |
| 7.399267 | 86a | 79a | 76a | 20a | 69a | 1a | 70a | 26a | 24a | 36a | 104a | 97a |
| 7.399267 | 86a | 79a | 108a | 76a | 20a | 69a | 70a | 26a | 36a | 94a | 104a | 97a |
| 7.399267 | 79a | 108a | 76a | 20a | 69a | 1a | 70a | 26a | 36a | 94a | 104a | 97a |
| 7.399267 | 86a | 79a | 13a | 108a | 76a | 1a | 70a | 26a | 24a | 36a | 104a | 21a |
| 7.399267 | 86a | 79a | 13a | 76a | 20a | 69a | 1a | 70a | 24a | 94a | 104a | 97a |
| 7.399267 | 13a | 108a | 76a | 20a | 1a | 70a | 26a | 24a | 94a | 104a | 21a | 97a |
| 7.399267 | 86a | 79a | 76a | 69a | 1a | 70a | 26a | 24a | 36a | 94a | 21a | 97a |
| 7.399267 | 86a | 79a | 13a | 108a | 76a | 20a | 1a | 36a | 94a | 104a | 21a | 97a |
| 7.399267 | 86a | 79a | 13a | 108a | 76a | 20a | 69a | 1a | 26a | 24a | 104a | 97a |
| 7.399267 | 86a | 108a | 76a | 20a | 69a | 70a | 26a | 36a | 94a | 104a | 21a | 97a |
| 7.399267 | 86a | 79a | 13a | 76a | 70a | 26a | 24a | 36a | 94a | 104a | 21a | 97a |
| 7.399267 | 86a | 79a | 13a | 108a | 76a | 20a | 1a | 26a | 24a | 36a | 94a | 97a |
| 7.399267 | 79a | 13a | 76a | 20a | 69a | 1a | 70a | 26a | 24a | 36a | 104a | 97a |
| 7.399267 | 86a | 108a | 76a | 69a | 1a | 26a | 24a | 36a | 94a | 104a | 21a | 97a |
| 7.399267 | 86a | 79a | 13a | 76a | 20a | 69a | 70a | 26a | 24a | 94a | 104a | 97a |
| 7.399267 | 86a | 79a | 76a | 20a | 69a | 1a | 70a | 26a | 24a | 36a | 94a | 97a |
| 7.399267 | 86a | 13a | 108a | 20a | 69a | 1a | 70a | 26a | 94a | 104a | 21a | 97a |
| 7.399267 | 86a | 13a | 108a | 69a | 1a | 70a | 26a | 36a | 94a | 104a | 21a | 97a |
| 7.472528 | 86a | 79a | 108a | 76a | 69a | 1a | 70a | 24a | 36a | 94a | 104a | 97a |
| 7.472528 | 86a | 79a | 13a | 108a | 20a | 69a | 1a | 70a | 36a | 104a | 21a | 97a |
| 7.472528 | 86a | 13a | 76a | 20a | 69a | 1a | 70a | 26a | 36a | 94a | 104a | 21a |
| 7.472528 | 86a | 79a | 13a | 76a | 69a | 1a | 70a | 26a | 24a | 36a | 94a | 21a |
| 7.472528 | 79a | 13a | 108a | 76a | 20a | 1a | 70a | 24a | 36a | 94a | 104a | 97a |
| 7.472528 | 79a | 13a | 108a | 76a | 20a | 69a | 70a | 26a | 24a | 36a | 104a | 97a |
| 7.472528 | 86a | 13a | 76a | 20a | 69a | 1a | 70a | 36a | 94a | 104a | 21a | 97a |
| 7.472528 | 86a | 79a | 13a | 76a | 20a | 69a | 1a | 70a | 94a | 104a | 21a | 97a |
| 7.472528 | 86a | 79a | 13a | 108a | 76a | 20a | 1a | 24a | 36a | 94a | 104a | 97a |
| 7.472528 | 86a | 79a | 108a | 76a | 69a | 70a | 26a | 24a | 94a | 104a | 21a | 97a |
| 7.472528 | 86a | 13a | 108a | 76a | 20a | 69a | 1a | 26a | 94a | 104a | 21a | 97a |
| 7.472528 | 86a | 79a | 108a | 76a | 69a | 1a | 70a | 26a | 36a | 94a | 21a | 97a |
| 7.472528 | 86a | 79a | 13a | 108a | 76a | 20a | 1a | 70a | 24a | 94a | 104a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 7.472528 | 86a | 13a | 108a | 76a | 1a | 70a | 26a | 36a | 94a | 104a | 21a | 97a |
| 7.472528 | 86a | 79a | 13a | 108a | 76a | 69a | 1a | 70a | 24a | 94a | 21a | 97a |
| 7.472528 | 86a | 79a | 13a | 108a | 76a | 69a | 1a | 26a | 24a | 94a | 21a | 97a |
| 7.545787 | 86a | 13a | 76a | 20a | 69a | 1a | 70a | 26a | 24a | 94a | 104a | 97a |
| 7.545787 | 86a | 13a | 108a | 76a | 20a | 1a | 70a | 36a | 94a | 104a | 21a | 97a |
| 7.545787 | 86a | 108a | 76a | 1a | 70a | 26a | 24a | 36a | 94a | 104a | 21a | 97a |
| 7.545787 | 86a | 79a | 13a | 76a | 20a | 70a | 26a | 36a | 94a | 104a | 21a | 97a |
| 7.545787 | 86a | 79a | 13a | 108a | 76a | 20a | 1a | 26a | 24a | 94a | 104a | 97a |
| 7.545787 | 86a | 79a | 13a | 108a | 76a | 69a | 26a | 36a | 94a | 104a | 21a | 97a |
| 7.545787 | 86a | 79a | 13a | 108a | 76a | 69a | 70a | 26a | 94a | 104a | 21a | 97a |
| 7.545787 | 86a | 79a | 13a | 108a | 76a | 69a | 1a | 70a | 94a | 104a | 21a | 97a |
| 7.545787 | 86a | 79a | 13a | 76a | 69a | 1a | 70a | 26a | 36a | 94a | 21a | 97a |
| 7.545787 | 79a | 13a | 76a | 69a | 1a | 70a | 26a | 36a | 94a | 104a | 21a | 97a |
| 7.619048 | 86a | 13a | 108a | 76a | 69a | 1a | 70a | 24a | 94a | 104a | 21a | 97a |
| 7.619048 | 86a | 79a | 13a | 108a | 76a | 69a | 1a | 70a | 26a | 24a | 104a | 97a |
| 7.619048 | 86a | 13a | 108a | 76a | 69a | 1a | 26a | 36a | 94a | 104a | 21a | 97a |
| 7.619048 | 86a | 79a | 13a | 108a | 76a | 20a | 1a | 26a | 36a | 94a | 104a | 21a |
| 7.619048 | 79a | 108a | 76a | 20a | 1a | 70a | 26a | 36a | 94a | 104a | 21a | 97a |
| 7.619048 | 79a | 13a | 108a | 20a | 69a | 1a | 70a | 26a | 36a | 94a | 21a | 97a |
| 7.619048 | 86a | 79a | 13a | 76a | 20a | 69a | 1a | 26a | 24a | 36a | 94a | 97a |
| 7.619048 | 86a | 79a | 108a | 76a | 20a | 69a | 1a | 70a | 26a | 36a | 94a | 21a |
| 7.619048 | 86a | 79a | 13a | 69a | 1a | 70a | 24a | 36a | 94a | 104a | 21a | 97a |
| 7.619048 | 86a | 13a | 108a | 76a | 20a | 69a | 1a | 36a | 94a | 104a | 21a | 97a |
| 7.619048 | 86a | 79a | 13a | 108a | 76a | 20a | 69a | 70a | 26a | 94a | 104a | 97a |
| 7.619048 | 79a | 108a | 76a | 69a | 1a | 70a | 26a | 24a | 36a | 104a | 21a | 97a |
| 7.619048 | 86a | 79a | 13a | 20a | 69a | 70a | 26a | 24a | 36a | 94a | 104a | 97a |
| 7.619048 | 79a | 13a | 108a | 76a | 20a | 1a | 26a | 36a | 94a | 104a | 21a | 97a |
| 7.619048 | 86a | 79a | 13a | 108a | 69a | 1a | 70a | 26a | 24a | 104a | 21a | 97a |
| 7.619048 | 86a | 79a | 108a | 76a | 20a | 1a | 70a | 26a | 24a | 36a | 94a | 97a |
| 7.619048 | 86a | 79a | 13a | 20a | 69a | 1a | 70a | 26a | 94a | 104a | 21a | 97a |
| 7.692307 | 86a | 79a | 13a | 108a | 76a | 20a | 70a | 24a | 36a | 94a | 104a | 97a |
| 7.692307 | 86a | 79a | 108a | 20a | 69a | 1a | 70a | 26a | 94a | 104a | 21a | 97a |
| 7.692307 | 86a | 79a | 13a | 108a | 76a | 20a | 69a | 26a | 94a | 104a | 21a | 97a |
| 7.692307 | 79a | 108a | 20a | 69a | 1a | 70a | 26a | 24a | 36a | 94a | 104a | 97a |
| 7.692307 | 86a | 79a | 13a | 76a | 69a | 70a | 26a | 24a | 94a | 104a | 21a | |
| 7.692307 | 79a | 13a | 108a | 76a | 69a | 1a | 26a | 36a | 94a | 104a | 21a | 97a |
| 7.692307 | 86a | 79a | 13a | 108a | 76a | 20a | 69a | 1a | 94a | 104a | 21a | 97a |
| 7.692307 | 86a | 13a | 108a | 76a | 69a | 70a | 26a | 24a | 36a | 94a | 104a | 21a |
| 7.692307 | 86a | 79a | 76a | 69a | 1a | 70a | 26a | 24a | 36a | 94a | 104a | 97a |
| 7.692307 | 86a | 13a | 76a | 20a | 69a | 1a | 70a | 26a | 94a | 104a | 21a | 97a |
| 7.692307 | 86a | 13a | 108a | 76a | 69a | 1a | 70a | 26a | 94a | 104a | 21a | 97a |
| 7.692307 | 86a | 79a | 13a | 108a | 76a | 20a | 69a | 1a | 26a | 94a | 104a | 97a |
| 7.692307 | 86a | 79a | 13a | 108a | 76a | 20a | 69a | 1a | 26a | 36a | 104a | 97a |
| 7.692307 | 86a | 13a | 108a | 76a | 1a | 70a | 24a | 36a | 94a | 104a | 21a | 97a |
| 7.692307 | 86a | 79a | 13a | 108a | 76a | 70a | 26a | 24a | 36a | 104a | 21a | 97a |
| 7.692307 | 86a | 79a | 13a | 108a | 76a | 1a | 70a | 24a | 36a | 94a | 104a | 97a |
| 7.692307 | 86a | 79a | 13a | 108a | 76a | 69a | 1a | 70a | 24a | 94a | 104a | 97a |
| 7.692307 | 86a | 108a | 76a | 20a | 1a | 70a | 26a | 24a | 36a | 94a | 104a | 97a |
| 7.765568 | 86a | 79a | 13a | 108a | 76a | 69a | 1a | 70a | 26a | 24a | 36a | 21a |
| 7.765568 | 79a | 13a | 108a | 76a | 69a | 1a | 70a | 26a | 24a | 36a | 94a | 104a |
| 7.765568 | 86a | 13a | 108a | 76a | 1a | 70a | 26a | 24a | 36a | 104a | 21a | 97a |
| 7.765568 | 86a | 79a | 13a | 108a | 69a | 1a | 26a | 24a | 36a | 94a | 104a | 97a |
| 7.765568 | 86a | 79a | 13a | 76a | 1a | 70a | 26a | 24a | 36a | 94a | 104a | 21a |
| 7.765568 | 86a | 79a | 13a | 108a | 1a | 70a | 24a | 36a | 94a | 104a | 21a | 97a |
| 7.765568 | 86a | 79a | 13a | 76a | 1a | 70a | 26a | 24a | 94a | 104a | 21a | 97a |
| 7.765568 | 86a | 79a | 108a | 76a | 20a | 69a | 1a | 26a | 24a | 36a | 94a | 104a |
| 7.765568 | 86a | 79a | 108a | 76a | 20a | 69a | 70a | 26a | 36a | 104a | 21a | 97a |
| 7.765568 | 86a | 79a | 13a | 108a | 76a | 69a | 1a | 24a | 36a | 94a | 104a | 21a |
| 7.765568 | 79a | 108a | 76a | 69a | 1a | 70a | 26a | 36a | 94a | 104a | 21a | 97a |
| 7.765568 | 86a | 79a | 108a | 76a | 20a | 69a | 1a | 26a | 24a | 94a | 21a | 97a |
| 7.765568 | 79a | 76a | 20a | 69a | 1a | 70a | 26a | 36a | 94a | 104a | 21a | 97a |
| 7.838828 | 86a | 79a | 13a | 108a | 76a | 20a | 69a | 70a | 94a | 104a | 21a | 97a |
| 7.838828 | 86a | 79a | 13a | 76a | 20a | 69a | 1a | 70a | 24a | 36a | 104a | 97a |
| 7.838828 | 86a | 79a | 13a | 108a | 76a | 69a | 1a | 70a | 26a | 104a | 21a | 97a |
| 7.838828 | 79a | 13a | 76a | 20a | 69a | 1a | 70a | 26a | 24a | 36a | 94a | 104a |
| 7.838828 | 86a | 79a | 13a | 108a | 76a | 20a | 1a | 70a | 24a | 36a | 104a | 97a |
| 7.838828 | 13a | 108a | 76a | 69a | 1a | 70a | 26a | 24a | 36a | 104a | 21a | 97a |
| 7.838828 | 86a | 79a | 13a | 108a | 76a | 20a | 1a | 70a | 26a | 36a | 104a | 21a |
| 7.838828 | 79a | 108a | 76a | 69a | 1a | 70a | 26a | 24a | 36a | 94a | 21a | 97a |
| 7.838828 | 86a | 79a | 13a | 108a | 76a | 20a | 1a | 70a | 26a | 36a | 94a | 104a |
| 7.838828 | 86a | 13a | 108a | 20a | 69a | 1a | 70a | 26a | 24a | 36a | 94a | 104a |
| 7.838828 | 86a | 13a | 108a | 76a | 20a | 69a | 70a | 36a | 94a | 104a | 21a | 97a |
| 7.838828 | 86a | 79a | 13a | 108a | 76a | 1a | 70a | 26a | 94a | 104a | 21a | 97a |
| 7.838828 | 86a | 79a | 13a | 108a | 76a | 20a | 69a | 1a | 70a | 26a | 104a | 97a |
| 7.838828 | 86a | 79a | 13a | 108a | 76a | 20a | 69a | 1a | 70a | 26a | 36a | 104a |
| 7.838828 | 86a | 79a | 13a | 76a | 20a | 70a | 26a | 24a | 36a | 94a | 104a | 97a |
| 7.838828 | 86a | 79a | 13a | 108a | 76a | 20a | 1a | 70a | 26a | 24a | 36a | 94a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 7.838828 | 86a | 79a | 13a | 69a | 1a | 70a | 26a | 24a | 36a | 94a | 104a | 97a |
| 7.838828 | 86a | 79a | 108a | 76a | 69a | 1a | 70a | 26a | 24a | 36a | 21a | 97a |
| 7.838828 | 86a | 79a | 13a | 108a | 76a | 20a | 69a | 1a | 26a | 24a | 36a | 94a |
| 7.838828 | 86a | 79a | 13a | 108a | 20a | 69a | 1a | 26a | 36a | 94a | 21a | 97a |
| 7.838828 | 86a | 79a | 13a | 108a | 76a | 20a | 1a | 70a | 36a | 94a | 104a | 97a |
| 7.912088 | 86a | 79a | 108a | 76a | 1a | 70a | 24a | 36a | 94a | 104a | 21a | 97a |
| 7.912088 | 86a | 79a | 13a | 108a | 69a | 1a | 24a | 36a | 94a | 104a | 21a | 97a |
| 7.912088 | 86a | 79a | 108a | 76a | 69a | 1a | 70a | 26a | 24a | 94a | 104a | 97a |
| 7.912088 | 86a | 79a | 13a | 76a | 69a | 1a | 70a | 24a | 94a | 104a | 21a | 97a |
| 7.912088 | 86a | 13a | 108a | 76a | 69a | 1a | 26a | 24a | 36a | 94a | 104a | 21a |
| 7.912088 | 86a | 108a | 76a | 69a | 1a | 70a | 26a | 24a | 94a | 104a | 21a | 97a |
| 7.912088 | 86a | 79a | 13a | 76a | 20a | 69a | 1a | 70a | 26a | 36a | 94a | 21a |
| 7.912088 | 86a | 79a | 13a | 76a | 69a | 1a | 70a | 26a | 24a | 94a | 104a | 97a |
| 7.912088 | 86a | 79a | 13a | 108a | 76a | 20a | 69a | 1a | 24a | 94a | 104a | 97a |
| 7.912088 | 86a | 79a | 76a | 69a | 1a | 70a | 26a | 24a | 36a | 94a | 104a | 21a |
| 7.912088 | 79a | 13a | 108a | 76a | 20a | 69a | 1a | 70a | 26a | 36a | 21a | 97a |
| 7.912088 | 86a | 79a | 13a | 108a | 20a | 1a | 70a | 36a | 94a | 104a | 21a | 97a |
| 7.912088 | 86a | 79a | 13a | 76a | 20a | 69a | 70a | 26a | 94a | 104a | 21a | 97a |
| 7.912088 | 86a | 79a | 76a | 20a | 1a | 70a | 26a | 24a | 36a | 94a | 104a | 97a |
| 7.912088 | 79a | 13a | 108a | 69a | 1a | 70a | 26a | 24a | 94a | 104a | 21a | 97a |
| 7.912088 | 86a | 79a | 13a | 76a | 20a | 1a | 70a | 26a | 36a | 94a | 104a | 21a |
| 7.912088 | 86a | 79a | 13a | 108a | 76a | 20a | 69a | 1a | 26a | 36a | 94a | 21a |
| 7.985348 | 86a | 79a | 13a | 108a | 76a | 69a | 1a | 70a | 26a | 94a | 104a | 97a |
| 7.985348 | 86a | 79a | 13a | 108a | 1a | 70a | 26a | 24a | 94a | 104a | 21a | 97a |
| 7.985348 | 86a | 79a | 76a | 69a | 1a | 70a | 26a | 24a | 94a | 104a | 21a | 97a |
| 7.985348 | 79a | 13a | 108a | 76a | 20a | 69a | 70a | 26a | 36a | 104a | 21a | 97a |
| 7.985348 | 86a | 79a | 13a | 108a | 76a | 20a | 69a | 1a | 26a | 104a | 21a | 97a |
| 7.985348 | 86a | 79a | 13a | 108a | 76a | 69a | 70a | 26a | 36a | 94a | 104a | 97a |
| 7.985348 | 86a | 79a | 13a | 76a | 1a | 70a | 26a | 36a | 94a | 104a | 21a | 97a |
| 7.985348 | 86a | 79a | 13a | 108a | 76a | 69a | 26a | 24a | 36a | 94a | 104a | 21a |
| 7.985348 | 86a | 79a | 76a | 20a | 69a | 1a | 70a | 26a | 36a | 94a | 104a | 97a |
| 7.985348 | 79a | 13a | 108a | 76a | 69a | 70a | 26a | 24a | 36a | 104a | 21a | 97a |
| 7.985348 | 79a | 13a | 108a | 76a | 20a | 69a | 1a | 70a | 26a | 36a | 94a | 104a |
| 7.985348 | 79a | 13a | 108a | 76a | 20a | 69a | 1a | 26a | 24a | 36a | 104a | 97a |
| 8.058608 | 86a | 79a | 13a | 76a | 1a | 70a | 26a | 24a | 36a | 94a | 104a | 97a |
| 8.058608 | 86a | 79a | 13a | 108a | 76a | 69a | 1a | 26a | 24a | 94a | 104a | 21a |
| 8.058608 | 86a | 79a | 13a | 108a | 76a | 1a | 70a | 24a | 36a | 94a | 104a | 21a |
| 8.058608 | 79a | 108a | 76a | 20a | 69a | 1a | 70a | 26a | 24a | 36a | 94a | 104a |
| 8.058608 | 86a | 79a | 108a | 76a | 69a | 1a | 70a | 26a | 24a | 36a | 94a | 104a |
| 8.058608 | 86a | 79a | 13a | 76a | 20a | 1a | 70a | 26a | 24a | 36a | 94a | 104a |
| 8.058608 | 86a | 79a | 13a | 108a | 76a | 20a | 1a | 70a | 24a | 36a | 94a | 104a |
| 8.058608 | 79a | 13a | 108a | 76a | 69a | 1a | 70a | 26a | 36a | 94a | 104a | 21a |
| 8.058608 | 86a | 79a | 108a | 20a | 69a | 70a | 26a | 24a | 36a | 94a | 104a | 97a |
| 8.058608 | 86a | 79a | 13a | 76a | 20a | 69a | 1a | 70a | 26a | 24a | 104a | 97a |
| 8.058608 | 86a | 79a | 13a | 108a | 20a | 69a | 1a | 70a | 26a | 36a | 94a | 21a |
| 8.058608 | 79a | 13a | 108a | 76a | 69a | 1a | 24a | 36a | 94a | 104a | 21a | 97a |
| 8.131868 | 79a | 13a | 76a | 20a | 69a | 1a | 70a | 26a | 36a | 94a | 104a | 97a |
| 8.131868 | 86a | 13a | 108a | 76a | 20a | 69a | 70a | 26a | 36a | 104a | 21a | 97a |
| 8.131868 | 86a | 79a | 76a | 1a | 70a | 26a | 24a | 36a | 94a | 104a | 21a | 97a |
| 8.131868 | 79a | 13a | 108a | 76a | 69a | 1a | 70a | 26a | 36a | 104a | 21a | 97a |
| 8.131868 | 13a | 108a | 76a | 20a | 69a | 1a | 70a | 26a | 24a | 36a | 104a | 97a |
| 8.131868 | 86a | 79a | 108a | 69a | 70a | 26a | 24a | 36a | 94a | 104a | 21a | 97a |
| 8.131868 | 86a | 79a | 108a | 69a | 1a | 70a | 26a | 24a | 36a | 94a | 104a | 97a |
| 8.131868 | 13a | 108a | 76a | 20a | 69a | 70a | 26a | 36a | 94a | 104a | 21a | 97a |
| 8.131868 | 86a | 79a | 13a | 76a | 20a | 69a | 1a | 26a | 24a | 94a | 104a | 97a |
| 8.131868 | 86a | 13a | 108a | 76a | 69a | 1a | 70a | 24a | 36a | 94a | 104a | 97a |
| 8.131868 | 13a | 108a | 76a | 20a | 69a | 1a | 70a | 26a | 36a | 104a | 21a | 97a |
| 8.131868 | 86a | 79a | 108a | 76a | 1a | 70a | 26a | 24a | 36a | 104a | 21a | 97a |
| 8.131868 | 86a | 79a | 108a | 76a | 69a | 1a | 70a | 26a | 24a | 36a | 104a | 21a |
| 8.131868 | 86a | 13a | 76a | 69a | 1a | 70a | 24a | 36a | 94a | 104a | 21a | 97a |
| 8.131868 | 86a | 79a | 108a | 76a | 69a | 1a | 70a | 26a | 36a | 94a | 104a | 21a |
| 8.131868 | 86a | 79a | 13a | 108a | 76a | 1a | 70a | 26a | 24a | 94a | 104a | 97a |
| 8.131868 | 86a | 79a | 13a | 76a | 69a | 1a | 70a | 26a | 94a | 104a | 21a | 97a |
| 8.131868 | 86a | 79a | 108a | 76a | 69a | 1a | 70a | 26a | 94a | 104a | 21a | 97a |
| 8.205129 | 86a | 79a | 13a | 108a | 76a | 1a | 70a | 24a | 36a | 104a | 21a | 97a |
| 8.205129 | 86a | 79a | 13a | 76a | 20a | 69a | 70a | 26a | 24a | 36a | 104a | 97a |
| 8.205129 | 86a | 79a | 13a | 76a | 20a | 69a | 1a | 36a | 94a | 104a | 21a | 97a |
| 8.205129 | 86a | 79a | 13a | 108a | 76a | 26a | 24a | 36a | 94a | 104a | 21a | 97a |
| 8.205129 | 86a | 79a | 13a | 108a | 76a | 20a | 26a | 24a | 36a | 94a | 104a | 97a |
| 8.205129 | 13a | 108a | 76a | 69a | 1a | 70a | 26a | 24a | 94a | 104a | 21a | 97a |
| 8.205129 | 86a | 79a | 13a | 76a | 20a | 69a | 70a | 24a | 36a | 94a | 104a | 97a |
| 8.205129 | 86a | 79a | 108a | 76a | 69a | 1a | 70a | 36a | 94a | 104a | 21a | 97a |
| 8.205129 | 86a | 79a | 13a | 108a | 76a | 69a | 1a | 70a | 104a | 21a | | |
| 8.205129 | 86a | 79a | 108a | 76a | 69a | 1a | 24a | 36a | 94a | 104a | 21a | 97a |
| 8.205129 | 86a | 13a | 108a | 69a | 1a | 70a | 24a | 36a | 94a | 104a | 21a | 97a |
| 8.205129 | 86a | 13a | 76a | 69a | 1a | 70a | 26a | 24a | 36a | 94a | 104a | 21a |
| 8.205129 | 86a | 79a | 13a | 108a | 76a | 69a | 70a | 26a | 36a | 104a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 8.278388 | 79a | 108a | 76a | 20a | 69a | 1a | 26a | 24a | 36a | 94a | 104a | 97a |
| 8.278388 | 86a | 79a | 108a | 20a | 69a | 1a | 70a | 26a | 36a | 94a | 21a | 97a |
| 8.278388 | 86a | 79a | 108a | 76a | 20a | 69a | 1a | 70a | 26a | 36a | 21a | 97a |
| 8.351648 | 86a | 79a | 108a | 76a | 20a | 70a | 26a | 36a | 94a | 104a | 21a | 97a |
| 8.351648 | 86a | 79a | 13a | 108a | 76a | 20a | 69a | 1a | 36a | 104a | 21a | 97a |
| 8.351648 | 86a | 79a | 108a | 76a | 69a | 1a | 70a | 24a | 94a | 104a | 21a | 97a |
| 8.351648 | 86a | 79a | 13a | 108a | 76a | 69a | 70a | 24a | 36a | 94a | 104a | 21a |
| 8.351648 | 86a | 79a | 13a | 108a | 76a | 69a | 70a | 26a | 24a | 36a | 104a | 21a |
| 8.351648 | 86a | 79a | 108a | 20a | 69a | 1a | 70a | 26a | 24a | 36a | 94a | 104a |
| 8.351648 | 86a | 79a | 13a | 108a | 76a | 69a | 1a | 70a | 36a | 104a | 21a | 97a |
| 8.351648 | 79a | 108a | 76a | 20a | 69a | 1a | 70a | 26a | 36a | 94a | 104a | 21a |
| 8.351648 | 79a | 13a | 76a | 69a | 1a | 70a | 26a | 24a | 36a | 94a | 21a | 97a |
| 8.351648 | 79a | 13a | 108a | 76a | 1a | 70a | 26a | 24a | 36a | 94a | 104a | 97a |
| 8.351648 | 79a | 13a | 108a | 69a | 1a | 70a | 26a | 36a | 94a | 104a | 21a | 97a |
| 8.351648 | 86a | 79a | 13a | 108a | 76a | 20a | 1a | 70a | 36a | 104a | 21a | 97a |
| 8.424909 | 86a | 79a | 13a | 20a | 69a | 70a | 26a | 36a | 94a | 104a | 21a | 97a |
| 8.424909 | 79a | 13a | 108a | 20a | 69a | 1a | 70a | 26a | 24a | 36a | 94a | 104a |
| 8.424909 | 86a | 13a | 76a | 20a | 69a | 70a | 26a | 36a | 94a | 104a | 21a | 97a |
| 8.424909 | 86a | 79a | 13a | 108a | 76a | 20a | 69a | 1a | 26a | 36a | 104a | 21a |
| 8.424909 | 86a | 13a | 108a | 76a | 20a | 69a | 70a | 26a | 24a | 36a | 104a | 97a |
| 8.424909 | 86a | 79a | 13a | 108a | 76a | 69a | 70a | 26a | 24a | 36a | 104a | 97a |
| 8.424909 | 86a | 79a | 13a | 108a | 20a | 69a | 26a | 24a | 36a | 94a | 104a | 97a |
| 8.424909 | 86a | 79a | 13a | 108a | 76a | 69a | 70a | 26a | 24a | 104a | 21a | 97a |
| 8.424909 | 86a | 79a | 13a | 108a | 69a | 1a | 70a | 26a | 36a | 94a | 104a | 97a |
| 8.424909 | 86a | 79a | 108a | 76a | 20a | 69a | 1a | 26a | 36a | 94a | 104a | 97a |
| 8.424909 | 86a | 79a | 13a | 108a | 20a | 69a | 1a | 70a | 26a | 24a | 36a | 104a |
| 8.424909 | 86a | 79a | 13a | 108a | 76a | 69a | 1a | 70a | 26a | 36a | 104a | 21a |
| 8.498169 | 79a | 13a | 76a | 1a | 70a | 26a | 24a | 36a | 94a | 104a | 21a | 97a |
| 8.498169 | 86a | 79a | 13a | 108a | 76a | 69a | 1a | 70a | 26a | 36a | 21a | 97a |
| 8.498169 | 86a | 13a | 108a | 20a | 69a | 1a | 70a | 26a | 24a | 36a | 104a | 97a |
| 8.498169 | 86a | 79a | 108a | 76a | 69a | 1a | 26a | 36a | 94a | 104a | 21a | 97a |
| 8.498169 | 86a | 13a | 76a | 20a | 69a | 1a | 70a | 26a | 24a | 36a | 104a | 97a |
| 8.498169 | 86a | 79a | 76a | 20a | 1a | 70a | 26a | 36a | 94a | 104a | 21a | 97a |
| 8.498169 | 79a | 13a | 108a | 76a | 69a | 1a | 26a | 24a | 94a | 104a | 21a | 97a |
| 8.498169 | 86a | 79a | 108a | 76a | 20a | 69a | 1a | 26a | 24a | 36a | 94a | 97a |
| 8.498169 | 79a | 13a | 108a | 76a | 20a | 69a | 1a | 26a | 36a | 94a | 104a | 97a |
| 8.498169 | 86a | 108a | 69a | 1a | 70a | 26a | 24a | 36a | 94a | 104a | 21a | 97a |
| 8.498169 | 79a | 13a | 108a | 20a | 69a | 70a | 26a | 24a | 36a | 94a | 104a | 97a |
| 8.498169 | 86a | 79a | 108a | 69a | 1a | 70a | 26a | 24a | 94a | 104a | 21a | 97a |
| 8.571428 | 86a | 79a | 13a | 108a | 76a | 70a | 24a | 36a | 94a | 104a | 21a | 97a |
| 8.571428 | 86a | 79a | 108a | 76a | 20a | 69a | 1a | 70a | 26a | 36a | 104a | 21a |
| 8.571428 | 86a | 79a | 13a | 108a | 20a | 69a | 70a | 36a | 94a | 104a | 21a | 97a |
| 8.571428 | 79a | 13a | 108a | 76a | 20a | 1a | 70a | 26a | 24a | 36a | 104a | 97a |
| 8.571428 | 79a | 13a | 76a | 69a | 70a | 26a | 24a | 36a | 94a | 104a | 21a | 97a |
| 8.571428 | 79a | 13a | 108a | 76a | 69a | 70a | 26a | 24a | 36a | 94a | 104a | 21a |
| 8.571428 | 86a | 79a | 13a | 76a | 20a | 69a | 1a | 70a | 26a | 36a | 21a | 97a |
| 8.571428 | 86a | 79a | 13a | 108a | 1a | 70a | 26a | 24a | 36a | 94a | 104a | 97a |
| 8.571428 | 79a | 13a | 108a | 76a | 69a | 26a | 24a | 36a | 94a | 104a | 21a | 97a |
| 8.571428 | 79a | 13a | 108a | 76a | 20a | 1a | 70a | 26a | 36a | 94a | 104a | 97a |
| 8.644689 | 86a | 79a | 108a | 76a | 20a | 69a | 1a | 26a | 94a | 104a | 21a | 97a |
| 8.644689 | 86a | 79a | 76a | 20a | 69a | 1a | 70a | 26a | 36a | 94a | 104a | 21a |
| 8.644689 | 86a | 13a | 76a | 20a | 69a | 70a | 26a | 24a | 36a | 94a | 104a | 97a |
| 8.644689 | 86a | 13a | 108a | 69a | 1a | 70a | 26a | 24a | 36a | 94a | 104a | 21a |
| 8.644689 | 86a | 79a | 13a | 108a | 69a | 1a | 70a | 26a | 24a | 36a | 94a | 21a |
| 8.644689 | 86a | 79a | 108a | 76a | 20a | 69a | 1a | 26a | 24a | 36a | 104a | 97a |
| 8.644689 | 86a | 79a | 13a | 76a | 20a | 69a | 1a | 70a | 36a | 94a | 104a | 97a |
| 8.644689 | 86a | 79a | 108a | 76a | 20a | 69a | 1a | 26a | 36a | 94a | 104a | 21a |
| 8.644689 | 86a | 79a | 13a | 108a | 76a | 20a | 70a | 26a | 24a | 36a | 104a | 97a |
| 8.644689 | 86a | 13a | 108a | 76a | 69a | 1a | 24a | 36a | 94a | 104a | 21a | 97a |
| 8.644689 | 79a | 13a | 76a | 20a | 69a | 1a | 26a | 36a | 94a | 104a | 21a | 97a |
| 8.644689 | 79a | 13a | 108a | 76a | 69a | 1a | 70a | 24a | 36a | 94a | 104a | 21a |
| 8.644689 | 13a | 108a | 76a | 20a | 69a | 70a | 26a | 24a | 36a | 94a | 104a | 97a |
| 8.717949 | 86a | 79a | 108a | 76a | 20a | 69a | 26a | 36a | 94a | 104a | 21a | 97a |
| 8.717949 | 86a | 108a | 20a | 69a | 1a | 70a | 26a | 36a | 94a | 104a | 21a | 97a |
| 8.717949 | 86a | 79a | 13a | 108a | 76a | 69a | 1a | 26a | 36a | 94a | 104a | 97a |
| 8.717949 | 86a | 79a | 13a | 108a | 69a | 1a | 70a | 26a | 24a | 36a | 104a | 97a |
| 8.717949 | 79a | 13a | 108a | 20a | 69a | 70a | 26a | 36a | 94a | 104a | 21a | 97a |
| 8.717949 | 86a | 79a | 76a | 20a | 69a | 1a | 26a | 36a | 94a | 104a | 21a | 97a |
| 8.717949 | 86a | 79a | 13a | 108a | 76a | 69a | 1a | 26a | 24a | 94a | 104a | 97a |
| 8.717949 | 86a | 13a | 108a | 76a | 69a | 70a | 26a | 24a | 36a | 104a | 21a | 97a |
| 8.717949 | 86a | 79a | 13a | 76a | 20a | 69a | 1a | 26a | 94a | 104a | 21a | 97a |
| 8.717949 | 79a | 13a | 108a | 76a | 20a | 1a | 70a | 26a | 36a | 104a | 21a | 97a |
| 8.791209 | 86a | 79a | 13a | 20a | 69a | 1a | 70a | 26a | 24a | 36a | 104a | 97a |
| 8.791209 | 86a | 79a | 13a | 108a | 76a | 69a | 1a | 70a | 24a | 36a | 104a | 21a |
| 8.791209 | 79a | 108a | 76a | 20a | 1a | 70a | 26a | 24a | 36a | 94a | 104a | 97a |
| 8.791209 | 86a | 79a | 13a | 108a | 76a | 1a | 26a | 24a | 36a | 104a | 21a | 97a |
| 8.791209 | 86a | 13a | 108a | 76a | 70a | 26a | 24a | 36a | 94a | 104a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 8.791209 | 79a | 13a | 108a | 76a | 20a | 69a | 70a | 26a | 36a | 94a | 104a | 97a |
| 8.791209 | 86a | 79a | 13a | 108a | 76a | 69a | 1a | 26a | 24a | 36a | 21a | 97a |
| 8.791209 | 86a | 13a | 108a | 76a | 69a | 70a | 24a | 36a | 94a | 104a | 21a | 97a |
| 8.791209 | 86a | 79a | 13a | 108a | 76a | 69a | 1a | 26a | 24a | 36a | 104a | 97a |
| 8.791209 | 86a | 13a | 108a | 20a | 69a | 1a | 70a | 26a | 36a | 104a | 21a | 97a |
| 8.791209 | 13a | 108a | 76a | 69a | 1a | 70a | 26a | 24a | 36a | 94a | 104a | 21a |
| 8.791209 | 86a | 13a | 108a | 76a | 20a | 69a | 1a | 26a | 24a | 36a | 104a | 97a |
| 8.791209 | 79a | 13a | 108a | 76a | 69a | 1a | 70a | 26a | 24a | 94a | 104a | 21a |
| 8.791209 | 86a | 13a | 108a | 76a | 20a | 1a | 70a | 26a | 36a | 104a | 21a | 97a |
| 8.791209 | 86a | 79a | 13a | 76a | 20a | 69a | 70a | 36a | 94a | 104a | 21a | 97a |
| 8.791209 | 79a | 13a | 108a | 20a | 1a | 70a | 26a | 36a | 94a | 104a | 21a | 97a |
| 8.791209 | 86a | 79a | 13a | 108a | 76a | 1a | 70a | 26a | 24a | 36a | 94a | 104a |
| 8.864469 | 86a | 79a | 13a | 108a | 76a | 1a | 26a | 24a | 36a | 94a | 104a | 97a |
| 8.864469 | 86a | 79a | 13a | 69a | 1a | 70a | 26a | 24a | 36a | 94a | 21a | 97a |
| 8.864469 | 86a | 79a | 13a | 76a | 20a | 69a | 1a | 70a | 26a | 104a | 21a | 97a |
| 8.864469 | 86a | 79a | 13a | 108a | 76a | 69a | 70a | 36a | 94a | 104a | 21a | 97a |
| 8.864469 | 79a | 76a | 69a | 1a | 70a | 26a | 24a | 36a | 94a | 104a | 21a | 97a |
| 8.864469 | 86a | 79a | 13a | 108a | 69a | 1a | 70a | 26a | 36a | 94a | 104a | 21a |
| 8.864469 | 86a | 79a | 13a | 76a | 20a | 1a | 70a | 26a | 24a | 36a | 104a | 97a |
| 8.864469 | 86a | 79a | 108a | 76a | 69a | 1a | 70a | 26a | 24a | 36a | 104a | 97a |
| 8.864469 | 79a | 13a | 108a | 76a | 20a | 69a | 1a | 26a | 24a | 36a | 94a | 104a |
| 8.864469 | 86a | 79a | 13a | 108a | 76a | 1a | 24a | 36a | 94a | 104a | 21a | 97a |
| 8.864469 | 79a | 108a | 76a | 20a | 69a | 1a | 26a | 36a | 94a | 104a | 21a | 97a |
| 8.864469 | 86a | 79a | 13a | 108a | 76a | 20a | 70a | 36a | 94a | 104a | 21a | 97a |
| 8.937729 | 79a | 108a | 76a | 1a | 70a | 26a | 24a | 36a | 94a | 104a | 21a | 97a |
| 8.937729 | 86a | 79a | 108a | 76a | 69a | 1a | 26a | 24a | 36a | 94a | 21a | 97a |
| 8.937729 | 86a | 79a | 13a | 76a | 20a | 69a | 70a | 26a | 36a | 104a | 21a | 97a |
| 8.937729 | 86a | 79a | 13a | 76a | 20a | 69a | 1a | 26a | 24a | 36a | 94a | 104a |
| 8.937729 | 86a | 79a | 20a | 69a | 1a | 70a | 26a | 24a | 36a | 94a | 104a | 97a |
| 8.937729 | 86a | 79a | 13a | 108a | 69a | 1a | 70a | 26a | 24a | 36a | 21a | 97a |
| 8.937729 | 86a | 79a | 13a | 76a | 69a | 1a | 26a | 24a | 36a | 94a | 104a | 97a |
| 8.937729 | 86a | 108a | 76a | 20a | 1a | 70a | 26a | 36a | 94a | 104a | 21a | 97a |
| 8.937729 | 86a | 79a | 13a | 108a | 76a | 69a | 1a | 26a | 94a | 104a | 21a | 97a |
| 8.937729 | 86a | 13a | 108a | 76a | 20a | 1a | 70a | 26a | 36a | 94a | 104a | 97a |
| 8.937729 | 86a | 79a | 13a | 108a | 76a | 20a | 70a | 26a | 36a | 104a | 21a | 97a |
| 8.937729 | 86a | 79a | 13a | 108a | 76a | 1a | 26a | 36a | 94a | 104a | 21a | 97a |
| 8.937729 | 79a | 13a | 108a | 76a | 69a | 1a | 70a | 26a | 24a | 36a | 21a | 97a |
| 8.937729 | 86a | 13a | 108a | 76a | 20a | 1a | 26a | 24a | 36a | 94a | 104a | 97a |
| 8.937729 | 86a | 79a | 13a | 108a | 20a | 69a | 70a | 26a | 24a | 36a | 104a | 97a |
| 9.010989 | 86a | 79a | 13a | 108a | 20a | 69a | 1a | 70a | 26a | 36a | 94a | 104a |
| 9.010989 | 86a | 79a | 13a | 108a | 69a | 1a | 70a | 24a | 36a | 104a | 21a | 97a |
| 9.010989 | 13a | 108a | 76a | 20a | 69a | 1a | 70a | 26a | 36a | 94a | 104a | 97a |
| 9.010989 | 79a | 13a | 108a | 76a | 20a | 69a | 1a | 70a | 26a | 36a | 94a | 97a |
| 9.010989 | 79a | 13a | 20a | 69a | 1a | 70a | 26a | 24a | 36a | 94a | 104a | 97a |
| 9.084249 | 86a | 79a | 13a | 108a | 20a | 69a | 1a | 26a | 24a | 36a | 94a | 104a |
| 9.084249 | 13a | 108a | 76a | 69a | 1a | 26a | 24a | 36a | 94a | 104a | 21a | 97a |
| 9.084249 | 79a | 13a | 108a | 76a | 20a | 69a | 1a | 26a | 36a | 94a | 104a | 21a |
| 9.084249 | 86a | 13a | 76a | 20a | 69a | 1a | 70a | 26a | 36a | 36a | 104a | 21a | 97a |
| 9.084249 | 86a | 79a | 13a | 108a | 1a | 70a | 26a | 36a | 94a | 104a | 21a | 97a |
| 9.084249 | 79a | 13a | 108a | 20a | 69a | 1a | 26a | 24a | 36a | 94a | 104a | 97a |
| 9.084249 | 86a | 13a | 108a | 76a | 69a | 1a | 70a | 26a | 24a | 104a | 21a | 97a |
| 9.084249 | 86a | 79a | 108a | 76a | 20a | 69a | 1a | 26a | 36a | 94a | 21a | 97a |
| 9.084249 | 79a | 13a | 108a | 1a | 70a | 26a | 24a | 36a | 94a | 104a | 21a | 97a |
| 9.084249 | 79a | 13a | 108a | 69a | 1a | 70a | 26a | 24a | 36a | 94a | 21a | 97a |
| 9.157509 | 86a | 79a | 13a | 76a | 20a | 69a | 26a | 24a | 36a | 94a | 104a | 97a |
| 9.157509 | 86a | 13a | 108a | 69a | 1a | 70a | 26a | 24a | 36a | 104a | 21a | 97a |
| 9.157509 | 86a | 79a | 13a | 108a | 76a | 69a | 1a | 24a | 36a | 104a | 21a | 97a |
| 9.157509 | 86a | 79a | 13a | 76a | 20a | 69a | 1a | 70a | 26a | 36a | 104a | 21a |
| 9.157509 | 86a | 79a | 13a | 76a | 69a | 70a | 24a | 36a | 94a | 104a | 21a | 97a |
| 9.157509 | 86a | 108a | 76a | 20a | 69a | 1a | 26a | 36a | 94a | 104a | 21a | 97a |
| 9.157509 | 86a | 79a | 13a | 108a | 20a | 69a | 70a | 26a | 36a | 94a | 104a | 21a |
| 9.157509 | 86a | 79a | 108a | 76a | 20a | 1a | 70a | 26a | 36a | 94a | 104a | 97a |
| 9.157509 | 86a | 79a | 13a | 108a | 76a | 1a | 70a | 26a | 24a | 36a | 104a | 97a |
| 9.157509 | 79a | 13a | 108a | 76a | 20a | 1a | 70a | 26a | 36a | 94a | 104a |
| 9.157509 | 86a | 79a | 13a | 76a | 69a | 1a | 26a | 24a | 36a | 94a | 21a | 97a |
| 9.230769 | 86a | 79a | 13a | 76a | 69a | 1a | 70a | 26a | 24a | 36a | 104a | 97a |
| 9.230769 | 86a | 79a | 13a | 108a | 76a | 1a | 26a | 24a | 36a | 94a | 104a | 21a |
| 9.230769 | 86a | 79a | 13a | 108a | 76a | 69a | 1a | 24a | 104a | 21a | 97a |
| 9.230769 | 86a | 79a | 108a | 20a | 69a | 1a | 26a | 24a | 36a | 94a | 104a | 97a |
| 9.230769 | 86a | 13a | 108a | 76a | 20a | 69a | 1a | 26a | 36a | 104a | 21a | 97a |
| 9.230769 | 86a | 79a | 13a | 108a | 20a | 69a | 70a | 26a | 24a | 36a | 94a | 104a |
| 9.230769 | 86a | 13a | 76a | 20a | 69a | 1a | 70a | 26a | 36a | 94a | 104a | 97a |
| 9.230769 | 86a | 79a | 13a | 20a | 69a | 1a | 70a | 26a | 36a | 36a | 21a | 97a |
| 9.230769 | 13a | 108a | 20a | 69a | 1a | 70a | 26a | 36a | 94a | 104a | 21a | 97a |
| 9.230769 | 86a | 79a | 13a | 108a | 76a | 20a | 70a | 26a | 36a | 94a | 104a | 97a |
| 9.230769 | 86a | 79a | 13a | 108a | 76a | 69a | 70a | 24a | 94a | 104a | 21a | 97a |
| 9.230769 | 86a | 79a | 13a | 76a | 20a | 69a | 70a | 26a | 36a | 94a | 104a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 9.230769 | 86a | 79a | 108a | 76a | 20a | 1a | 70a | 26a | 36a | 94a | 104a | 21a |
| 9.230769 | 86a | 13a | 108a | 76a | 20a | 69a | 1a | 26a | 36a | 94a | 104a | 97a |
| 9.304029 | 86a | 13a | 108a | 76a | 20a | 70a | 26a | 24a | 36a | 94a | 104a | 97a |
| 9.304029 | 86a | 79a | 13a | 108a | 76a | 20a | 69a | 70a | 24a | 36a | 104a | 97a |
| 9.304029 | 86a | 79a | 13a | 69a | 1a | 70a | 26a | 24a | 94a | 104a | 21a | 97a |
| 9.304029 | 86a | 13a | 108a | 76a | 20a | 69a | 70a | 26a | 36a | 94a | 104a | 97a |
| 9.304029 | 13a | 108a | 76a | 69a | 70a | 26a | 24a | 36a | 94a | 104a | 21a | 97a |
| 9.304029 | 86a | 79a | 13a | 108a | 76a | 20a | 69a | 26a | 24a | 36a | 104a | 97a |
| 9.304029 | 86a | 79a | 13a | 108a | 76a | 20a | 69a | 1a | 70a | 36a | 104a | 97a |
| 9.304029 | 86a | 79a | 13a | 108a | 76a | 20a | 69a | 36a | 94a | 104a | 21a | 97a |
| 9.304029 | 86a | 13a | 108a | 76a | 69a | 1a | 26a | 24a | 36a | 104a | 21a | 97a |
| 9.304029 | 79a | 13a | 108a | 76a | 20a | 69a | 1a | 70a | 26a | 36a | 104a | 21a |
| 9.304029 | 86a | 79a | 13a | 108a | 76a | 1a | 70a | 26a | 36a | 104a | 21a | 97a |
| 9.304029 | 86a | 79a | 108a | 76a | 1a | 70a | 26a | 24a | 94a | 104a | 21a | 97a |
| 9.304029 | 86a | 79a | 108a | 76a | 20a | 1a | 70a | 26a | 24a | 36a | 104a | 97a |
| 9.37729 | 79a | 108a | 69a | 1a | 70a | 26a | 24a | 36a | 94a | 104a | 21a | 97a |
| 9.37729 | 86a | 13a | 76a | 20a | 69a | 1a | 26a | 24a | 36a | 94a | 104a | 97a |
| 9.37729 | 13a | 76a | 69a | 1a | 70a | 26a | 24a | 36a | 94a | 104a | 21a | 97a |
| 9.37729 | 86a | 79a | 13a | 69a | 1a | 70a | 26a | 36a | 94a | 104a | 21a | 97a |
| 9.37729 | 86a | 13a | 108a | 76a | 20a | 69a | 1a | 70a | 26a | 36a | 104a | 97a |
| 9.37729 | 86a | 79a | 13a | 76a | 20a | 1a | 70a | 26a | 36a | 94a | 104a | 97a |
| 9.37729 | 79a | 13a | 76a | 20a | 69a | 1a | 70a | 26a | 36a | 94a | 104a | 21a |
| 9.37729 | 86a | 79a | 13a | 108a | 69a | 1a | 70a | 26a | 24a | 94a | 104a | 21a |
| 9.37729 | 86a | 79a | 13a | 76a | 69a | 1a | 70a | 26a | 36a | 94a | 104a | 97a |
| 9.37729 | 86a | 79a | 13a | 76a | 20a | 1a | 70a | 26a | 36a | 104a | 21a | 97a |
| 9.37729 | 86a | 13a | 76a | 1a | 70a | 26a | 24a | 36a | 94a | 104a | 21a | 97a |
| 9.37729 | 86a | 79a | 13a | 108a | 76a | 1a | 70a | 26a | 36a | 94a | 104a | 97a |
| 9.450549 | 86a | 79a | 13a | 76a | 20a | 69a | 1a | 26a | 36a | 94a | 21a | 97a |
| 9.450549 | 79a | 13a | 108a | 20a | 1a | 70a | 26a | 24a | 36a | 94a | 104a | 97a |
| 9.450549 | 86a | 79a | 108a | 20a | 69a | 1a | 70a | 26a | 24a | 36a | 104a | 97a |
| 9.450549 | 79a | 13a | 108a | 20a | 69a | 1a | 70a | 26a | 24a | 36a | 104a | 97a |
| 9.450549 | 86a | 13a | 76a | 20a | 1a | 70a | 26a | 36a | 94a | 104a | 21a | 97a |
| 9.450549 | 86a | 79a | 13a | 69a | 70a | 26a | 24a | 36a | 94a | 104a | 21a | 97a |
| 9.450549 | 86a | 79a | 13a | 76a | 69a | 1a | 24a | 36a | 94a | 104a | 21a | 97a |
| 9.450549 | 86a | 13a | 108a | 76a | 1a | 70a | 26a | 24a | 94a | 104a | 21a | 97a |
| 9.523809 | 86a | 79a | 108a | 20a | 69a | 70a | 26a | 36a | 94a | 104a | 21a | 97a |
| 9.523809 | 86a | 79a | 13a | 108a | 69a | 70a | 26a | 24a | 94a | 104a | 21a | 97a |
| 9.523809 | 86a | 79a | 108a | 76a | 69a | 1a | 26a | 24a | 36a | 104a | 21a | 97a |
| 9.523809 | 86a | 79a | 13a | 76a | 20a | 69a | 1a | 70a | 26a | 104a | 21a | 97a |
| 9.59707 | 79a | 13a | 108a | 76a | 20a | 1a | 26a | 24a | 36a | 94a | 104a | 97a |
| 9.59707 | 86a | 13a | 76a | 20a | 69a | 1a | 26a | 36a | 94a | 104a | 21a | 97a |
| 9.67033 | 86a | 79a | 108a | 76a | 69a | 1a | 70a | 26a | 36a | 94a | 104a | 97a |
| 9.67033 | 86a | 79a | 13a | 108a | 76a | 20a | 1a | 26a | 24a | 36a | 94a | 104a |
| 9.67033 | 86a | 79a | 13a | 108a | 20a | 1a | 70a | 26a | 36a | 94a | 104a | 21a |
| 9.67033 | 86a | 79a | 13a | 108a | 69a | 1a | 26a | 36a | 94a | 104a | 21a | 97a |
| 9.67033 | 79a | 13a | 108a | 20a | 69a | 1a | 70a | 26a | 36a | 94a | 104a | 21a |
| 9.67033 | 86a | 13a | 108a | 76a | 20a | 70a | 26a | 36a | 94a | 104a | 21a | 97a |
| 9.67033 | 86a | 79a | 76a | 20a | 69a | 1a | 70a | 26a | 36a | 94a | 21a | 97a |
| 9.67033 | 86a | 13a | 76a | 20a | 1a | 70a | 26a | 24a | 36a | 94a | 104a | 97a |
| 9.67033 | 86a | 79a | 13a | 108a | 76a | 69a | 1a | 26a | 24a | 36a | 94a | 21a |
| 9.67033 | 86a | 79a | 13a | 108a | 70a | 26a | 24a | 36a | 94a | 104a | 21a | 97a |
| 9.67033 | 86a | 79a | 13a | 108a | 20a | 69a | 70a | 26a | 36a | 104a | 21a | 97a |
| 9.67033 | 86a | 79a | 13a | 108a | 20a | 69a | 1a | 26a | 24a | 36a | 104a | 97a |
| 9.743589 | 86a | 79a | 13a | 108a | 69a | 1a | 26a | 24a | 94a | 104a | 21a | 97a |
| 9.743589 | 86a | 79a | 13a | 108a | 76a | 69a | 26a | 24a | 36a | 104a | 21a | 97a |
| 9.743589 | 86a | 79a | 13a | 20a | 69a | 1a | 70a | 26a | 24a | 36a | 94a | 104a |
| 9.743589 | 86a | 79a | 13a | 108a | 20a | 69a | 1a | 26a | 36a | 94a | 104a | 97a |
| 9.743589 | 86a | 79a | 13a | 76a | 69a | 70a | 26a | 24a | 94a | 104a | 21a | 97a |
| 9.81685 | 86a | 79a | 108a | 76a | 1a | 70a | 26a | 24a | 36a | 94a | 104a | 97a |
| 9.81685 | 86a | 13a | 108a | 20a | 69a | 1a | 70a | 26a | 36a | 94a | 104a | 97a |
| 9.81685 | 86a | 79a | 108a | 20a | 69a | 1a | 70a | 26a | 36a | 94a | 104a | 97a |
| 9.81685 | 86a | 79a | 13a | 76a | 69a | 1a | 70a | 26a | 24a | 36a | 21a | 97a |
| 9.81685 | 86a | 79a | 13a | 108a | 76a | 20a | 26a | 36a | 94a | 104a | 21a | 97a |
| 9.81685 | 86a | 13a | 76a | 69a | 70a | 26a | 24a | 36a | 94a | 104a | 21a | 97a |
| 9.81685 | 86a | 79a | 13a | 108a | 1a | 70a | 26a | 24a | 36a | 94a | 104a | 21a |
| 9.81685 | 86a | 79a | 13a | 108a | 76a | 20a | 69a | 70a | 36a | 94a | 104a | 97a |
| 9.81685 | 86a | 79a | 13a | 108a | 76a | 20a | 1a | 26a | 24a | 36a | 104a | 97a |
| 9.81685 | 86a | 79a | 13a | 108a | 20a | 69a | 70a | 26a | 36a | 94a | 104a | 97a |
| 9.81685 | 79a | 13a | 108a | 76a | 1a | 26a | 24a | 36a | 94a | 104a | 21a | 97a |
| 9.89011 | 86a | 79a | 76a | 69a | 1a | 70a | 26a | 36a | 94a | 104a | 21a | 97a |
| 9.89011 | 86a | 79a | 13a | 108a | 76a | 20a | 69a | 26a | 36a | 104a | 21a | 97a |
| 9.89011 | 86a | 13a | 108a | 1a | 70a | 26a | 24a | 36a | 94a | 104a | 21a | 97a |
| 9.89011 | 86a | 79a | 13a | 20a | 69a | 1a | 70a | 26a | 36a | 94a | 104a | 97a |
| 9.89011 | 86a | 13a | 108a | 76a | 20a | 69a | 26a | 24a | 36a | 94a | 104a | 97a |
| 9.89011 | 86a | 79a | 13a | 108a | 76a | 69a | 1a | 26a | 24a | 36a | 104a | 21a |
| 9.89011 | 79a | 13a | 76a | 20a | 69a | 1a | 70a | 26a | 36a | 104a | 21a | 97a |
| 9.89011 | 86a | 108a | 20a | 69a | 1a | 70a | 26a | 36a | 94a | 104a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 9.96337 | 86a | 79a | 76a | 69a | 1a | 70a | 26a | 24a | 36a | 104a | 21a | 97a |
| 9.96337 | 79a | 13a | 108a | 20a | 69a | 1a | 70a | 26a | 36a | 94a | 104a | 97a |
| 9.96337 | 86a | 79a | 108a | 76a | 69a | 1a | 26a | 24a | 36a | 94a | 104a | 21a |
| 10.03663 | 13a | 108a | 20a | 69a | 1a | 70a | 26a | 24a | 36a | 94a | 104a | 97a |
| 10.03663 | 86a | 79a | 13a | 108a | 69a | 26a | 24a | 36a | 94a | 104a | 21a | 97a |
| 10.03663 | 86a | 79a | 108a | 69a | 1a | 70a | 26a | 24a | 36a | 94a | 104a | 21a |
| 10.03663 | 86a | 79a | 13a | 108a | 1a | 70a | 26a | 24a | 36a | 104a | 21a | 97a |
| 10.03663 | 86a | 79a | 108a | 69a | 1a | 70a | 26a | 24a | 36a | 104a | 21a | 97a |
| 10.03663 | 86a | 13a | 108a | 76a | 1a | 26a | 24a | 36a | 94a | 104a | 21a | 97a |
| 10.03663 | 79a | 13a | 108a | 69a | 70a | 26a | 24a | 36a | 94a | 104a | 21a | 97a |
| 10.03663 | 86a | 79a | 13a | 108a | 76a | 1a | 26a | 24a | 94a | 104a | 21a | 97a |
| 10.10989 | 86a | 79a | 13a | 108a | 20a | 69a | 26a | 36a | 94a | 104a | 21a | 97a |
| 10.10989 | 86a | 79a | 13a | 108a | 76a | 20a | 1a | 26a | 36a | 94a | 104a | 97a |
| 10.10989 | 86a | 79a | 13a | 20a | 1a | 70a | 26a | 36a | 94a | 104a | 21a | 97a |
| 10.10989 | 79a | 13a | 108a | 76a | 69a | 1a | 70a | 26a | 24a | 36a | 94a | 21a |
| 10.10989 | 79a | 13a | 108a | 76a | 69a | 1a | 26a | 24a | 36a | 94a | 21a | 97a |
| 10.10989 | 86a | 13a | 20a | 69a | 1a | 70a | 26a | 36a | 94a | 104a | 21a | 97a |
| 10.10989 | 79a | 108a | 20a | 69a | 1a | 70a | 26a | 36a | 94a | 104a | 21a | 97a |
| 10.18315 | 86a | 79a | 13a | 76a | 69a | 1a | 26a | 24a | 94a | 104a | 21a | 97a |
| 10.18315 | 86a | 79a | 13a | 76a | 69a | 1a | 70a | 26a | 24a | 36a | 104a | 21a |
| 10.18315 | 86a | 79a | 13a | 108a | 76a | 20a | 69a | 26a | 36a | 94a | 104a | 97a |
| 10.18315 | 86a | 79a | 108a | 20a | 69a | 1a | 70a | 26a | 36a | 94a | 104a | 21a |
| 10.18315 | 86a | 79a | 13a | 76a | 20a | 69a | 26a | 36a | 94a | 104a | 21a | 97a |
| 10.25641 | 86a | 79a | 108a | 76a | 20a | 1a | 70a | 26a | 36a | 104a | 21a | 97a |
| 10.25641 | 86a | 79a | 13a | 76a | 1a | 26a | 24a | 36a | 94a | 104a | 21a | 97a |
| 10.25641 | 86a | 79a | 108a | 76a | 1a | 70a | 26a | 36a | 94a | 104a | 21a | 97a |
| 10.25641 | 86a | 79a | 13a | 108a | 20a | 1a | 70a | 26a | 24a | 36a | 94a | 104a |
| 10.25641 | 86a | 13a | 108a | 76a | 20a | 1a | 26a | 24a | 36a | 94a | 104a | 97a |
| 10.25641 | 86a | 79a | 13a | 108a | 69a | 70a | 26a | 24a | 36a | 104a | 21a | 97a |
| 10.25641 | 79a | 108a | 76a | 20a | 69a | 1a | 70a | 26a | 36a | 104a | 21a | 97a |
| 10.25641 | 86a | 79a | 13a | 1a | 70a | 26a | 24a | 36a | 94a | 104a | 21a | 97a |
| 10.25641 | 86a | 13a | 108a | 20a | 69a | 70a | 26a | 24a | 36a | 94a | 104a | 97a |
| 10.32967 | 86a | 79a | 69a | 1a | 70a | 26a | 24a | 36a | 94a | 104a | 21a | 97a |
| 10.32967 | 86a | 79a | 13a | 108a | 76a | 20a | 69a | 70a | 36a | 104a | 21a | 97a |
| 10.32967 | 86a | 13a | 76a | 69a | 1a | 70a | 26a | 24a | 94a | 104a | 21a | 97a |
| 10.32967 | 86a | 79a | 13a | 76a | 69a | 70a | 26a | 24a | 36a | 104a | 21a | 97a |
| 10.32967 | 86a | 79a | 13a | 108a | 20a | 70a | 26a | 24a | 36a | 94a | 104a | 97a |
| 10.32967 | 86a | 79a | 13a | 108a | 69a | 70a | 24a | 36a | 94a | 104a | 21a | 97a |
| 10.32967 | 86a | 79a | 13a | 76a | 69a | 1a | 70a | 26a | 24a | 104a | 21a | 97a |
| 10.32967 | 86a | 13a | 20a | 69a | 1a | 70a | 26a | 24a | 36a | 94a | 104a | 97a |
| 10.40293 | 79a | 13a | 108a | 76a | 69a | 1a | 26a | 24a | 36a | 104a | 21a | 97a |
| 10.40293 | 79a | 13a | 108a | 76a | 1a | 70a | 24a | 36a | 94a | 104a | 21a | 97a |
| 10.40293 | 86a | 79a | 13a | 76a | 69a | 1a | 70a | 24a | 36a | 104a | 21a | 97a |
| 10.40293 | 86a | 79a | 108a | 76a | 1a | 70a | 26a | 24a | 36a | 94a | 104a | 21a |
| 10.40293 | 86a | 13a | 108a | 20a | 69a | 1a | 26a | 24a | 36a | 94a | 104a | 97a |
| 10.40293 | 86a | 13a | 108a | 20a | 1a | 70a | 26a | 24a | 36a | 94a | 104a | 97a |
| 10.47619 | 79a | 13a | 108a | 76a | 20a | 69a | 1a | 26a | 36a | 104a | 21a | 97a |
| 10.47619 | 86a | 13a | 76a | 69a | 1a | 26a | 24a | 36a | 94a | 104a | 21a | 97a |
| 10.47619 | 86a | 79a | 13a | 108a | 1a | 26a | 24a | 36a | 94a | 104a | 21a | 97a |
| 10.47619 | 86a | 79a | 13a | 76a | 20a | 69a | 1a | 26a | 24a | 36a | 104a | 97a |
| 10.47619 | 86a | 79a | 13a | 76a | 1a | 70a | 26a | 24a | 36a | 104a | 21a | 97a |
| 10.47619 | 79a | 108a | 76a | 69a | 1a | 26a | 24a | 36a | 94a | 104a | 21a | 97a |
| 10.54945 | 86a | 79a | 13a | 108a | 76a | 69a | 1a | 24a | 94a | 104a | 21a | 97a |
| 10.54945 | 86a | 13a | 108a | 20a | 69a | 70a | 26a | 36a | 94a | 104a | 21a | 97a |
| 10.54945 | 86a | 79a | 13a | 108a | 76a | 69a | 26a | 24a | 94a | 104a | 21a | 97a |
| 10.54945 | 86a | 79a | 13a | 108a | 76a | 69a | 24a | 36a | 94a | 104a | 21a | 97a |
| 10.54945 | 13a | 108a | 69a | 1a | 70a | 26a | 24a | 36a | 94a | 104a | 21a | 97a |
| 10.62271 | 86a | 79a | 108a | 76a | 20a | 1a | 26a | 24a | 36a | 94a | 104a | 97a |
| 10.62271 | 86a | 13a | 76a | 69a | 1a | 70a | 26a | 24a | 36a | 104a | 21a | 97a |
| 10.62271 | 86a | 79a | 13a | 76a | 20a | 1a | 26a | 24a | 36a | 94a | 104a | 97a |
| 10.62271 | 79a | 13a | 108a | 76a | 69a | 1a | 70a | 26a | 24a | 36a | 104a | 21a |
| 10.62271 | 86a | 79a | 13a | 76a | 20a | 1a | 26a | 36a | 94a | 104a | 21a | 97a |
| 10.62271 | 86a | 79a | 13a | 108a | 69a | 1a | 70a | 26a | 36a | 104a | 21a | 97a |
| 10.62271 | 79a | 13a | 108a | 20a | 69a | 1a | 26a | 24a | 36a | 94a | 104a | 97a |
| 10.62271 | 79a | 13a | 20a | 69a | 1a | 70a | 26a | 36a | 94a | 104a | 21a | 97a |
| 10.62271 | 86a | 79a | 13a | 76a | 20a | 69a | 1a | 70a | 26a | 94a | 104a | 97a |
| 10.69597 | 86a | 79a | 76a | 20a | 69a | 1a | 70a | 26a | 36a | 104a | 21a | 97a |
| 10.69597 | 86a | 79a | 13a | 76a | 69a | 26a | 24a | 94a | 104a | 21a | 97a | |
| 10.69597 | 86a | 79a | 13a | 108a | 76a | 20a | 1a | 26a | 36a | 104a | 21a | 97a |
| 10.69597 | 86a | 13a | 108a | 76a | 69a | 1a | 26a | 24a | 94a | 104a | 21a | 97a |
| 10.69597 | 86a | 79a | 108a | 76a | 20a | 69a | 1a | 70a | 26a | 36a | 104a | 97a |
| 10.76923 | 86a | 13a | 108a | 76a | 69a | 26a | 24a | 36a | 94a | 104a | 21a | 97a |
| 10.76923 | 86a | 79a | 13a | 108a | 20a | 1a | 26a | 24a | 36a | 94a | 104a | 97a |
| 10.76923 | 86a | 79a | 76a | 69a | 1a | 26a | 24a | 36a | 94a | 104a | 21a | 97a |
| 10.76923 | 86a | 79a | 13a | 108a | 76a | 69a | 1a | 70a | 26a | 36a | 104a | 97a |
| 10.84249 | 86a | 79a | 108a | 76a | 20a | 1a | 70a | 26a | 24a | 36a | 94a | 104a |
| 10.84249 | 86a | 79a | 13a | 20a | 69a | 1a | 26a | 24a | 36a | 94a | 104a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 10.91575 | 86a | 79a | 108a | 76a | 69a | 1a | 26a | 36a | 94a | 104a | 21a | 97a |
| 10.91575 | 86a | 79a | 13a | 20a | 1a | 70a | 26a | 24a | 94a | 104a | 21a | 97a |
| 10.98901 | 86a | 79a | 13a | 76a | 20a | 69a | 1a | 26a | 36a | 94a | 104a | 21a |
| 10.98901 | 86a | 79a | 13a | 108a | 20a | 69a | 1a | 26a | 36a | 94a | 104a | 21a |
| 10.98901 | 86a | 13a | 108a | 20a | 1a | 70a | 26a | 36a | 94a | 104a | 21a | 97a |
| 11.06227 | 86a | 79a | 13a | 76a | 20a | 69a | 1a | 26a | 36a | 94a | 104a | 97a |
| 11.06227 | 86a | 79a | 13a | 108a | 20a | 1a | 70a | 26a | 24a | 36a | 104a | 97a |
| 11.06227 | 86a | 13a | 108a | 69a | 70a | 26a | 24a | 36a | 94a | 104a | 21a | 97a |
| 11.06227 | 86a | 79a | 13a | 76a | 69a | 1a | 26a | 36a | 94a | 104a | 21a | 97a |
| 11.06227 | 86a | 79a | 108a | 69a | 1a | 26a | 24a | 36a | 94a | 104a | 21a | 97a |
| 11.06227 | 86a | 79a | 108a | 76a | 1a | 26a | 24a | 36a | 94a | 104a | 21a | 97a |
| 11.06227 | 86a | 79a | 13a | 108a | 69a | 70a | 26a | 24a | 36a | 94a | 104a | 21a |
| 11.13553 | 86a | 79a | 108a | 76a | 20a | 1a | 26a | 36a | 94a | 104a | 21a | 97a |
| 11.13553 | 86a | 13a | 108a | 76a | 20a | 69a | 26a | 36a | 94a | 104a | 21a | 97a |
| 11.13553 | 86a | 13a | 108a | 76a | 69a | 70a | 26a | 24a | 94a | 104a | 21a | 97a |
| 11.13553 | 79a | 108a | 76a | 69a | 1a | 70a | 26a | 24a | 36a | 94a | 104a | 21a |
| 11.20879 | 86a | 79a | 108a | 1a | 70a | 26a | 24a | 36a | 94a | 104a | 21a | 97a |
| 11.20879 | 86a | 79a | 13a | 76a | 20a | 69a | 1a | 70a | 26a | 36a | 104a | 97a |
| 11.20879 | 86a | 79a | 13a | 108a | 20a | 70a | 26a | 36a | 94a | 104a | 21a | 97a |
| 11.20879 | 79a | 13a | 76a | 69a | 1a | 70a | 26a | 24a | 36a | 104a | 21a | 97a |
| 11.20879 | 86a | 79a | 108a | 76a | 69a | 1a | 26a | 24a | 94a | 104a | 21a | 97a |
| 11.28205 | 86a | 79a | 13a | 108a | 20a | 69a | 1a | 70a | 26a | 36a | 104a | 21a |
| 11.28205 | 86a | 13a | 108a | 69a | 1a | 70a | 26a | 24a | 94a | 104a | 21a | 97a |
| 11.28205 | 86a | 79a | 20a | 69a | 1a | 70a | 26a | 36a | 94a | 104a | 21a | 97a |
| 11.35531 | 86a | 79a | 13a | 108a | 20a | 1a | 70a | 26a | 36a | 104a | 21a | 97a |
| 11.35531 | 86a | 79a | 13a | 108a | 69a | 1a | 26a | 24a | 36a | 104a | 21a | 97a |
| 11.35531 | 86a | 13a | 108a | 76a | 20a | 1a | 26a | 36a | 94a | 104a | 21a | 97a |
| 11.35531 | 86a | 79a | 108a | 69a | 1a | 70a | 26a | 36a | 94a | 104a | 21a | 97a |
| 11.42857 | 86a | 79a | 76a | 20a | 69a | 1a | 26a | 36a | 94a | 104a | 21a | 97a |
| 11.42857 | 86a | 79a | 13a | 108a | 20a | 1a | 70a | 26a | 36a | 94a | 104a | 97a |
| 11.50183 | 86a | 13a | 69a | 1a | 70a | 26a | 24a | 36a | 94a | 104a | 21a | 97a |
| 11.50183 | 86a | 79a | 108a | 20a | 1a | 70a | 26a | 24a | 36a | 94a | 104a | 97a |
| 11.50183 | 86a | 79a | 108a | 76a | 20a | 69a | 1a | 26a | 36a | 104a | 21a | 97a |
| 11.50183 | 86a | 79a | 13a | 108a | 76a | 69a | 1a | 26a | 36a | 94a | 104a | 97a |
| 11.57509 | 86a | 13a | 108a | 20a | 69a | 1a | 26a | 36a | 94a | 104a | 21a | 97a |
| 11.64835 | 86a | 13a | 108a | 69a | 1a | 26a | 24a | 36a | 94a | 104a | 21a | 97a |
| 11.72161 | 86a | 79a | 13a | 108a | 20a | 69a | 1a | 70a | 26a | 36a | 104a | 97a |
| 11.72161 | 86a | 79a | 13a | 20a | 69a | 1a | 70a | 26a | 36a | 104a | 21a | 97a |
| 11.72161 | 79a | 13a | 108a | 69a | 1a | 70a | 26a | 24a | 36a | 104a | 21a | 97a |
| 11.72161 | 86a | 79a | 108a | 76a | 69a | 1a | 70a | 26a | 36a | 104a | 21a | 97a |
| 11.79487 | 86a | 79a | 13a | 108a | 76a | 20a | 1a | 70a | 26a | 36a | 104a | 97a |
| 11.86813 | 79a | 13a | 108a | 20a | 69a | 1a | 70a | 26a | 36a | 104a | 21a | 97a |
| 11.94139 | 86a | 79a | 13a | 76a | 20a | 1a | 70a | 26a | 36a | 104a | 21a | 97a |
| 12.01465 | 86a | 79a | 13a | 108a | 20a | 1a | 26a | 36a | 94a | 104a | 21a | 97a |
| 12.01465 | 86a | 79a | 13a | 108a | 76a | 20a | 69a | 70a | 26a | 36a | 104a | 97a |
| 12.01465 | 86a | 79a | 13a | 108a | 76a | 69a | 70a | 24a | 36a | 104a | 21a | 97a |
| 12.08791 | 86a | 79a | 13a | 108a | 76a | 20a | 69a | 1a | 26a | 36a | 104a | 97a |
| 12.08791 | 86a | 79a | 13a | 108a | 20a | 69a | 1a | 26a | 36a | 104a | 21a | 97a |
| 12.16117 | 86a | 79a | 13a | 20a | 69a | 1a | 70a | 26a | 36a | 94a | 104a | 21a |
| 12.30769 | 86a | 79a | 108a | 20a | 69a | 1a | 70a | 26a | 36a | 104a | 21a | 97a |
| 12.45421 | 86a | 79a | 13a | 76a | 69a | 1a | 26a | 24a | 36a | 94a | 104a | 21a |
| 12.60073 | 86a | 79a | 13a | 108a | 69a | 1a | 26a | 24a | 36a | 94a | 104a | 21a |
| 12.60073 | 79a | 13a | 76a | 69a | 1a | 26a | 24a | 36a | 94a | 104a | 21a | 97a |
| 12.74725 | 86a | 79a | 13a | 108a | 69a | 1a | 70a | 26a | 24a | 36a | 104a | 21a |
| 12.74725 | 79a | 13a | 76a | 69a | 1a | 70a | 26a | 24a | 36a | 94a | 104a | 21a |
| 12.89377 | 79a | 13a | 108a | 69a | 1a | 26a | 24a | 36a | 94a | 104a | 21a | 97a |
| 12.89377 | 86a | 79a | 108a | 20a | 69a | 1a | 26a | 36a | 94a | 104a | 21a | 97a |
| 13.11355 | 86a | 79a | 13a | 20a | 69a | 1a | 26a | 36a | 94a | 104a | 21a | 97a |
| 13.18681 | 86a | 79a | 108a | 20a | 1a | 70a | 26a | 36a | 94a | 104a | 21a | 97a |
| 13.26007 | 86a | 79a | 13a | 69a | 1a | 70a | 26a | 24a | 36a | 104a | 21a | 97a |
| 13.26007 | 86a | 79a | 13a | 108a | 76a | 20a | 70a | 26a | 24a | 94a | 21a | 97a |
| 13.33333 | 86a | 79a | 13a | 69a | 1a | 70a | 26a | 24a | 36a | 94a | 104a | 21a |
| 13.62637 | 86a | 108a | 76a | 20a | 69a | 1a | 70a | 26a | 24a | 94a | 21a | 97a |
| 13.69963 | 86a | 79a | 13a | 108a | 76a | 20a | 1a | 70a | 26a | 24a | 104a | 97a |
| 13.77289 | 79a | 13a | 108a | 69a | 1a | 70a | 26a | 24a | 36a | 94a | 104a | 21a |
| 13.77289 | 86a | 79a | 13a | 108a | 76a | 20a | 1a | 70a | 26a | 24a | 104a | 21a |
| 13.77289 | 86a | 79a | 13a | 108a | 76a | 20a | 70a | 26a | 24a | 36a | 21a | 97a |
| 13.77289 | 86a | 79a | 13a | 76a | 20a | 69a | 1a | 26a | 36a | 104a | 21a | 97a |
| 13.84615 | 86a | 79a | 13a | 108a | 76a | 20a | 70a | 24a | 36a | 94a | 21a | 97a |
| 13.84615 | 86a | 108a | 76a | 20a | 69a | 1a | 70a | 24a | 36a | 94a | 21a | 97a |
| 13.84615 | 86a | 13a | 108a | 76a | 20a | 1a | 70a | 26a | 24a | 94a | 21a | 97a |
| 13.99267 | 79a | 108a | 76a | 20a | 69a | 70a | 26a | 24a | 36a | 94a | 21a | 97a |
| 13.99267 | 86a | 79a | 13a | 76a | 20a | 1a | 70a | 26a | 24a | 94a | 21a | 97a |
| 13.99267 | 86a | 108a | 76a | 20a | 69a | 1a | 70a | 26a | 24a | 36a | 21a | 97a |
| 14.06593 | 86a | 79a | 13a | 69a | 1a | 26a | 24a | 36a | 94a | 104a | 21a | 97a |
| 14.13919 | 86a | 79a | 13a | 108a | 20a | 1a | 70a | 26a | 24a | 94a | 21a | 97a |
| 14.21245 | 86a | 108a | 76a | 20a | 69a | 1a | 70a | 24a | 36a | 94a | 104a | 21a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 14.21245 | 86a | 79a | 13a | 76a | 20a | 1a | 70a | 24a | 36a | 94a | 21a | 97a |
| 14.28571 | 86a | 79a | 13a | 76a | 69a | 1a | 26a | 24a | 36a | 104a | 21a | 97a |
| 14.28571 | 86a | 13a | 108a | 76a | 20a | 69a | 1a | 26a | 24a | 36a | 21a | 97a |
| 14.28571 | 79a | 108a | 76a | 20a | 69a | 70a | 24a | 36a | 94a | 104a | 21a | 97a |
| 14.35897 | 79a | 13a | 108a | 76a | 20a | 70a | 26a | 24a | 36a | 94a | 21a | 97a |
| 14.35897 | 79a | 13a | 108a | 76a | 20a | 1a | 70a | 26a | 24a | 104a | 21a | 97a |
| 14.43223 | 86a | 79a | 108a | 20a | 69a | 1a | 70a | 24a | 36a | 94a | 21a | 97a |
| 14.43223 | 86a | 108a | 76a | 20a | 69a | 1a | 70a | 26a | 24a | 36a | 104a | 21a |
| 14.43223 | 86a | 79a | 108a | 76a | 20a | 69a | 1a | 70a | 26a | 24a | 104a | 21a |
| 14.50549 | 86a | 79a | 108a | 20a | 69a | 1a | 70a | 26a | 24a | 94a | 21a | 97a |
| 14.50549 | 86a | 79a | 13a | 108a | 20a | 1a | 70a | 24a | 36a | 94a | 21a | 97a |
| 14.57875 | 86a | 13a | 108a | 76a | 20a | 1a | 70a | 26a | 24a | 36a | 21a | 97a |
| 14.57875 | 79a | 13a | 69a | 1a | 70a | 26a | 24a | 36a | 94a | 104a | 21a | 97a |
| 14.57875 | 79a | 108a | 76a | 20a | 69a | 1a | 70a | 26a | 24a | 104a | 21a | 97a |
| 14.65201 | 86a | 108a | 76a | 20a | 69a | 1a | 70a | 24a | 36a | 104a | 21a | 97a |
| 14.65201 | 86a | 13a | 108a | 76a | 20a | 1a | 70a | 24a | 36a | 94a | 21a | 97a |
| 14.72528 | 86a | 79a | 13a | 108a | 76a | 20a | 1a | 26a | 24a | 36a | 21a | 97a |
| 14.72528 | 86a | 79a | 108a | 76a | 20a | 69a | 70a | 24a | 36a | 94a | 21a | 97a |
| 14.72528 | 86a | 79a | 13a | 108a | 76a | 20a | 1a | 70a | 24a | 36a | 21a | 97a |
| 14.79853 | 86a | 76a | 20a | 69a | 1a | 70a | 24a | 36a | 94a | 104a | 21a | 97a |
| 14.79853 | 86a | 13a | 108a | 76a | 20a | 69a | 1a | 70a | 24a | 36a | 94a | 21a |
| 14.79853 | 86a | 79a | 13a | 108a | 76a | 20a | 69a | 70a | 26a | 24a | 94a | 21a |
| 14.79853 | 86a | 79a | 13a | 108a | 76a | 20a | 69a | 1a | 70a | 26a | 24a | 21a |
| 14.79853 | 86a | 13a | 108a | 76a | 20a | 69a | 1a | 24a | 36a | 94a | 21a | 97a |
| 14.87179 | 108a | 76a | 20a | 69a | 1a | 70a | 26a | 24a | 36a | 94a | 21a | 97a |
| 14.87179 | 86a | 79a | 108a | 76a | 20a | 69a | 70a | 26a | 24a | 94a | 104a | 21a |
| 14.87179 | 86a | 79a | 13a | 108a | 76a | 20a | 69a | 70a | 26a | 24a | 36a | 21a |
| 14.87179 | 86a | 79a | 13a | 108a | 76a | 20a | 70a | 26a | 24a | 104a | 21a | 97a |
| 14.87179 | 86a | 79a | 76a | 20a | 69a | 1a | 70a | 24a | 36a | 94a | 104a | 21a |
| 14.94506 | 86a | 13a | 108a | 76a | 20a | 69a | 1a | 70a | 26a | 24a | 94a | 21a |
| 14.94506 | 86a | 13a | 108a | 76a | 20a | 1a | 70a | 26a | 24a | 36a | 104a | 21a |
| 14.94506 | 13a | 108a | 76a | 20a | 1a | 70a | 26a | 24a | 36a | 94a | 21a | 97a |
| 14.94506 | 86a | 13a | 108a | 76a | 20a | 69a | 1a | 70a | 26a | 24a | 36a | 21a |
| 15.01832 | 86a | 13a | 108a | 76a | 20a | 69a | 1a | 26a | 24a | 94a | 21a | 97a |
| 15.01832 | 86a | 13a | 108a | 76a | 20a | 69a | 70a | 26a | 24a | 94a | 21a | 97a |
| 15.09157 | 86a | 79a | 13a | 108a | 76a | 20a | 1a | 26a | 24a | 94a | 21a | 97a |
| 15.09157 | 108a | 76a | 20a | 69a | 1a | 70a | 26a | 24a | 36a | 94a | 104a | 21a |
| 15.16483 | 86a | 79a | 13a | 108a | 76a | 20a | 70a | 26a | 24a | 94a | 104a | 21a |
| 15.16483 | 86a | 79a | 108a | 76a | 20a | 69a | 70a | 26a | 24a | 104a | 21a | 97a |
| 15.16483 | 86a | 108a | 76a | 20a | 69a | 1a | 70a | 26a | 24a | 94a | 104a | 21a |
| 15.16483 | 86a | 79a | 13a | 108a | 76a | 20a | 69a | 70a | 24a | 36a | 94a | 21a |
| 15.16483 | 86a | 79a | 108a | 76a | 20a | 69a | 70a | 26a | 24a | 36a | 21a | 97a |
| 15.16483 | 86a | 13a | 108a | 76a | 20a | 1a | 70a | 24a | 36a | 94a | 104a | 21a |
| 15.16483 | 86a | 79a | 76a | 20a | 1a | 70a | 24a | 36a | 94a | 104a | 21a | 97a |
| 15.16483 | 86a | 79a | 13a | 108a | 76a | 20a | 1a | 24a | 36a | 94a | 21a | 97a |
| 15.2381 | 86a | 13a | 108a | 76a | 20a | 69a | 1a | 70a | 24a | 94a | 21a | 97a |
| 15.2381 | 86a | 79a | 13a | 108a | 76a | 20a | 1a | 70a | 26a | 24a | 94a | 21a |
| 15.2381 | 86a | 79a | 13a | 108a | 76a | 20a | 69a | 70a | 26a | 24a | 104a | 21a |
| 15.2381 | 86a | 79a | 13a | 108a | 76a | 20a | 69a | 70a | 24a | 94a | 104a | 21a |
| 15.2381 | 86a | 79a | 108a | 76a | 20a | 69a | 70a | 26a | 24a | 94a | 21a | 97a |
| 15.2381 | 86a | 79a | 108a | 76a | 20a | 69a | 70a | 24a | 36a | 94a | 104a | 21a |
| 15.2381 | 86a | 79a | 108a | 76a | 20a | 1a | 70a | 26a | 24a | 94a | 21a | 97a |
| 15.31136 | 86a | 108a | 76a | 20a | 69a | 1a | 70a | 24a | 94a | 104a | 21a | 97a |
| 15.31136 | 79a | 13a | 108a | 76a | 20a | 69a | 70a | 26a | 24a | 36a | 94a | 21a |
| 15.31136 | 79a | 13a | 108a | 76a | 20a | 70a | 24a | 36a | 94a | 104a | 21a | 97a |
| 15.31136 | 86a | 79a | 13a | 76a | 20a | 1a | 70a | 26a | 24a | 36a | 21a | 97a |
| 15.38461 | 86a | 79a | 108a | 76a | 20a | 69a | 1a | 70a | 26a | 24a | 94a | 21a |
| 15.38461 | 86a | 13a | 108a | 76a | 20a | 69a | 70a | 26a | 24a | 94a | 21a | 97a |
| 15.38461 | 79a | 108a | 20a | 69a | 1a | 70a | 24a | 36a | 94a | 104a | 21a | 97a |
| 15.38461 | 86a | 13a | 108a | 76a | 20a | 1a | 70a | 26a | 24a | 94a | 104a | 21a |
| 15.38461 | 86a | 79a | 13a | 76a | 20a | 69a | 1a | 70a | 26a | 24a | 94a | 21a |
| 15.38461 | 86a | 79a | 13a | 108a | 76a | 20a | 1a | 70a | 26a | 24a | 36a | 21a |
| 15.38461 | 86a | 108a | 76a | 20a | 69a | 70a | 26a | 24a | 36a | 104a | 21a | 97a |
| 15.38461 | 86a | 79a | 13a | 76a | 20a | 69a | 1a | 70a | 24a | 36a | 94a | 21a |
| 15.38461 | 79a | 76a | 20a | 69a | 1a | 70a | 24a | 36a | 94a | 104a | 21a | 97a |
| 15.45788 | 86a | 79a | 13a | 76a | 20a | 1a | 70a | 24a | 36a | 94a | 104a | 21a |
| 15.45788 | 86a | 79a | 108a | 76a | 20a | 69a | 70a | 26a | 24a | 36a | 104a | 21a |
| 15.45788 | 86a | 13a | 108a | 76a | 20a | 69a | 1a | 70a | 24a | 94a | 104a | 21a |
| 15.45788 | 79a | 13a | 108a | 76a | 20a | 69a | 26a | 24a | 36a | 94a | 21a | 97a |
| 15.45788 | 86a | 108a | 76a | 20a | 69a | 1a | 70a | 26a | 24a | 104a | 21a | 97a |
| 15.45788 | 86a | 13a | 76a | 20a | 69a | 1a | 70a | 24a | 36a | 94a | 21a | 97a |
| 15.45788 | 79a | 108a | 76a | 20a | 69a | 1a | 70a | 24a | 36a | 94a | 21a | 97a |
| 15.45788 | 86a | 13a | 108a | 76a | 20a | 69a | 70a | 26a | 24a | 36a | 21a | 97a |
| 15.53114 | 86a | 13a | 108a | 76a | 20a | 69a | 1a | 70a | 26a | 24a | 104a | 21a |
| 15.53114 | 86a | 108a | 76a | 20a | 69a | 70a | 24a | 36a | 94a | 104a | 21a | 97a |
| 15.53114 | 79a | 13a | 108a | 76a | 20a | 1a | 70a | 26a | 24a | 94a | 21a | 97a |
| 15.53114 | 79a | 108a | 76a | 20a | 69a | 70a | 26a | 24a | 36a | 94a | 104a | 21a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 15.53114 | 86a | 79a | 13a | 108a | 76a | 20a | 1a | 70a | 24a | 94a | 21a | 97a |
| 15.53114 | 86a | 79a | 108a | 76a | 20a | 69a | 1a | 70a | 24a | 36a | 94a | 21a |
| 15.53114 | 79a | 108a | 76a | 20a | 69a | 1a | 70a | 24a | 36a | 104a | 21a | 97a |
| 15.53114 | 79a | 13a | 108a | 76a | 20a | 69a | 1a | 26a | 24a | 104a | 21a | 97a |
| 15.53114 | 79a | 13a | 108a | 76a | 20a | 69a | 1a | 70a | 26a | 24a | 104a | 21a |
| 15.53114 | 79a | 13a | 108a | 76a | 20a | 69a | 70a | 24a | 94a | 104a | 21a | 97a |
| 15.6044 | 86a | 79a | 108a | 76a | 20a | 69a | 1a | 70a | 26a | 24a | 21a | 97a |
| 15.6044 | 86a | 13a | 108a | 20a | 69a | 1a | 70a | 26a | 24a | 36a | 21a | 97a |
| 15.6044 | 86a | 79a | 13a | 108a | 76a | 20a | 69a | 1a | 70a | 24a | 36a | 21a |
| 15.6044 | 13a | 108a | 76a | 20a | 69a | 1a | 26a | 24a | 36a | 94a | 21a | 97a |
| 15.6044 | 86a | 79a | 13a | 108a | 76a | 20a | 1a | 70a | 24a | 36a | 94a | 21a |
| 15.6044 | 79a | 13a | 76a | 20a | 1a | 70a | 24a | 36a | 94a | 104a | 21a | 97a |
| 15.6044 | 86a | 79a | 13a | 108a | 20a | 69a | 1a | 24a | 36a | 94a | 21a | 97a |
| 15.6044 | 13a | 108a | 76a | 20a | 69a | 1a | 70a | 24a | 94a | 104a | 21a | 97a |
| 15.6044 | 86a | 79a | 108a | 76a | 20a | 69a | 1a | 70a | 24a | 36a | 21a | 97a |
| 15.67766 | 86a | 79a | 13a | 108a | 76a | 20a | 69a | 1a | 26a | 24a | 104a | 21a |
| 15.67766 | 86a | 13a | 76a | 20a | 69a | 1a | 70a | 26a | 24a | 94a | 21a | 97a |
| 15.67766 | 86a | 79a | 13a | 76a | 20a | 69a | 1a | 70a | 26a | 24a | 104a | 21a |
| 15.67766 | 86a | 79a | 76a | 20a | 69a | 1a | 70a | 26a | 24a | 94a | 21a | 97a |
| 15.67766 | 86a | 79a | 13a | 108a | 20a | 69a | 1a | 70a | 26a | 24a | 21a | 97a |
| 15.67766 | 86a | 79a | 108a | 76a | 20a | 69a | 70a | 26a | 24a | 36a | 94a | 21a |
| 15.67766 | 86a | 79a | 13a | 108a | 20a | 1a | 70a | 26a | 24a | 36a | 21a | 97a |
| 15.75092 | 86a | 13a | 108a | 20a | 69a | 1a | 70a | 24a | 36a | 94a | 21a | 97a |
| 15.75092 | 86a | 79a | 13a | 108a | 20a | 69a | 1a | 70a | 24a | 94a | 21a | 97a |
| 15.75092 | 13a | 108a | 76a | 20a | 1a | 70a | 24a | 36a | 94a | 104a | 21a | 97a |
| 15.75092 | 79a | 13a | 108a | 20a | 1a | 70a | 24a | 36a | 94a | 104a | 21a | 97a |
| 15.75092 | 79a | 13a | 108a | 76a | 20a | 70a | 26a | 24a | 94a | 104a | 21a | 97a |
| 15.75092 | 86a | 79a | 76a | 20a | 69a | 70a | 24a | 36a | 94a | 104a | 21a | 97a |
| 15.75092 | 86a | 13a | 108a | 76a | 20a | 69a | 1a | 70a | 24a | 36a | 21a | 97a |
| 15.75092 | 86a | 13a | 108a | 20a | 69a | 1a | 70a | 26a | 24a | 94a | 21a | 97a |
| 15.75092 | 86a | 13a | 108a | 76a | 20a | 69a | 1a | 70a | 26a | 24a | 21a | 97a |
| 15.75092 | 86a | 79a | 13a | 108a | 20a | 69a | 1a | 70a | 24a | 36a | 21a | 97a |
| 15.75092 | 79a | 13a | 76a | 20a | 1a | 70a | 26a | 24a | 36a | 94a | 21a | 97a |
| 15.75092 | 79a | 13a | 76a | 20a | 69a | 1a | 70a | 24a | 36a | 94a | 21a | 97a |
| 15.82418 | 86a | 79a | 108a | 76a | 20a | 1a | 70a | 26a | 24a | 36a | 104a | 21a |
| 15.82418 | 79a | 13a | 108a | 76a | 20a | 69a | 70a | 24a | 36a | 94a | 21a | 97a |
| 15.82418 | 13a | 108a | 76a | 20a | 1a | 70a | 26a | 24a | 94a | 104a | 21a | 97a |
| 15.82418 | 86a | 79a | 20a | 69a | 1a | 70a | 24a | 36a | 94a | 104a | 21a | 97a |
| 15.82418 | 79a | 13a | 108a | 76a | 20a | 1a | 24a | 36a | 94a | 104a | 21a | 97a |
| 15.82418 | 86a | 79a | 13a | 108a | 76a | 20a | 70a | 26a | 24a | 36a | 104a | 21a |
| 15.82418 | 108 | 76a | 20a | 69a | 1a | 70a | 26a | 24a | 94a | 104a | 21a | 97a |
| 15.82418 | 86a | 13a | 76a | 20a | 69a | 1a | 70a | 26a | 24a | 36a | 21a | 97a |
| 15.82418 | 86a | 79a | 76a | 20a | 1a | 70a | 24a | 36a | 94a | 21a | 97a | |
| 15.82418 | 86a | 79a | 76a | 20a | 69a | 1a | 70a | 26a | 24a | 94a | 104a | 21a |
| 15.82418 | 86a | 79a | 108a | 76a | 20a | 1a | 70a | 24a | 36a | 94a | 21a | 97a |
| 15.82418 | 86a | 79a | 13a | 108a | 20a | 69a | 70a | 24a | 36a | 94a | 21a | 97a |
| 15.82418 | 86a | 79a | 13a | 108a | 20a | 1a | 70a | 26a | 24a | 104a | 21a | 97a |
| 15.82418 | 79a | 13a | 76a | 20a | 1a | 70a | 26a | 24a | 94a | 104a | 21a | 97a |
| 15.89744 | 86a | 79a | 76a | 20a | 69a | 70a | 26a | 24a | 36a | 104a | 21a | 97a |
| 15.89744 | 86a | 79a | 13a | 108a | 20a | 69a | 1a | 26a | 24a | 94a | 21a | 97a |
| 15.89744 | 86a | 79a | 13a | 108a | 76a | 20a | 70a | 26a | 24a | 36a | 94a | 21a |
| 15.89744 | 86a | 79a | 13a | 108a | 20a | 69a | 1a | 70a | 26a | 24a | 94a | 21a |
| 15.89744 | 13a | 108a | 76a | 20a | 69a | 1a | 70a | 26a | 24a | 36a | 94a | 21a |
| 15.89744 | 86a | 79a | 108a | 76a | 20a | 1a | 70a | 26a | 24a | 36a | 21a | 97a |
| 15.89744 | 79a | 108a | 76a | 20a | 69a | 1a | 70a | 26a | 24a | 94a | 21a | 97a |
| 15.9707 | 79a | 108a | 76a | 20a | 69a | 70a | 26a | 24a | 94a | 104a | 21a | 97a |
| 15.9707 | 79a | 13a | 108a | 76a | 69a | 1a | 26a | 24a | 36a | 94a | 104a | 21a |
| 15.9707 | 79a | 76a | 20a | 69a | 70a | 26a | 24a | 36a | 94a | 104a | 21a | 97a |
| 15.9707 | 86a | 79a | 13a | 108a | 20a | 69a | 1a | 70a | 24a | 36a | 94a | 21a |
| 15.9707 | 79a | 13a | 108a | 20a | 69a | 1a | 70a | 24a | 36a | 94a | 21a | 97a |
| 15.9707 | 86a | 108a | 76a | 20a | 69a | 1a | 70a | 26a | 24a | 36a | 94a | 21a |
| 15.9707 | 86a | 79a | 108a | 76a | 20a | 69a | 1a | 70a | 24a | 104a | 21a | 97a |
| 15.9707 | 86a | 79a | 13a | 76a | 20a | 1a | 70a | 26a | 24a | 94a | 104a | 21a |
| 15.9707 | 86a | 79a | 13a | 108a | 76a | 20a | 70a | 24a | 36a | 94a | 104a | 21a |
| 15.9707 | 79a | 13a | 108a | 76a | 20a | 1a | 70a | 24a | 36a | 94a | 21a | 97a |
| 15.9707 | 79a | 13a | 76a | 20a | 69a | 1a | 70a | 24a | 94a | 104a | 21a | 97a |
| 16.04396 | 79a | 13a | 108a | 76a | 20a | 69a | 1a | 70a | 24a | 36a | 21a | 97a |
| 16.04396 | 79a | 13a | 108a | 76a | 20a | 69a | 1a | 24a | 36a | 104a | 21a | 97a |
| 16.04396 | 79a | 13a | 108a | 76a | 20a | 70a | 26a | 24a | 36a | 94a | 104a | 21a |
| 16.04396 | 86a | 79a | 13a | 108a | 76a | 20a | 69a | 1a | 70a | 24a | 104a | 21a |
| 16.04396 | 86a | 108a | 76a | 20a | 69a | 1a | 24a | 36a | 94a | 104a | 21a | 97a |
| 16.04396 | 79a | 108a | 76a | 20a | 69a | 1a | 70a | 26a | 24a | 36a | 104a | 21a |
| 16.04396 | 86a | 79a | 13a | 108a | 20a | 69a | 70a | 26a | 24a | 94a | 21a | 97a |
| 16.11722 | 86a | 108a | 20a | 69a | 1a | 70a | 24a | 36a | 94a | 104a | 21a | 97a |
| 16.11722 | 108 | 76a | 20a | 69a | 1a | 70a | 26a | 24a | 36a | 94a | 104a | 21a |
| 16.11722 | 86a | 108a | 76a | 20a | 1a | 70a | 24a | 36a | 94a | 104a | 21a | 97a |
| 16.11722 | 86a | 79a | 13a | 108a | 76a | 20a | 26a | 24a | 36a | 94a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 16.11722 | 86a | 79a | 13a | 108a | 76a | 20a | 1a | 26a | 24a | 36a | 104a | 21a |
| 16.19048 | 79a | 13a | 108a | 20a | 69a | 1a | 70a | 24a | 104a | 21a | 97a | |
| 16.19048 | 79a | 13a | 108a | 20a | 69a | 1a | 70a | 26a | 24a | 94a | 21a | 97a |
| 16.19048 | 86a | 108a | 76a | 20a | 69a | 70a | 26a | 24a | 36a | 94a | 21a | 97a |
| 16.19048 | 79a | 76a | 20a | 69a | 1a | 70a | 26a | 24a | 94a | 104a | 21a | 97a |
| 16.19048 | 86a | 79a | 13a | 108a | 76a | 20a | 1a | 70a | 24a | 104a | 21a | 97a |
| 16.19048 | 79a | 13a | 108a | 76a | 20a | 69a | 24a | 36a | 94a | 104a | 21a | 97a |
| 16.19048 | 79a | 13a | 76a | 20a | 69a | 1a | 70a | 26a | 24a | 104a | 21a | 97a |
| 16.26374 | 86a | 79a | 108a | 20a | 69a | 1a | 70a | 26a | 24a | 104a | 21a | 97a |
| 16.26374 | 86a | 13a | 108a | 76a | 20a | 69a | 70a | 24a | 36a | 94a | 104a | 21a |
| 16.26374 | 86a | 79a | 13a | 76a | 20a | 70a | 26a | 24a | 36a | 104a | 21a | 97a |
| 16.26374 | 86a | 13a | 108a | 76a | 20a | 69a | 70a | 26a | 24a | 36a | 104a | 21a |
| 16.26374 | 86a | 13a | 108a | 76a | 20a | 69a | 1a | 26a | 24a | 36a | 104a | 21a |
| 16.26374 | 79a | 13a | 76a | 20a | 69a | 1a | 70a | 26a | 24a | 94a | 21a | 97a |
| 16.26374 | 79a | 13a | 108a | 20a | 69a | 1a | 70a | 24a | 94a | 104a | 21a | 97a |
| 16.26374 | 86a | 79a | 13a | 108a | 76a | 20a | 1a | 70a | 24a | 94a | 104a | 21a |
| 16.26374 | 79a | 13a | 108a | 76a | 20a | 69a | 70a | 26a | 24a | 94a | 21a | 97a |
| 16.26374 | 86a | 79a | 108a | 76a | 20a | 70a | 26a | 24a | 94a | 104a | 21a | 97a |
| 16.26374 | 86a | 79a | 13a | 108a | 76a | 20a | 69a | 1a | 24a | 36a | 21a | 97a |
| 16.26374 | 86a | 79a | 13a | 108a | 20a | 69a | 1a | 70a | 26a | 24a | 104a | 21a |
| 16.26374 | 79a | 13a | 108a | 76a | 20a | 69a | 70a | 24a | 36a | 94a | 104a | 21a |
| 16.26374 | 79a | 13a | 76a | 20a | 69a | 70a | 26a | 24a | 36a | 94a | 21a | 97a |
| 16.26374 | 79a | 13a | 76a | 20a | 69a | 1a | 24a | 36a | 94a | 104a | 21a | 97a |
| 16.337 | 86a | 76a | 20a | 69a | 1a | 70a | 26a | 24a | 36a | 104a | 21a | 97a |
| 16.337 | 79a | 13a | 108a | 76a | 20a | 69a | 70a | 26a | 24a | 104a | 21a | 97a |
| 16.337 | 86a | 79a | 13a | 20a | 1a | 70a | 24a | 36a | 94a | 104a | 21a | 97a |
| 16.337 | 79a | 13a | 108a | 76a | 20a | 1a | 26a | 24a | 94a | 104a | 21a | 97a |
| 16.337 | 86a | 13a | 108a | 76a | 20a | 1a | 26a | 24a | 36a | 94a | 21a | 97a |
| 16.337 | 86a | 79a | 13a | 108a | 76a | 20a | 70a | 24a | 94a | 104a | 21a | 97a |
| 16.337 | 86a | 79a | 13a | 76a | 20a | 1a | 70a | 24a | 94a | 104a | 21a | 97a |
| 16.337 | 86a | 13a | 108a | 76a | 20a | 69a | 1a | 24a | 36a | 94a | 104a | 21a |
| 16.337 | 86a | 79a | 13a | 108a | 76a | 20a | 69a | 24a | 36a | 94a | 104a | 21a |
| 16.41026 | 86a | 79a | 13a | 108a | 20a | 69a | 70a | 26a | 24a | 36a | 21a | 97a |
| 16.41026 | 79a | 108a | 76a | 20a | 69a | 1a | 70a | 24a | 36a | 94a | 104a | 21a |
| 16.41026 | 79a | 13a | 108a | 76a | 20a | 1a | 70a | 24a | 94a | 104a | 21a | 97a |
| 16.41026 | 79a | 13a | 108a | 76a | 20a | 69a | 26a | 24a | 94a | 104a | 21a | 97a |
| 16.41026 | 86a | 79a | 13a | 108a | 20a | 1a | 70a | 26a | 24a | 94a | 104a | 21a |
| 16.41026 | 79a | 13a | 108a | 20a | 1a | 70a | 26a | 24a | 36a | 94a | 21a | 97a |
| 16.41026 | 86a | 79a | 13a | 108a | 20a | 1a | 70a | 24a | 104a | 21a | 97a | |
| 16.41026 | 76a | 20a | 69a | 1a | 70a | 26a | 24a | 36a | 94a | 104a | 21a | 97a |
| 16.41026 | 79a | 13a | 108a | 76a | 20a | 1a | 70a | 26a | 24a | 36a | 21a | 97a |
| 16.41026 | 86a | 79a | 13a | 76a | 20a | 69a | 1a | 70a | 24a | 94a | 104a | 21a |
| 16.41026 | 79a | 108a | 76a | 20a | 69a | 1a | 70a | 24a | 94a | 104a | 21a | 97a |
| 16.41026 | 79a | 108a | 76a | 20a | 69a | 70a | 26a | 24a | 36a | 104a | 21a | 97a |
| 16.41026 | 86a | 79a | 13a | 76a | 20a | 1a | 70a | 26a | 24a | 36a | 104a | 21a |
| 16.41026 | 86a | 79a | 13a | 108a | 76a | 20a | 69a | 26a | 24a | 94a | 104a | 21a |
| 16.41026 | 79a | 108a | 76a | 20a | 69a | 26a | 24a | 36a | 94a | 104a | 21a | 97a |
| 16.41026 | 86a | 79a | 13a | 76a | 20a | 1a | 24a | 36a | 94a | 104a | 21a | 97a |
| 16.41026 | 86a | 79a | 13a | 76a | 20a | 70a | 24a | 36a | 94a | 104a | 21a | 97a |
| 16.41026 | 13a | 108a | 76a | 20a | 69a | 70a | 26a | 24a | 36a | 94a | 21a | 97a |
| 16.41026 | 86a | 79a | 13a | 108a | 76a | 20a | 69a | 24a | 36a | 94a | 21a | 97a |
| 16.41026 | 86a | 108a | 76a | 20a | 69a | 1a | 26a | 24a | 36a | 94a | 21a | 97a |
| 16.48352 | 86a | 79a | 13a | 108a | 76a | 20a | 69a | 26a | 24a | 36a | 21a | 97a |
| 16.48352 | 86a | 79a | 76a | 20a | 69a | 1a | 70a | 24a | 94a | 104a | 21a | 97a |
| 16.48352 | 13a | 108a | 76a | 20a | 69a | 1a | 24a | 36a | 94a | 104a | 21a | 97a |
| 16.48352 | 86a | 13a | 108a | 76a | 20a | 70a | 26a | 24a | 36a | 94a | 21a | 97a |
| 16.48352 | 79a | 108a | 76a | 20a | 69a | 1a | 24a | 36a | 94a | 104a | 21a | 97a |
| 16.48352 | 86a | 79a | 108a | 76a | 20a | 70a | 26a | 24a | 36a | 94a | 21a | 97a |
| 16.48352 | 79a | 13a | 76a | 20a | 70a | 26a | 24a | 36a | 94a | 104a | 21a | 97a |
| 16.48352 | 86a | 79a | 13a | 108a | 76a | 20a | 1a | 26a | 24a | 104a | 21a | 97a |
| 16.48352 | 86a | 79a | 13a | 108a | 76a | 20a | 69a | 1a | 26a | 24a | 21a | 97a |
| 16.48352 | 86a | 79a | 13a | 108a | 76a | 20a | 69a | 26a | 24a | 94a | 21a | 97a |
| 16.48352 | 86a | 79a | 13a | 76a | 20a | 70a | 26a | 24a | 36a | 94a | 21a | 97a |
| 16.48352 | 86a | 79a | 13a | 108a | 20a | 69a | 1a | 70a | 24a | 104a | 21a | 97a |
| 16.48352 | 86a | 79a | 13a | 20a | 69a | 1a | 70a | 24a | 36a | 94a | 21a | 97a |
| 16.48352 | 86a | 79a | 108a | 20a | 69a | 1a | 70a | 24a | 94a | 104a | 21a | 97a |
| 16.48352 | 79a | 13a | 108a | 76a | 20a | 70a | 26a | 24a | 36a | 104a | 21a | 97a |
| 16.55678 | 86a | 79a | 13a | 108a | 76a | 20a | 1a | 24a | 36a | 104a | 21a | 97a |
| 16.55678 | 13a | 76a | 20a | 69a | 1a | 70a | 26a | 24a | 36a | 94a | 21a | 97a |
| 16.55678 | 86a | 79a | 108a | 76a | 20a | 69a | 1a | 70a | 24a | 94a | 104a | 21a |
| I6.55678 | 86a | 79a | 13a | 108a | 76a | 20a | 69a | 1a | 24a | 36a | 94a | 21a |
| 16.55678 | 86a | 79a | 13a | 108a | 20a | 69a | 1a | 70a | 24a | 94a | 104a | 21a |
| 16.55678 | 79a | 108a | 76a | 20a | 1a | 70a | 24a | 36a | 94a | 104a | 21a | 97a |
| 16.55678 | 86a | 79a | 13a | 76a | 20a | 69a | 70a | 24a | 36a | 94a | 104a | 21a |
| 16.55678 | 79a | 13a | 108a | 20a | 1a | 70a | 26a | 24a | 94a | 104a | 21a | 97a |
| 16.55678 | 86a | 79a | 76a | 20a | 69a | 1a | 70a | 24a | 36a | 104a | 21a | 97a |
| 16.55678 | 13a | 108a | 76a | 20a | 69a | 1a | 70a | 24a | 36a | 94a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 16.55678 | 79a | 13a | 76a | 20a | 69a | 70a | 24a | 36a | 94a | 104a | 21a | 97a |
| 16.55678 | 86a | 79a | 108a | 20a | 69a | 1a | 70a | 24a | 36a | 104a | 21a | 97a |
| 16.63004 | 86a | 13a | 108a | 76a | 20a | 69a | 1a | 26a | 24a | 94a | 104a | 21a |
| 16.63004 | 86a | 13a | 108a | 76a | 20a | 69a | 70a | 26a | 24a | 94a | 104a | 21a |
| 16.63004 | 86a | 79a | 13a | 108a | 76a | 20a | 69a | 26a | 24a | 36a | 104a | 21a |
| 16.63004 | 79a | 13a | 108a | 76a | 20a | 69a | 1a | 70a | 24a | 36a | 94a | 21a |
| 16.63004 | 86a | 79a | 13a | 76a | 20a | 69a | 70a | 24a | 36a | 94a | 21a | 97a |
| 16.63004 | 86a | 79a | 108a | 20a | 69a | 1a | 70a | 26a | 24a | 94a | 104a | 21a |
| 16.7033 | 86a | 79a | 108a | 76a | 20a | 69a | 70a | 24a | 94a | 104a | 21a | 97a |
| 16.7033 | 79a | 13a | 76a | 20a | 69a | 1a | 26a | 24a | 94a | 104a | 21a | 97a |
| 16.7033 | 79a | 13a | 108a | 76a | 20a | 69a | 1a | 26a | 24a | 94a | 21a | 97a |
| 16.7033 | 13a | 76a | 20a | 1a | 70a | 26a | 24a | 36a | 94a | 104a | 21a | 97a |
| 16.7033 | 86a | 79a | 13a | 108a | 20a | 69a | 70a | 26a | 24a | 104a | 21a | 97a |
| 16.7033 | 86a | 79a | 13a | 108a | 20a | 1a | 24a | 36a | 94a | 104a | 21a | 97a |
| 16.7033 | 86a | 76a | 20a | 69a | 1a | 70a | 26a | 24a | 36a | 94a | 21a | 97a |
| 16.7033 | 79a | 13a | 108a | 76a | 20a | 69a | 1a | 24a | 36a | 94a | 21a | 97a |
| 16.7033 | 86a | 79a | 108a | 20a | 69a | 1a | 70a | 24a | 36a | 94a | 104a | 21a |
| 16.7033 | 86a | 79a | 13a | 108a | 76a | 20a | 69a | 70a | 24a | 94a | 21a | 97a |
| 16.7033 | 86a | 79a | 13a | 108a | 76a | 20a | 1a | 24a | 36a | 94a | 104a | 21a |
| 16.7033 | 79a | 13a | 108a | 76a | 20a | 69a | 70a | 26a | 24a | 36a | 104a | 21a |
| 16.7033 | 86a | 79a | 108a | 76a | 20a | 1a | 70a | 24a | 36a | 104a | 21a | 97a |
| 16.7033 | 86a | 13a | 76a | 20a | 69a | 69a | 70a | 26a | 24a | 94a | 104a | 21a |
| 16.7033 | 86a | 79a | 13a | 76a | 20a | 69a | 70a | 26a | 24a | 36a | 104a | 21a |
| 16.77656 | 13a | 108a | 76a | 20a | 69a | 1a | 70a | 26a | 24a | 104a | 21a | 97a |
| 16.77656 | 86a | 108a | 76a | 20a | 69a | 70a | 26a | 24a | 94a | 104a | 21a | 97a |
| 16.77656 | 13a | 108a | 76a | 20a | 69a | 1a | 70a | 24a | 36a | 94a | 104a | 21a |
| 16.77656 | 86a | 79a | 108a | 76a | 20a | 70a | 24a | 36a | 94a | 104a | 21a | 97a |
| 16.77656 | 79a | 13a | 108a | 76a | 20a | 69a | 1a | 70a | 26a | 24a | 94a | 21a |
| 16.77656 | 79a | 13a | 108a | 76a | 20a | 69a | 70a | 26a | 24a | 36a | 21a | 97a |
| 16.77656 | 79a | 13a | 108a | 76a | 20a | 69a | 1a | 24a | 94a | 104a | 21a | 97a |
| 16.77656 | 86a | 13a | 108a | 76a | 20a | 1a | 70a | 26a | 24a | 104a | 21a | 97a |
| 16.77656 | 79a | 13a | 108a | 76a | 20a | 69a | 1a | 70a | 26a | 24a | 21a | 97a |
| 16.77656 | 86a | 79a | 13a | 108a | 76a | 20a | 69a | 1a | 24a | 36a | 104a | 21a |
| 16.77656 | 79a | 108a | 76a | 20a | 70a | 26a | 24a | 36a | 94a | 104a | 21a | 97a |
| 16.77656 | 79a | 13a | 108a | 76a | 20a | 1a | 26a | 24a | 36a | 94a | 21a | 97a |
| 16.84982 | 79a | 13a | 108a | 76a | 20a | 1a | 70a | 24a | 36a | 94a | 104a | 21a |
| 16.84982 | 86a | 79a | 108a | 76a | 20a | 70a | 26a | 24a | 36a | 104a | 21a | 97a |
| 16.84982 | 79a | 13a | 108a | 76a | 20a | 26a | 24a | 36a | 94a | 104a | 21a | 97a |
| 16.84982 | 86a | 79a | 108a | 76a | 20a | 69a | 1a | 70a | 26a | 24a | 36a | 21a |
| 16.84982 | 86a | 79a | 76a | 20a | 69a | 1a | 24a | 36a | 94a | 104a | 21a | 97a |
| 16.84982 | 86a | 79a | 108a | 76a | 20a | 69a | 1a | 70a | 24a | 36a | 104a | 21a |
| 16.84982 | 79a | 13a | 108a | 76a | 20a | 1a | 70a | 26a | 24a | 36a | 104a | 21a |
| 16.84982 | 13a | 108a | 76a | 20a | 1a | 70a | 26a | 24a | 36a | 94a | 104a | 21a |
| 16.84982 | 79a | 13a | 108a | 20a | 69a | 1a | 24a | 36a | 94a | 104a | 21a | 97a |
| 16.92308 | 86a | 79a | 13a | 76a | 20a | 70a | 26a | 24a | 94a | 104a | 21a | 97a |
| 16.92308 | 86a | 79a | 13a | 20a | 69a | 1a | 70a | 26a | 24a | 94a | 21a | 97a |
| 16.92308 | 86a | 79a | 13a | 108a | 76a | 20a | 26a | 24a | 36a | 104a | 21a | 97a |
| 16.92308 | 86a | 79a | 108a | 76a | 20a | 69a | 1a | 24a | 36a | 94a | 104a | 21a |
| 16.92308 | 13a | 108a | 76a | 20a | 1a | 26a | 24a | 36a | 94a | 104a | 21a | 97a |
| 16.92308 | 79a | 13a | 108a | 76a | 20a | 69a | 1a | 70a | 24a | 94a | 21a | 97a |
| 16.92308 | 79a | 13a | 108a | 20a | 69a | 1a | 70a | 26a | 24a | 104a | 21a | 97a |
| 16.92308 | 86a | 13a | 108a | 76a | 20a | 1a | 70a | 24a | 94a | 104a | 21a | 97a |
| 16.92308 | 86a | 79a | 108a | 76a | 20a | 69a | 1a | 24a | 36a | 104a | 21a | 97a |
| 16.92308 | 86a | 13a | 108a | 76a | 20a | 70a | 26a | 24a | 36a | 104a | 21a | 97a |
| 16.99634 | 86a | 79a | 13a | 108a | 76a | 20a | 69a | 70a | 24a | 36a | 21a | 97a |
| 16.99634 | 108 | 76a | 20a | 69a | 1a | 70a | 26a | 24a | 36a | 104a | 21a | 97a |
| 16.99634 | 13a | 108a | 76a | 20a | 1a | 70a | 26a | 24a | 36a | 104a | 21a | 97a |
| 16.99634 | 13a | 108a | 76a | 20a | 69a | 1a | 70a | 26a | 24a | 94a | 21a | 97a |
| 16.99634 | 86a | 108a | 76a | 20a | 69a | 1a | 26a | 24a | 36a | 104a | 21a | 97a |
| 16.99634 | 79a | 108a | 20a | 69a | 1a | 70a | 26a | 24a | 94a | 104a | 21a | 97a |
| 16.99634 | 86a | 108a | 20a | 69a | 1a | 70a | 26a | 24a | 36a | 94a | 21a | 97a |
| 16.99634 | 13a | 108a | 76a | 20a | 69a | 70a | 24a | 36a | 94a | 104a | 21a | 97a |
| 16.99634 | 86a | 79a | 108a | 76a | 20a | 69a | 26a | 24a | 36a | 104a | 21a | 97a |
| 16.99634 | 86a | 13a | 76a | 20a | 1a | 70a | 26a | 24a | 36a | 94a | 21a | 97a |
| 16.99634 | 79a | 13a | 76a | 20a | 1a | 70a | 26a | 24a | 36a | 104a | 21a | 97a |
| 16.99634 | 86a | 13a | 108a | 20a | 69a | 1a | 70a | 26a | 24a | 36a | 104a | 21a |
| 16.99634 | 86a | 79a | 13a | 76a | 20a | 69a | 1a | 24a | 36a | 94a | 21a | 97a |
| 16.99634 | 79a | 13a | 108a | 76a | 20a | 69a | 70a | 26a | 24a | 36a | 104a | 21a |
| 16.99634 | 79a | 13a | 108a | 20a | 69a | 1a | 26a | 24a | 94a | 104a | 21a | 97a |
| 16.99634 | 79a | 13a | 76a | 20a | 69a | 1a | 70a | 26a | 24a | 94a | 104a | 21a |
| 16.99634 | 86a | 79a | 76a | 20a | 69a | 70a | 26a | 24a | 94a | 104a | 21a | 97a |
| 16.99634 | 79a | 13a | 108a | 20a | 69a | 70a | 26a | 24a | 36a | 94a | 21a | 97a |
| 16.99634 | 86a | 79a | 13a | 108a | 20a | 1a | 70a | 24a | 36a | 94a | 104a | 21a |
| 16.99634 | 86a | 13a | 108a | 76a | 20a | 69a | 1a | 70a | 24a | 104a | 21a | 97a |
| 17.0696 | 108 | 76a | 20a | 69a | 1a | 26a | 24a | 36a | 94a | 104a | 21a | 97a |
| 17.0696 | 86a | 13a | 108a | 20a | 69a | 1a | 70a | 24a | 36a | 94a | 104a | 21a |
| 17.0696 | 86a | 108a | 76a | 20a | 1a | 70a | 26a | 24a | 36a | 94a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 17.0696 | 79a | 13a | 108a | 76a | 20a | 69a | 70a | 26a | 24a | 94a | 104a | 21a |
| 17.0696 | 86a | 79a | 13a | 108a | 76a | 20a | 69a | 1a | 70a | 24a | 94a | 21a |
| 17.0696 | 86a | 79a | 13a | 108a | 20a | 69a | 1a | 24a | 36a | 104a | 21a | 97a |
| 17.0696 | 86a | 79a | 13a | 108a | 20a | 1a | 70a | 24a | 36a | 104a | 21a | 97a |
| 17.0696 | 86a | 13a | 108a | 76a | 20a | 1a | 70a | 26a | 24a | 36a | 94a | 21a |
| 17.0696 | 13a | 108a | 76a | 20a | 69a | 1a | 26a | 24a | 94a | 104a | 21a | 97a |
| 17.0696 | 86a | 79a | 13a | 76a | 20a | 1a | 70a | 26a | 24a | 104a | 21a | 97a |
| 17.14286 | 86a | 79a | 13a | 108a | 76a | 20a | 69a | 1a | 70a | 24a | 21a | 97a |
| 17.14286 | 79a | 13a | 108a | 20a | 69a | 1a | 70a | 24a | 36a | 94a | 104a | 21a |
| 17.14286 | 86a | 79a | 13a | 20a | 69a | 1a | 70a | 24a | 94a | 104a | 21a | 97a |
| 17.14286 | 79a | 13a | 76a | 20a | 69a | 1a | 70a | 24a | 36a | 94a | 104a | 21a |
| 17.21612 | 13a | 108a | 76a | 20a | 69a | 1a | 70a | 26a | 24a | 94a | 104a | 21a |
| 17.21612 | 86a | 79a | 76a | 20a | 1a | 70a | 26a | 24a | 94a | 104a | 21a | 97a |
| 17.21612 | 86a | 79a | 13a | 108a | 76a | 20a | 26a | 24a | 94a | 104a | 21a | 97a |
| 17.21612 | 79a | 13a | 108a | 76a | 20a | 69a | 1a | 70a | 24a | 94a | 104a | 21a |
| 17.21612 | 79a | 13a | 76a | 20a | 69a | 70a | 26a | 24a | 36a | 104a | 21a | 97a |
| 17.21612 | 86a | 79a | 108a | 20a | 69a | 1a | 24a | 36a | 94a | 104a | 21a | 97a |
| 17.21612 | 86a | 76a | 20a | 69a | 1a | 70a | 26a | 24a | 94a | 104a | 21a | 97a |
| 17.21612 | 86a | 79a | 13a | 76a | 20a | 69a | 1a | 70a | 24a | 36a | 21a | 97a |
| 17.21612 | 86a | 79a | 76a | 20a | 69a | 1a | 70a | 26a | 24a | 104a | 21a | 97a |
| 17.21612 | 108a | 76a | 20a | 69a | 70a | 26a | 24a | 36a | 94a | 104a | 21a | 97a |
| 17.21612 | 86a | 13a | 76a | 20a | 69a | 1a | 70a | 24a | 94a | 104a | 21a | 97a |
| 17.28938 | 86a | 79a | 13a | 108a | 76a | 20a | 69a | 1a | 26a | 24a | 94a | 21a |
| 17.28938 | 86a | 79a | 13a | 108a | 76a | 20a | 24a | 36a | 94a | 104a | 21a | 97a |
| 17.28938 | 86a | 108a | 76a | 20a | 1a | 70a | 26a | 24a | 36a | 104a | 21a | 97a |
| 17.28938 | 13a | 108a | 20a | 69a | 1a | 70a | 26a | 24a | 36a | 94a | 21a | 97a |
| 17.28938 | 79a | 108a | 76a | 20a | 69a | 1a | 26a | 24a | 94a | 104a | 21a | 97a |
| 17.28938 | 79a | 13a | 76a | 20a | 1a | 26a | 24a | 36a | 94a | 104a | 21a | 97a |
| 17.28938 | 86a | 13a | 108a | 76a | 20a | 1a | 70a | 24a | 36a | 104a | 21a | 97a |
| 17.28938 | 86a | 13a | 76a | 20a | 1a | 70a | 24a | 36a | 94a | 104a | 21a | 97a |
| 17.28938 | 86a | 79a | 108a | 76a | 20a | 69a | 24a | 36a | 94a | 104a | 21a | 97a |
| 17.28938 | 86a | 79a | 13a | 76a | 20a | 69a | 70a | 26a | 24a | 36a | 21a | 97a |
| 17.28938 | 13a | 108a | 76a | 20a | 69a | 1a | 70a | 26a | 24a | 36a | 104a | 21a |
| 17.28938 | 86a | 79a | 13a | 76a | 20a | 1a | 70a | 24a | 36a | 104a | 21a | 97a |
| 17.28938 | 79a | 13a | 108a | 76a | 20a | 1a | 26a | 24a | 104a | 21a | 97a | |
| 17.28938 | 86a | 79a | 108a | 76a | 20a | 69a | 1a | 70a | 24a | 94a | 21a | 97a |
| 17.28938 | 86a | 13a | 108a | 20a | 69a | 1a | 70a | 24a | 94a | 104a | 21a | 97a |
| 17.28938 | 86a | 79a | 108a | 20a | 69a | 70a | 26a | 24a | 36a | 94a | 21a | 97a |
| 17.28938 | 86a | 13a | 108a | 20a | 1a | 70a | 24a | 36a | 94a | 104a | 21a | 97a |
| 17.28938 | 13a | 108a | 76a | 20a | 69a | 1a | 70a | 26a | 24a | 36a | 21a | 97a |
| 17.36264 | 79a | 13a | 76a | 20a | 69a | 1a | 70a | 24a | 36a | 104a | 21a | 97a |
| 17.36264 | 86a | 79a | 13a | 76a | 20a | 69a | 1a | 26a | 24a | 94a | 21a | 97a |
| 17.36264 | 86a | 79a | 13a | 76a | 20a | 69a | 1a | 70a | 24a | 24a | 21a | 97a |
| 17.36264 | 86a | 13a | 108a | 20a | 69a | 1a | 70a | 24a | 36a | 104a | 21a | 97a |
| 17.36264 | 79a | 13a | 108a | 76a | 20a | 69a | 1a | 70a | 24a | 36a | 104a | 21a |
| 17.36264 | 86a | 79a | 13a | 108a | 76a | 20a | 1a | 26a | 24a | 94a | 104a | 21a |
| 17.4359 | 79a | 108a | 76a | 20a | 1a | 70a | 26a | 24a | 36a | 94a | 21a | 97a |
| 17.4359 | 86a | 79a | 13a | 108a | 20a | 69a | 1a | 26a | 24a | 104a | 21a | 97a |
| 17.4359 | 86a | 13a | 108a | 76a | 20a | 69a | 70a | 26a | 24a | 104a | 21a | 97a |
| 17.4359 | 86a | 79a | 13a | 76a | 20a | 69a | 1a | 70a | 24a | 94a | 21a | 97a |
| 17.4359 | 79a | 13a | 108a | 76a | 20a | 1a | 70a | 26a | 24a | 36a | 94a | 21a |
| 17.4359 | 86a | 79a | 13a | 76a | 20a | 69a | 1a | 24a | 36a | 94a | 104a | 21a |
| 17.4359 | 86a | 13a | 76a | 20a | 69a | 1a | 70a | 26a | 24a | 36a | 104a | 21a |
| 17.4359 | 86a | 79a | 108a | 76a | 20a | 69a | 26a | 24a | 36a | 94a | 21a | 97a |
| 17.4359 | 86a | 79a | 13a | 108a | 20a | 69a | 70a | 24a | 94a | 104a | 21a | 97a |
| 17.4359 | 86a | 79a | 13a | 108a | 20a | 70a | 26a | 24a | 36a | 94a | 21a | 97a |
| 17.4359 | 86a | 13a | 76a | 20a | 69a | 1a | 70a | 24a | 94a | 104a | 21a | 97a |
| 17.4359 | 86a | 13a | 108a | 20a | 1a | 70a | 26a | 24a | 36a | 94a | 21a | 97a |
| 17.4359 | 108a | 76a | 20a | 1a | 70a | 26a | 24a | 36a | 94a | 104a | 21a | 97a |
| 17.50916 | 86a | 79a | 13a | 108a | 20a | 69a | 1a | 24a | 94a | 104a | 21a | 97a |
| 17.50916 | 86a | 79a | 13a | 76a | 20a | 69a | 70a | 26a | 24a | 36a | 94a | 21a |
| 17.50916 | 86a | 79a | 108a | 76a | 20a | 69a | 70a | 24a | 36a | 104a | 21a | 97a |
| 17.50916 | 86a | 13a | 108a | 76a | 20a | 69a | 70a | 26a | 24a | 36a | 94a | 21a |
| 17.50916 | 79a | 13a | 108a | 76a | 20a | 69a | 1a | 24a | 36a | 94a | 104a | 21a |
| 17.50916 | 86a | 13a | 108a | 20a | 69a | 1a | 70a | 26a | 24a | 94a | 104a | 21a |
| 17.58242 | 86a | 13a | 108a | 76a | 20a | 70a | 24a | 36a | 94a | 104a | 21a | 97a |
| 17.58242 | 79a | 13a | 76a | 20a | 69a | 26a | 24a | 36a | 94a | 104a | 21a | 97a |
| 17.58242 | 86a | 13a | 108a | 76a | 20a | 69a | 1a | 26a | 24a | 36a | 94a | 21a |
| 17.58242 | 86a | 108a | 20a | 69a | 1a | 70a | 26a | 24a | 36a | 104a | 21a | 97a |
| 17.58242 | 13a | 108a | 76a | 20a | 70a | 26a | 24a | 36a | 94a | 104a | 21a | 97a |
| 17.58242 | 86a | 79a | 108a | 76a | 20a | 69a | 1a | 26a | 24a | 94a | 21a | 97a |
| 17.58242 | 86a | 79a | 13a | 108a | 76a | 20a | 1a | 70a | 24a | 36a | 104a | 21a |
| 17.58242 | 86a | 79a | 76a | 20a | 69a | 1a | 70a | 26a | 24a | 94a | 104a | 21a |
| 17.58242 | 86a | 13a | 76a | 20a | 69a | 1a | 26a | 24a | 36a | 94a | 21a | 97a |
| 17.58242 | 86a | 79a | 108a | 76a | 20a | 1a | 70a | 24a | 94a | 104a | 21a | 97a |
| 17.58242 | 86a | 13a | 108a | 76a | 20a | 1a | 24a | 36a | 94a | 104a | 21a | 97a |
| 17.65568 | 79a | 13a | 108a | 76a | 20a | 69a | 26a | 24a | 36a | 94a | 104a | 21a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 17.65568 | 86a | 79a | 13a | 108a | 76a | 20a | 69a | 26a | 24a | 36a | 94a | 21a |
| 17.65568 | 79a | 108a | 76a | 20a | 1a | 70a | 26a | 24a | 94a | 104a | 21a | 97a |
| 17.65568 | 13a | 108a | 76a | 20a | 69a | 1a | 70a | 24a | 36a | 104a | 21a | 97a |
| 17.65568 | 86a | 79a | 108a | 20a | 69a | 70a | 24a | 36a | 94a | 104a | 21a | 97a |
| 17.65568 | 79a | 13a | 108a | 20a | 69a | 70a | 24a | 36a | 94a | 104a | 21a | 97a |
| 17.72894 | 86a | 79a | 13a | 108a | 20a | 69a | 1a | 24a | 36a | 94a | 104a | 21a |
| 17.72894 | 79a | 13a | 108a | 20a | 69a | 1a | 70a | 24a | 36a | 104a | 21a | 97a |
| 17.72894 | 86a | 79a | 108a | 20a | 69a | 1a | 70a | 26a | 24a | 36a | 21a | 97a |
| 17.72894 | 86a | 79a | 108a | 76a | 20a | 69a | 26a | 24a | 36a | 94a | 104a | 21a |
| 17.72894 | 86a | 108a | 76a | 20a | 69a | 70a | 26a | 24a | 36a | 94a | 104a | 21a |
| 17.72894 | 86a | 79a | 13a | 108a | 20a | 70a | 26a | 24a | 94a | 104a | 21a | 97a |
| 17.72894 | 86a | 79a | 108a | 76a | 20a | 69a | 1a | 26a | 24a | 104a | 21a | 97a |
| 17.72894 | 13a | 108a | 76a | 20a | 69a | 70a | 26a | 24a | 36a | 94a | 104a | 21a |
| 17.72894 | 79a | 76a | 20a | 1a | 70a | 26a | 24a | 36a | 94a | 104a | 21a | 97a |
| 17.72894 | 79a | 76a | 20a | 69a | 1a | 70a | 26a | 24a | 36a | 94a | 21a | 97a |
| 17.8022 | 86a | 13a | 108a | 20a | 69a | 1a | 70a | 26a | 24a | 104a | 21a | 97a |
| 17.8022 | 86a | 79a | 108a | 76a | 20a | 69a | 1a | 26a | 24a | 36a | 104a | 21a |
| 17.8022 | 86a | 13a | 108a | 20a | 69a | 70a | 24a | 36a | 94a | 104a | 21a | 97a |
| 17.8022 | 86a | 79a | 13a | 76a | 20a | 69a | 1a | 70a | 24a | 36a | 104a | 21a |
| 17.8022 | 86a | 13a | 108a | 76a | 20a | 69a | 1a | 70a | 24a | 36a | 104a | 21a |
| 17.8022 | 13a | 76a | 20a | 69a | 1a | 26a | 24a | 36a | 94a | 104a | 21a | 97a |
| 17.8022 | 13a | 76a | 20a | 69a | 1a | 70a | 24a | 36a | 94a | 104a | 21a | 97a |
| 17.8022 | 13a | 76a | 20a | 69a | 1a | 70a | 26a | 24a | 94a | 104a | 21a | 97a |
| 17.8022 | 13a | 76a | 20a | 69a | 1a | 70a | 26a | 24a | 36a | 104a | 21a | 97a |
| 17.8022 | 13a | 108a | 20a | 69a | 1a | 70a | 24a | 36a | 94a | 104a | 21a | 97a |
| 17.8022 | 86a | 13a | 108a | 76a | 20a | 69a | 1a | 24a | 36a | 104a | 21a | 97a |
| 17.8022 | 86a | 79a | 13a | 76a | 20a | 69a | 1a | 70a | 26a | 24a | 36a | 21a |
| 17.8022 | 86a | 79a | 108a | 20a | 69a | 70a | 26a | 24a | 94a | 104a | 21a | 97a |
| 17.8022 | 79a | 108a | 76a | 20a | 69a | 1a | 70a | 26a | 24a | 94a | 104a | 21a |
| 17.8022 | 79a | 13a | 76a | 20a | 69a | 70a | 26a | 24a | 36a | 94a | 104a | 21a |
| 17.8022 | 79a | 13a | 108a | 76a | 20a | 1a | 70a | 26a | 24a | 94a | 104a | 21a |
| 17.8022 | 86a | 13a | 108a | 20a | 1a | 70a | 26a | 24a | 36a | 104a | 21a | 97a |
| 17.8022 | 86a | 79a | 13a | 108a | 76a | 20a | 69a | 1a | 24a | 94a | 104a | 21a |
| 17.87546 | 86a | 79a | 76a | 20a | 1a | 70a | 26a | 24a | 36a | 104a | 21a | 97a |
| 17.87546 | 86a | 13a | 76a | 20a | 69a | 1a | 70a | 26a | 24a | 36a | 94a | 21a |
| 17.87546 | 86a | 79a | 108a | 76a | 20a | 69a | 26a | 24a | 94a | 104a | 21a | 97a |
| 17.87546 | 79a | 13a | 108a | 20a | 69a | 1a | 70a | 26a | 24a | 94a | 104a | 21a |
| 17.87546 | 86a | 79a | 13a | 108a | 76a | 20a | 69a | 1a | 26a | 24a | 36a | 21a |
| 17.87546 | 86a | 79a | 108a | 76a | 20a | 69a | 1a | 24a | 36a | 94a | 21a | 97a |
| 17.87546 | 79a | 13a | 20a | 69a | 1a | 70a | 24a | 36a | 94a | 104a | 21a | 97a |
| 17.87546 | 86a | 13a | 108a | 76a | 20a | 69a | 1a | 24a | 94a | 104a | 21a | 97a |
| 17.87546 | 86a | 79a | 13a | 108a | 76a | 20a | 70a | 24a | 36a | 104a | 21a | 97a |
| 17.87546 | 86a | 79a | 13a | 76a | 20a | 69a | 70a | 26a | 24a | 94a | 21a | 97a |
| 17.87546 | 86a | 79a | 13a | 76a | 20a | 69a | 1a | 26a | 24a | 94a | 104a | 21a |
| 17.87546 | 86a | 79a | 108a | 76a | 20a | 69a | 1a | 26a | 24a | 94a | 104a | 21a |
| 17.94872 | 86a | 13a | 76a | 20a | 69a | 70a | 26a | 24a | 36a | 94a | 21a | 97a |
| 17.94872 | 86a | 13a | 108a | 76a | 20a | 70a | 26a | 24a | 94a | 104a | 21a | 97a |
| 17.94872 | 86a | 79a | 76a | 20a | 69a | 70a | 26a | 24a | 36a | 94a | 104a | 21a |
| 17.94872 | 86a | 13a | 76a | 20a | 69a | 1a | 70a | 24a | 36a | 94a | 104a | 21a |
| 17.94872 | 86a | 79a | 13a | 108a | 20a | 69a | 70a | 26a | 24a | 94a | 104a | 21a |
| 17.94872 | 86a | 13a | 108a | 20a | 69a | 1a | 70a | 26a | 24a | 36a | 94a | 21a |
| 17.94872 | 86a | 13a | 76a | 20a | 69a | 1a | 24a | 36a | 94a | 104a | 21a | 97a |
| 17.94872 | 86a | 79a | 13a | 108a | 76a | 20a | 69a | 70a | 26a | 24a | 21a | 97a |
| 17.94872 | 13a | 108a | 76a | 20a | 69a | 70a | 26a | 24a | 94a | 104a | 21a | 97a |
| 18.02198 | 86a | 13a | 108a | 76a | 20a | 69a | 1a | 26a | 24a | 104a | 21a | 97a |
| 18.02198 | 86a | 13a | 108a | 76a | 20a | 69a | 26a | 24a | 36a | 94a | 21a | 97a |
| 18.02198 | 86a | 79a | 108a | 20a | 1a | 70a | 24a | 36a | 94a | 104a | 21a | 97a |
| 18.02198 | 86a | 79a | 13a | 108a | 20a | 69a | 1a | 26a | 24a | 94a | 104a | 21a |
| 18.02198 | 86a | 13a | 76a | 20a | 69a | 70a | 24a | 36a | 94a | 104a | 21a | 97a |
| 18.02198 | 13a | 108a | 76a | 20a | 69a | 1a | 26a | 24a | 36a | 104a | 21a | 97a |
| 18.02198 | 13a | 108a | 76a | 20a | 69a | 1a | 26a | 24a | 36a | 94a | 104a | 21a |
| 18.02198 | 86a | 79a | 13a | 108a | 20a | 69a | 1a | 26a | 24a | 36a | 21a | 97a |
| 18.02198 | 86a | 79a | 13a | 20a | 69a | 1a | 24a | 36a | 94a | 104a | 21a | 97a |
| 18.02198 | 86a | 76a | 20a | 69a | 70a | 26a | 24a | 36a | 94a | 104a | 21a | 97a |
| 18.09524 | 79a | 13a | 108a | 76a | 20a | 69a | 26a | 24a | 36a | 104a | 21a | 97a |
| 18.09524 | 86a | 79a | 13a | 108a | 20a | 1a | 70a | 26a | 24a | 36a | 104a | 21a |
| 18.09524 | 79a | 108a | 76a | 20a | 1a | 70a | 26a | 24a | 36a | 104a | 21a | 97a |
| 18.09524 | 86a | 79a | 13a | 20a | 69a | 1a | 70a | 24a | 36a | 104a | 21a | 97a |
| 18.09524 | 86a | 79a | 13a | 76a | 20a | 1a | 26a | 24a | 36a | 94a | 21a | 97a |
| 18.09524 | 79a | 13a | 76a | 20a | 69a | 70a | 26a | 24a | 94a | 104a | 21a | 97a |
| 18.09524 | 86a | 79a | 108a | 76a | 20a | 69a | 1a | 26a | 24a | 36a | 21a | 97a |
| 18.1685 | 86a | 79a | 13a | 20a | 69a | 26a | 24a | 36a | 94a | 104a | 21a | 97a |
| 18.1685 | 86a | 79a | 108a | 76a | 20a | 1a | 24a | 36a | 94a | 104a | 21a | 97a |
| 18.1685 | 79a | 108a | 20a | 69a | 1a | 70a | 26a | 24a | 36a | 94a | 21a | 97a |
| 18.1685 | 86a | 13a | 108a | 76a | 20a | 69a | 70a | 24a | 36a | 104a | 21a | 97a |
| 18.1685 | 86a | 79a | 108a | 20a | 69a | 70a | 26a | 24a | 36a | 104a | 21a | 97a |
| 18.1685 | 86a | 108a | 76a | 20a | 1a | 70a | 26a | 24a | 94a | 104a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 18.1685 | 86a | 79a | 13a | 108a | 76a | 20a | 26a | 24a | 36a | 94a | 104a | 21a |
| 18.1685 | 86a | 79a | 13a | 108a | 76a | 20a | 69a | 26a | 24a | 104a | 21a | 97a |
| 18.1685 | 86a | 79a | 76a | 20a | 69a | 70a | 26a | 24a | 36a | 94a | 21a | 97a |
| 18.1685 | 79a | 13a | 108a | 76a | 20a | 69a | 1a | 26a | 24a | 36a | 21a | 97a |
| 18.24176 | 108a | 20a | 69a | 1a | 70a | 26a | 24a | 36a | 94a | 104a | 21a | 97a |
| 18.24176 | 86a | 108a | 76a | 20a | 69a | 1a | 26a | 24a | 36a | 94a | 104a | 21a |
| 18.24176 | 86a | 13a | 20a | 69a | 1a | 70a | 24a | 36a | 94a | 104a | 21a | 97a |
| 18.24176 | 79a | 13a | 108a | 76a | 20a | 69a | 1a | 26a | 24a | 94a | 104a | 21a |
| 18.24176 | 13a | 108a | 20a | 69a | 1a | 70a | 26a | 24a | 94a | 104a | 21a | 97a |
| 18.24176 | 86a | 79a | 13a | 108a | 20a | 69a | 26a | 24a | 36a | 94a | 21a | 97a |
| 18.24176 | 86a | 13a | 108a | 76a | 20a | 69a | 70a | 24a | 94a | 104a | 21a | 97a |
| 18.31502 | 79a | 108a | 76a | 20a | 69a | 1a | 70a | 26a | 24a | 36a | 21a | 97a |
| 18.31502 | 86a | 13a | 108a | 76a | 20a | 1a | 26a | 24a | 36a | 104a | 21a | 97a |
| 18.31502 | 86a | 13a | 108a | 20a | 69a | 1a | 26a | 24a | 36a | 94a | 21a | 97a |
| 18.31502 | 79a | 13a | 76a | 20a | 1a | 70a | 26a | 24a | 36a | 94a | 104a | 21a |
| 18.38828 | 86a | 79a | 13a | 20a | 1a | 70a | 26a | 24a | 94a | 104a | 21a | 97a |
| 18.38828 | 86a | 13a | 108a | 76a | 20a | 70a | 26a | 24a | 36a | 94a | 104a | 21a |
| 18.38828 | 13a | 76a | 20a | 69a | 70a | 26a | 24a | 36a | 94a | 104a | 21a | 97a |
| 18.38828 | 79a | 108a | 76a | 20a | 69a | 1a | 26a | 24a | 36a | 94a | 21a | 97a |
| 18.46154 | 86a | 79a | 13a | 108a | 20a | 69a | 24a | 36a | 94a | 104a | 21a | 97a |
| 18.46154 | 79a | 13a | 20a | 69a | 1a | 70a | 26a | 24a | 94a | 104a | 21a | 97a |
| 18.46154 | 86a | 13a | 76a | 20a | 1a | 70a | 26a | 24a | 36a | 104a | 21a | 97a |
| 18.46154 | 79a | 108a | 20a | 69a | 70a | 26a | 24a | 36a | 94a | 104a | 21a | 97a |
| 18.46154 | 86a | 79a | 13a | 76a | 20a | 1a | 26a | 24a | 94a | 104a | 21a | 97a |
| 18.46154 | 79a | 108a | 76a | 20a | 69a | 1a | 70a | 26a | 24a | 36a | 104a | 21a |
| 18.5348 | 86a | 79a | 13a | 108a | 20a | 69a | 26a | 24a | 94a | 104a | 21a | 97a |
| 18.5348 | 86a | 76a | 20a | 69a | 1a | 70a | 26a | 24a | 36a | 94a | 104a | 21a |
| 18.5348 | 86a | 79a | 76a | 20a | 1a | 70a | 26a | 24a | 36a | 94a | 21a | 97a |
| 18.5348 | 86a | 79a | 76a | 20a | 70a | 26a | 24a | 36a | 94a | 104a | 21a | 97a |
| 18.5348 | 86a | 79a | 108a | 76a | 20a | 1a | 70a | 26a | 24a | 94a | 104a | 21a |
| 18.5348 | 86a | 79a | 13a | 108a | 20a | 1a | 70a | 26a | 24a | 36a | 94a | 21a |
| 18.5348 | 86a | 79a | 13a | 20a | 69a | 70a | 26a | 24a | 94a | 104a | 21a | 97a |
| 18.60806 | 86a | 108a | 76a | 20a | 69a | 1a | 26a | 24a | 94a | 104a | 21a | 97a |
| 18.60806 | 79a | 13a | 108a | 20a | 69a | 70a | 26a | 24a | 94a | 104a | 21a | 97a |
| 18.60806 | 86a | 79a | 13a | 108a | 20a | 70a | 26a | 24a | 36a | 104a | 21a | 97a |
| 18.60806 | 79a | 76a | 20a | 69a | 1a | 70a | 26a | 24a | 36a | 104a | 21a | 97a |
| 18.60806 | 86a | 13a | 108a | 20a | 69a | 70a | 26a | 24a | 36a | 94a | 21a | 97a |
| 18.60806 | 86a | 13a | 76a | 20a | 1a | 70a | 26a | 24a | 94a | 104a | 21a | 97a |
| 18.60806 | 86a | 79a | 13a | 108a | 20a | 1a | 26a | 24a | 94a | 104a | 21a | 97a |
| 18.60806 | 86a | 79a | 108a | 76a | 20a | 1a | 70a | 26a | 24a | 36a | 104a | 21a |
| 18.60806 | 86a | 79a | 13a | 20a | 69a | 1a | 70a | 24a | 36a | 94a | 104a | 21a |
| 18.60806 | 86a | 79a | 13a | 76a | 20a | 70a | 26a | 24a | 36a | 94a | 104a | 21a |
| 18.68132 | 86a | 79a | 13a | 20a | 69a | 1a | 70a | 26a | 24a | 104a | 21a | 97a |
| 18.68132 | 13a | 76a | 20a | 69a | 1a | 70a | 26a | 24a | 36a | 94a | 104a | 21a |
| 18.68132 | 13a | 108a | 20a | 1a | 70a | 26a | 24a | 36a | 94a | 104a | 21a | 97a |
| 18.68132 | 86a | 13a | 76a | 20a | 69a | 70a | 26a | 24a | 36a | 104a | 21a | 97a |
| 18.68132 | 86a | 79a | 13a | 76a | 20a | 69a | 70a | 26a | 24a | 94a | 21a | 97a |
| 18.68132 | 86a | 79a | 13a | 108a | 76a | 20a | 69a | 70a | 24a | 104a | 21a | 97a |
| 18.68132 | 86a | 79a | 13a | 108a | 20a | 1a | 26a | 24a | 36a | 94a | 21a | 97a |
| 18.68132 | 86a | 79a | 13a | 108a | 20a | 69a | 70a | 26a | 24a | 36a | 94a | 21a |
| 18.68132 | 86a | 79a | 20a | 69a | 1a | 70a | 26a | 24a | 94a | 104a | 21a | 97a |
| 18.68132 | 86a | 79a | 13a | 108a | 20a | 69a | 1a | 70a | 26a | 24a | 36a | 97a |
| 18.75458 | 79a | 13a | 108a | 20a | 1a | 70a | 26a | 24a | 36a | 94a | 104a | 21a |
| 18.75458 | 86a | 108a | 20a | 69a | 1a | 70a | 26a | 24a | 36a | 94a | 104a | 21a |
| 18.75458 | 79a | 108a | 76a | 20a | 69a | 1a | 70a | 26a | 24a | 36a | 94a | 21a |
| 18.75458 | 86a | 79a | 13a | 76a | 20a | 1a | 70a | 26a | 24a | 36a | 94a | 21a |
| 18.75458 | 79a | 13a | 108a | 20a | 1a | 70a | 26a | 24a | 36a | 104a | 21a | 97a |
| 18.75458 | 86a | 13a | 108a | 20a | 69a | 1a | 24a | 36a | 94a | 104a | 21a | 97a |
| 18.75458 | 86a | 13a | 76a | 20a | 69a | 70a | 26a | 24a | 94a | 104a | 21a | 97a |
| 18.75458 | 79a | 76a | 20a | 69a | 1a | 26a | 24a | 36a | 94a | 104a | 21a | 97a |
| 18.75458 | 86a | 79a | 13a | 108a | 76a | 20a | 69a | 1a | 24a | 104a | 21a | 97a |
| 18.82784 | 86a | 79a | 13a | 108a | 76a | 20a | 1a | 24a | 94a | 104a | 21a | 97a |
| 18.82784 | 86a | 79a | 13a | 20a | 1a | 70a | 26a | 24a | 36a | 104a | 21a | 97a |
| 18.9011 | 86a | 79a | 13a | 108a | 20a | 70a | 24a | 36a | 94a | 104a | 21a | 97a |
| 18.9011 | 86a | 13a | 108a | 20a | 69a | 70a | 24a | 36a | 94a | 104a | 21a | 97a |
| 18.9011 | 86a | 13a | 108a | 20a | 69a | 70a | 26a | 24a | 36a | 104a | 21a | 97a |
| 18.9011 | 86a | 108a | 20a | 69a | 1a | 70a | 26a | 24a | 94a | 104a | 21a | 97a |
| 18.9011 | 86a | 13a | 108a | 76a | 20a | 1a | 26a | 24a | 36a | 94a | 104a | 21a |
| 18.9011 | 79a | 13a | 76a | 20a | 69a | 1a | 26a | 24a | 36a | 94a | 21a | 97a |
| 18.97436 | 86a | 79a | 13a | 76a | 20a | 69a | 26a | 24a | 36a | 94a | 21a | 97a |
| 18.97436 | 86a | 79a | 13a | 108a | 20a | 69a | 26a | 24a | 36a | 104a | 21a | 97a |
| 18.97436 | 86a | 79a | 13a | 108a | 20a | 1a | 26a | 24a | 36a | 104a | 21a | 97a |
| 18.97436 | 86a | 79a | 76a | 20a | 69a | 1a | 70a | 26a | 24a | 36a | 21a | 97a |
| 18.97436 | 86a | 79a | 13a | 76a | 20a | 69a | 1a | 70a | 24a | 104a | 21a | 97a |
| 18.97436 | 79a | 13a | 76a | 20a | 69a | 1a | 70a | 26a | 24a | 36a | 94a | 21a |
| 18.97436 | 86a | 79a | 13a | 20a | 69a | 1a | 70a | 26a | 24a | 94a | 104a | 21a |
| 18.97436 | 86a | 79a | 13a | 76a | 20a | 69a | 1a | 24a | 94a | 104a | 21a | 97a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 19.04762 | 86a | 79a | 13a | 20a | 69a | 70a | 26a | 24a | 36a | 94a | 21a | 97a |
| 19.04762 | 86a | 79a | 13a | 76a | 20a | 1a | 26a | 24a | 36a | 104a | 21a | 97a |
| 19.04762 | 86a | 79a | 108a | 76a | 20a | 1a | 70a | 24a | 36a | 94a | 104a | 21a |
| 19.04762 | 86a | 13a | 108a | 20a | 1a | 70a | 26a | 24a | 94a | 104a | 21a | 97a |
| 19.04762 | 86a | 79a | 108a | 76a | 20a | 1a | 26a | 24a | 36a | 104a | 21a | 97a |
| 19.04762 | 86a | 79a | 76a | 20a | 69a | 1a | 26a | 24a | 94a | 104a | 21a | 97a |
| 19.04762 | 86a | 79a | 13a | 108a | 76a | 20a | 69a | 1a | 24a | 94a | 21a | 97a |
| 19.04762 | 79a | 13a | 20a | 1a | 70a | 26a | 24a | 36a | 94a | 104a | 21a | 97a |
| 19.12088 | 86a | 79a | 108a | 20a | 1a | 70a | 26a | 24a | 36a | 94a | 21a | 97a |
| 19.12088 | 13a | 108a | 76a | 20a | 69a | 70a | 26a | 24a | 36a | 104a | 21a | 97a |
| 19.12088 | 86a | 13a | 76a | 20a | 69a | 1a | 70a | 26a | 24a | 104a | 21a | 97a |
| 19.12088 | 79a | 13a | 108a | 20a | 69a | 1a | 26a | 24a | 36a | 94a | 21a | 97a |
| 19.12088 | 13a | 108a | 20a | 69a | 1a | 70a | 26a | 24a | 36a | 104a | 21a | 97a |
| 19.12088 | 79a | 13a | 108a | 20a | 1a | 26a | 24a | 36a | 94a | 104a | 21a | 97a |
| 19.12088 | 79a | 13a | 108a | 76a | 20a | 69a | 1a | 70a | 26a | 24a | 36a | 21a |
| 19.12088 | 86a | 13a | 20a | 69a | 1a | 70a | 26a | 24a | 36a | 94a | 21a | 97a |
| 19.12088 | 13a | 108a | 20a | 69a | 1a | 70a | 26a | 24a | 36a | 94a | 104a | 21a |
| 19.19414 | 79a | 108a | 76a | 20a | 69a | 1a | 26a | 24a | 36a | 104a | 21a | 97a |
| 19.19414 | 86a | 79a | 108a | 20a | 1a | 70a | 26a | 24a | 94a | 104a | 21a | 97a |
| 19.19414 | 86a | 108a | 76a | 20a | 1a | 70a | 26a | 24a | 36a | 94a | 104a | 21a |
| 19.19414 | 86a | 13a | 108a | 76a | 20a | 1a | 26a | 24a | 94a | 104a | 21a | 97a |
| 19.2674 | 86a | 79a | 13a | 108a | 76a | 20a | 69a | 70a | 24a | 36a | 104a | 21a |
| 19.2674 | 86a | 13a | 76a | 20a | 69a | 1a | 26a | 24a | 36a | 104a | 21a | 97a |
| 19.2674 | 79a | 13a | 108a | 76a | 20a | 1a | 26a | 24a | 36a | 94a | 104a | 21a |
| 19.2674 | 86a | 79a | 76a | 20a | 69a | 26a | 24a | 36a | 94a | 104a | 21a | 97a |
| 19.34066 | 86a | 79a | 13a | 108a | 76a | 20a | 69a | 24a | 94a | 104a | 21a | 97a |
| 19.34066 | 86a | 79a | 13a | 20a | 69a | 1a | 70a | 26a | 24a | 36a | 94a | 21a |
| 19.34066 | 79a | 13a | 108a | 20a | 70a | 26a | 24a | 36a | 94a | 104a | 21a | 97a |
| 19.41392 | 79a | 76a | 20a | 69a | 1a | 70a | 26a | 24a | 36a | 94a | 104a | 21a |
| 19.41392 | 86a | 79a | 108a | 20a | 69a | 1a | 26a | 24a | 94a | 104a | 21a | 97a |
| 19.41392 | 86a | 13a | 108a | 76a | 20a | 69a | 26a | 24a | 94a | 104a | 21a | 97a |
| 19.41392 | 86a | 79a | 13a | 20a | 1a | 70a | 26a | 24a | 36a | 94a | 21a | 97a |
| 19.48718 | 79a | 13a | 108a | 20a | 69a | 70a | 26a | 24a | 36a | 94a | 104a | 21a |
| 19.48718 | 86a | 79a | 20a | 69a | 70a | 26a | 24a | 36a | 104a | 21a | 97a | |
| 19.48718 | 79a | 108a | 20a | 1a | 70a | 26a | 24a | 36a | 94a | 104a | 21a | 97a |
| 19.48718 | 79a | 13a | 108a | 20a | 69a | 1a | 70a | 26a | 24a | 36a | 94a | 21a |
| 19.48718 | 86a | 79a | 13a | 108a | 20a | 69a | 70a | 24a | 36a | 104a | 21a | 97a |
| 19.48718 | 86a | 13a | 76a | 20a | 69a | 1a | 26a | 24a | 94a | 104a | 21a | 97a |
| 19.48718 | 86a | 13a | 108a | 20a | 1a | 70a | 26a | 24a | 36a | 94a | 104a | 21a |
| 19.56044 | 86a | 13a | 108a | 20a | 69a | 70a | 26a | 24a | 94a | 104a | 21a | 97a |
| 19.56044 | 86a | 13a | 20a | 69a | 1a | 70a | 26a | 24a | 36a | 104a | 21a | 97a |
| 19.56044 | 86a | 79a | 13a | 76a | 20a | 69a | 24a | 36a | 94a | 104a | 21a | 97a |
| 19.6337 | 86a | 79a | 13a | 76a | 20a | 69a | 70a | 26a | 24a | 104a | 21a | 97a |
| 19.6337 | 79a | 13a | 108a | 20a | 69a | 70a | 26a | 24a | 36a | 104a | 21a | 97a |
| 19.6337 | 86a | 79a | 108a | 20a | 69a | 1a | 70a | 26a | 24a | 36a | 104a | 21a |
| 19.6337 | 86a | 13a | 108a | 76a | 20a | 69a | 26a | 24a | 36a | 104a | 21a | 97a |
| 19.6337 | 86a | 79a | 76a | 20a | 69a | 1a | 70a | 26a | 24a | 36a | 94a | 21a |
| 19.6337 | 86a | 79a | 13a | 76a | 20a | 69a | 1a | 26a | 24a | 36a | 21a | 97a |
| 19.6337 | 79a | 13a | 20a | 69a | 70a | 26a | 24a | 36a | 94a | 104a | 21a | 97a |
| 19.70696 | 79a | 13a | 76a | 20a | 69a | 1a | 26a | 24a | 36a | 104a | 21a | 97a |
| 19.70696 | 86a | 79a | 13a | 76a | 20a | 69a | 26a | 24a | 94a | 104a | 21a | 97a |
| 19.78022 | 13a | 108a | 76a | 20a | 69a | 26a | 24a | 36a | 94a | 104a | 21a | 97a |
| 19.78022 | 86a | 79a | 108a | 76a | 20a | 1a | 26a | 24a | 36a | 94a | 21a | 97a |
| 19.78022 | 86a | 13a | 20a | 69a | 1a | 70a | 26a | 24a | 94a | 104a | 21a | 97a |
| 19.78022 | 86a | 79a | 13a | 108a | 20a | 69a | 70a | 24a | 36a | 94a | 104a | 21a |
| 19.78022 | 79a | 13a | 76a | 20a | 69a | 1a | 70a | 26a | 24a | 36a | 21a | 97a |
| 19.85348 | 86a | 13a | 108a | 20a | 69a | 1a | 26a | 24a | 36a | 104a | 21a | 97a |
| 19.85348 | 79a | 13a | 108a | 76a | 20a | 69a | 1a | 26a | 24a | 36a | 104a | 21a |
| 19.85348 | 86a | 79a | 13a | 108a | 76a | 20a | 69a | 24a | 36a | 94a | 21a | 97a |
| 19.85348 | 86a | 79a | 13a | 20a | 69a | 1a | 26a | 24a | 94a | 104a | 21a | 97a |
| 19.85348 | 86a | 13a | 108a | 76a | 20a | 69a | 24a | 36a | 94a | 104a | 21a | 97a |
| 19.92674 | 79a | 108a | 20a | 69a | 1a | 70a | 26a | 24a | 36a | 94a | 104a | 21a |
| 19.92674 | 79a | 13a | 108a | 20a | 69a | 1a | 70a | 26a | 24a | 36a | 21a | 97a |
| 19.92674 | 86a | 79a | 108a | 20a | 69a | 1a | 70a | 26a | 24a | 36a | 94a | 21a |
| 20 | 86a | 79a | 13a | 76a | 20a | 69a | 1a | 24a | 36a | 104a | 21a | 97a |
| 20 | 86a | 79a | 108a | 76a | 20a | 70a | 26a | 24a | 36a | 94a | 104a | 21a |
| 20 | 79a | 13a | 108a | 20a | 69a | 26a | 24a | 36a | 94a | 104a | 21a | 97a |
| 20 | 79a | 108a | 76a | 20a | 1a | 26a | 24a | 36a | 94a | 104a | 21a | 97a |
| 20 | 13a | 20a | 69a | 1a | 70a | 26a | 24a | 36a | 94a | 104a | 21a | 97a |
| 20 | 86a | 79a | 13a | 108a | 76a | 20a | 1a | 26a | 24a | 36a | 94a | 21a |
| 20 | 86a | 79a | 13a | 76a | 20a | 26a | 24a | 36a | 94a | 104a | 21a | 97a |
| 20 | 86a | 79a | 13a | 20a | 70a | 26a | 24a | 36a | 94a | 104a | 21a | 97a |
| 20 | 86a | 13a | 76a | 20a | 69a | 1a | 70a | 26a | 36a | 104a | 21a | 97a |
| 20 | 86a | 76a | 20a | 69a | 1a | 26a | 24a | 36a | 94a | 104a | 21a | 97a |
| 20.07326 | 86a | 79a | 13a | 108a | 20a | 69a | 70a | 26a | 24a | 36a | 104a | 21a |
| 20.07326 | 86a | 79a | 13a | 76a | 20a | 69a | 1a | 26a | 24a | 104a | 21a | 97a |
| 20.07326 | 86a | 13a | 76a | 20a | 1a | 70a | 26a | 24a | 36a | 94a | 104a | 21a |

TABLE-continued

| Field1 | 1 | 2 | 3 | 4 | 5 | 6 | 7 | 8 | 9 | 10 | 11 | 12 |
|---|---|---|---|---|---|---|---|---|---|---|---|---|
| 20.07326 | 86a | 79a | 13a | 108a | 20a | 69a | 1a | 70a | 24a | 36a | 104a | 21a |
| 20.14652 | 79a | 13a | 76a | 20a | 69a | 1a | 70a | 26a | 24a | 36a | 104a | 21a |
| 20.14652 | 86a | 79a | 13a | 76a | 20a | 69a | 26a | 24a | 36a | 104a | 21a | 97a |
| 20.14652 | 86a | 79a | 108a | 76a | 20a | 26a | 24a | 36a | 94a | 104a | 21a | 97a |
| 20.14652 | 86a | 76a | 20a | 1a | 70a | 26a | 24a | 36a | 94a | 104a | 21a | 97a |
| 20.14652 | 86a | 13a | 108a | 20a | 69a | 1a | 26a | 24a | 94a | 104a | 21a | 97a |
| 20.21978 | 86a | 79a | 13a | 76a | 20a | 69a | 70a | 24a | 36a | 104a | 21a | 97a |
| 20.21978 | 86a | 79a | 20a | 69a | 1a | 70a | 26a | 24a | 36a | 104a | 21a | 97a |
| 20.29304 | 86a | 79a | 108a | 20a | 69a | 1a | 26a | 24a | 36a | 94a | 21a | 97a |
| 20.29304 | 86a | 13a | 76a | 20a | 70a | 26a | 24a | 36a | 94a | 104a | 21a | 97a |
| 20.3663 | 13a | 108a | 20a | 69a | 1a | 26a | 24a | 36a | 94a | 104a | 21a | 97a |
| 20.3663 | 86a | 79a | 108a | 76a | 20a | 1a | 70a | 26a | 24a | 36a | 94a | 21a |
| 20.3663 | 79a | 13a | 108a | 76a | 20a | 69a | 1a | 26a | 24a | 36a | 94a | 21a |
| 20.43956 | 86a | 108a | 76a | 20a | 70a | 26a | 24a | 36a | 94a | 104a | 21a | 97a |
| 20.43956 | 86a | 79a | 13a | 76a | 20a | 69a | 1a | 26a | 24a | 36a | 104a | 21a |
| 20.51282 | 79a | 13a | 20a | 69a | 1a | 70a | 26a | 24a | 36a | 94a | 21a | 97a |
| 20.51282 | 86a | 79a | 108a | 76a | 20a | 1a | 26a | 24a | 94a | 104a | 21a | 97a |
| 20.58608 | 79a | 108a | 76a | 20a | 1a | 70a | 26a | 24a | 36a | 94a | 104a | 21a |
| 20.58608 | 79a | 108a | 20a | 69a | 1a | 26a | 24a | 36a | 94a | 104a | 21a | 97a |
| 20.58608 | 86a | 79a | 108a | 20a | 69a | 70a | 26a | 24a | 36a | 94a | 104a | 21a |
| 20.58608 | 86a | 13a | 76a | 20a | 69a | 70a | 26a | 24a | 36a | 94a | 104a | 21a |
| 20.65934 | 79a | 108a | 20a | 69a | 1a | 70a | 26a | 24a | 36a | 104a | 21a | 97a |
| 20.65934 | 79a | 20a | 69a | 1a | 70a | 26a | 24a | 36a | 94a | 104a | 21a | 97a |
| 20.65934 | 79a | 108a | 76a | 20a | 69a | 1a | 26a | 24a | 36a | 94a | 104a | 21a |
| 20.7326 | 86a | 79a | 13a | 108a | 20a | 69a | 1a | 26a | 24a | 36a | 104a | 21a |
| 20.7326 | 86a | 79a | 108a | 20a | 1a | 70a | 26a | 24a | 36a | 104a | 21a | 97a |
| 20.7326 | 86a | 79a | 76a | 20a | 69a | 1a | 26a | 24a | 36a | 104a | 21a | 97a |
| 20.7326 | 86a | 79a | 108a | 76a | 20a | 69a | 1a | 24a | 94a | 104a | 21a | 97a |
| 20.7326 | 79a | 13a | 108a | 20a | 69a | 1a | 70a | 26a | 24a | 36a | 104a | 21a |
| 20.95238 | 86a | 79a | 108a | 20a | 69a | 1a | 26a | 24a | 36a | 104a | 21a | 97a |
| 21.02564 | 86a | 13a | 108a | 76a | 20a | 69a | 26a | 24a | 36a | 94a | 104a | 21a |
| 21.02564 | 86a | 79a | 108a | 20a | 69a | 26a | 24a | 36a | 94a | 104a | 21a | 97a |
| 21.0989 | 86a | 20a | 69a | 1a | 70a | 26a | 24a | 36a | 94a | 104a | 21a | 97a |
| 21.24542 | 86a | 108a | 76a | 20a | 69a | 26a | 24a | 36a | 94a | 104a | 21a | 97a |
| 21.24542 | 86a | 79a | 108a | 76a | 20a | 69a | 1a | 26a | 24a | 36a | 94a | 21a |
| 21.31868 | 86a | 79a | 13a | 76a | 20a | 1a | 26a | 24a | 36a | 94a | 104a | 21a |
| 21.31868 | 86a | 79a | 13a | 108a | 20a | 1a | 26a | 24a | 36a | 94a | 104a | 21a |
| 21.39194 | 86a | 79a | 76a | 20a | 1a | 70a | 26a | 24a | 36a | 94a | 104a | 21a |
| 21.4652 | 13a | 108a | 20a | 69a | 70a | 26a | 24a | 36a | 94a | 104a | 21a | 97a |
| 21.4652 | 86a | 79a | 20a | 69a | 1a | 70a | 26a | 24a | 94a | 21a | 97a | |
| 21.4652 | 86a | 79a | 13a | 76a | 20a | 69a | 26a | 24a | 36a | 94a | 104a | 21a |
| 21.53846 | 86a | 108a | 20a | 69a | 70a | 26a | 24a | 36a | 94a | 104a | 21a | 97a |
| 21.61172 | 86a | 79a | 13a | 108a | 20a | 26a | 24a | 36a | 94a | 104a | 21a | 97a |
| 21.61172 | 86a | 79a | 76a | 20a | 69a | 1a | 26a | 24a | 36a | 94a | 21a | 97a |
| 21.61172 | 86a | 79a | 13a | 20a | 69a | 1a | 70a | 26a | 24a | 36a | 104a | 21a |
| 21.61172 | 86a | 79a | 13a | 108a | 20a | 70a | 26a | 24a | 36a | 94a | 104a | 21a |
| 21.68498 | 86a | 13a | 20a | 1a | 70a | 26a | 24a | 36a | 94a | 104a | 21a | 97a |
| 21.68498 | 86a | 13a | 108a | 20a | 69a | 70a | 26a | 24a | 36a | 94a | 104a | 21a |
| 21.68498 | 79a | 13a | 20a | 69a | 1a | 70a | 26a | 24a | 36a | 104a | 21a | 97a |
| 21.75824 | 86a | 79a | 76a | 20a | 1a | 26a | 24a | 36a | 94a | 104a | 21a | 97a |
| 21.75824 | 86a | 13a | 76a | 20a | 69a | 1a | 26a | 24a | 36a | 94a | 104a | 21a |
| 21.75824 | 86a | 13a | 20a | 69a | 70a | 26a | 24a | 36a | 94a | 104a | 21a | 97a |
| 21.75824 | 86a | 79a | 13a | 108a | 20a | 69a | 26a | 24a | 36a | 94a | 104a | 21a |
| 21.8315 | 79a | 13a | 108a | 20a | 69a | 1a | 26a | 24a | 36a | 104a | 21a | 97a |
| 21.90476 | 86a | 13a | 108a | 20a | 69a | 1a | 26a | 24a | 36a | 94a | 104a | 21a |

We claim:

1. A method for identifying a member of a mass-coded combinatorial library which is a ligand for biomolecule and assessing the effect of the binding of the ligand to the biomolecule, said mass-coded molecular library comprising compounds of the general formal $XY_n$, wherein n is an integer from 2 to about 6, X is a scaffold and each Y is, independently, a peripheral moiety, wherein said mass-coded combinatorial library is produced by reacting a scaffold precursor with a sufficient number of distant peripheral moiety precursors such that there exist at least about 250 distinct combinations of n peripheral moieties derived from said peripheral moiety precursors, said method comprising the steps of:

(a) contacting the biomolecule with the mass-coded molecular library, whereby members of the mass-coded molecular library which are ligands for the biomolecule bind to the biomolecule to form biomolecule-ligand complexes and members of the mass-coded library which are not ligands for the biomolecule remain unbound;

(b) separating the biomolecule-ligand complexes from the unbound members of the mass-coded molecular library;

(c) dissociating the biomolecule-ligand complexes;

(d) determining the molecular mass of each ligand to identify the set of n peripheral moieties present in each ligand, wherein the molecular mass of each ligand corresponds to a set of n peripheral moieties present in that ligand, thereby identifying a member of the mass coded combinatorial library which is a ligand for the biomolecule; and (e) assessing in an in vitro assay the effect of the binding of the ligand to the biomolecule on the function of the biomolecule.

2. The method of claim 1 wherein the in vitro assay is a cell proliferation assay, a cell death assay or a viral replication assay.

3. The method of claim 1 wherein the biomolecule is a protein or a nucleic acid molecule.

4. A method for identifying a member of a mass-coded combinatorial library which is a ligand for a biomolecule and assessing the effect of the binding of the ligand to the biomolecule, said mass-coded molecular library comprising compounds of the general formula $XY_n$, wherein n is an integer from 2 to about 6, X is a scaffold and each Y is independently, a peripheral moiety, wherein said mass-coded combinatorial library is produced by reacting a scaffold precursor with a sufficient number of distinct peripheral moiety precursors such that there exist at least about 250 distinct combinations of n peripheral moieties derived from said peripheral moiety precursors, said method of comprising the steps of:
  (a) contacting the biomolecule with the mass-coded molecular library, whereby members of the mass-coded molecular library which are ligands for the biomolecule bind to the biomolecule to form biomolecule-ligand complexes and members of the mass-coded library which are not ligands for the biomolecule remain unbound;
  (b) separating the biomolecule-ligand complexes from the unbound members of the mass-coded molecular library;
  (c) dissociating the biomolecule-ligand complexes;
  (d) determining the molecular mass of each ligand to identify the set of n peripheral moieties present in each ligand,
wherein the molecular mass of each ligand corresponds to a set of n peripheral moieties present in that ligand, thereby identifying a member of the mass-coded combinatorial library which is a ligand for the biomolecule; and
  (e) assessing in an in vivo assay the effect of the binding of the ligand to the biomolecule on function of the biomolecule.

5. The method of claim 4 wherein the effect of the binding of the ligand to the biomolecule on the function of the biomolecule is assessed in an animal model, in an organism or in a human.

6. The method of claim 4 wherein the biomolecule is a protein or a nucleic acid molecule.

7. A method of evaluating the validity of a biomolecule for therapeutic intervention, the method comprising:
  (a) providing a biomolecule wherein the function of the biomolecule is undefined;
  (b) contacting the biomolecule with a solubilized mass-coded library, said mass-coded molecular library comprising compounds of the general formula $XY_n$, where n is an integer from 2 to about 6, X is a scaffold and each Y is, independently, a peripheral moiety, wherein said mass-coded combinatorial library is produced by reacting a scaffold precursor with a sufficient number of distinct peripheral moiety precursors such that there exist at least about 250 distinct combinations of n peripheral moieties derived from said peripheral moiety precursors, under conditions wherein members of the mass-coded library that are ligands for the biomolecule form ligand-biomolecule complexes;
  (c) separating the ligand-biomolecule complexes from the unbound members of the mass-coded molecular library;
  (d) dissociating the biomolecule-ligand complexes;
  (e) identifying one or more ligands bound to the biomolecule using mass spectrometry, wherein the molecular mass of each ligand corresponds to a set of n peripheral moieties present in that ligand;
  (f) providing a cell that expresses the biomolecule;
  (g) assaying the effect of a ligand identified in step (e) upon contact with the cell of step (f); and
  (h) observing whether a particular cellular process of the cell of step (f) is altered in the presence of the ligand of step (e), wherein if the cellular process of the cell of step (f) is altered upon contact with the ligand of step (e), determining that the biomolecule is a valid target for therapeutic intervention.

8. The method of claim 7, wherein the biomolecule is a protein.

9. The method of claim 7, wherein the biomolecule is a nucleic acid.

10. The method of claim 7, wherein the effect of the ligand of step (e) upon contact with the cell of step (f) is measured in an in vitro assay.

11. The method of claim 10, wherein the assay is a cell death assay.

12. The method of claim 10, wherein the assay is a cell proliferation assay.

13. The method of claim 10, wherein the assay is a viral replication assay.

14. The method of claim 7, wherein the effect of the ligand of step (e) upon contact with the cell of step (f) is assayed in vivo.

15. The method of claim 14, wherein the effect of the ligand of step (e) upon contact with the cell of step (f) is measured in an assay in an animal model.

16. The method of claim 15, wherein the animal is a human.

17. The method of claim 7, wherein the biomolecule is immobilized onto a solid support and the ligand-biomolecule complexes are separated from the unbound ligands using a wash of a buffer solution.

18. The method of claim 7, wherein the ligand-biomolecule complexes are separated from the unbound ligands by altering the pH of the solution in which the mass-coded compounds are solubilized.

19. The method of claim 7, wherein the ligand-biomolecule complexes are separated from the unbound ligands by altering the percentage of organic solvent present in the solution in which the mass-coded compounds are solubilized.

20. The method of claim 7, wherein the ligand-biomolecule complexes are separated from the unbound ligands using gel filtration.

21. The method of claim 7, wherein the ligand-biomolecule complexes are separated from the unbound ligands using ultrafiltration.

22. The method of claim 7, wherein the ligand-biomolecule complexes are separated from the unbound ligands using size exclusion chromatography.

23. The method of claim 7, further comprising subjecting one or more ligands dissociated from the biomolecule-ligand complexes to liquid chromatography.

* * * * *